United States Patent [19]

Hagiwara

[11] Patent Number: 5,629,768
[45] Date of Patent: May 13, 1997

[54] DEFECT INSPECTING APPARATUS

[75] Inventor: Tsuneyuki Hagiwara, Kawasaki, Japan

[73] Assignee: Nikon Corporation, Tokyo, Japan

[21] Appl. No.: 396,325

[22] Filed: Feb. 28, 1995

Related U.S. Application Data

[63] Continuation of Ser. No. 187,492, Jan. 28, 1994, abandoned.

[30] Foreign Application Priority Data

| Jan. 28, 1993 | [JP] | Japan | 5-012959 |
| Jan. 28, 1993 | [JP] | Japan | 5-012960 |

[51] Int. Cl.$^6$ .................................... G01N 21/88
[52] U.S. Cl. ........................................... 356/237
[58] Field of Search ............................ 356/237, 239, 356/336

[56] References Cited

U.S. PATENT DOCUMENTS

| 3,658,420 | 4/1972 | Axelrod | 356/239 |
| 4,360,269 | 11/1982 | Iwamoto et al. | 356/239 |
| 4,601,577 | 7/1986 | Gotou et al. | 356/237 |
| 4,871,257 | 10/1989 | Suzuki et al. | 356/237 |
| 4,893,929 | 1/1990 | Miyamoto | 356/336 |
| 5,177,559 | 1/1993 | Batchelder et al. | 356/237 |
| 5,442,189 | 8/1995 | Hagiwara | 356/237 |

*Primary Examiner*—Richard A. Rosenberger
*Attorney, Agent, or Firm*—Shapiro and Shapiro

[57] ABSTRACT

The defect inspecting apparatus of this invention is provided with a light source for applying illuminating light, illuminating means for applying the illuminating light from the light source onto the surface of a substrate to be inspected, a lens system for condensing the beam of light from the surface to be inspected and creating a spatial frequency spectrum on a Fourier transform plane to the surface to be inspected or a plane conjugate therewith, a light intercepting member for setting a spectrum-free area in the spatial frequency spectrum of the light from a pattern, the light intercepting member being disposed between the light source and the substrate and being effective to intercept part of the illuminating light, a space filter disposed on the Fourier transform plane or the plane conjugate therewith for passing therethrough the light in the spectrum-free area, light receiving means for receiving the beam of light passed through the space filter and outputting a photoelectric signal, the beam of light passed through the space filter being created from a defect on the surface to be inspected, and signal processing means for inspecting the surface state of the substrate on the basis of the photoelectric signal. When the circuit pattern on the surface to be inspected is an errorless circuit pattern having no defect, a spectrum-free area is set on the Fourier transform plane of that circuit pattern by the light intercepting member. When there is a defect in the circuit pattern on the surface to be inspected, a spectral component is created in the spectrum-free area. So, the light in the spectrum-free area is directed to the light receiving means by the space filter, whereby only the defect information is extracted.

14 Claims, 34 Drawing Sheets

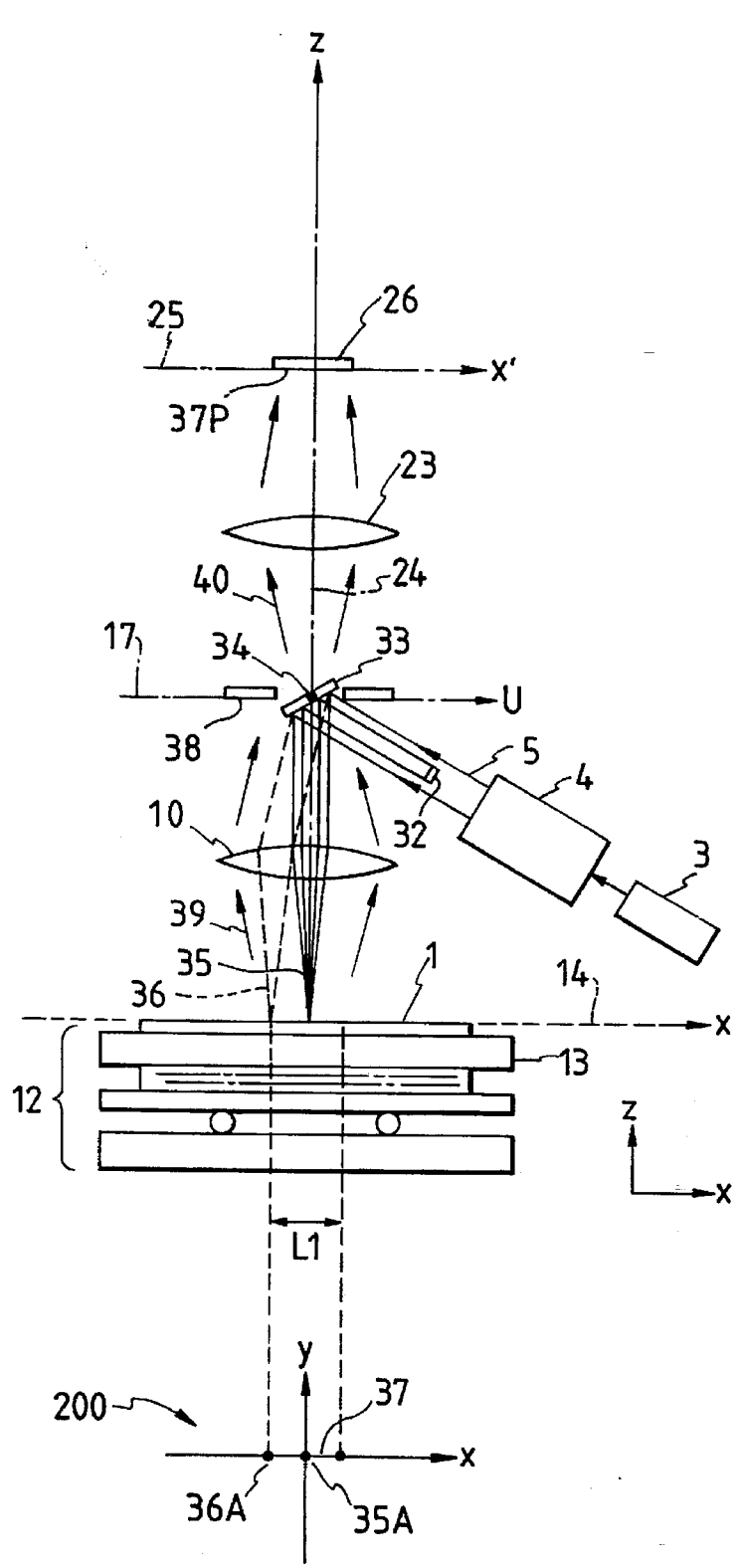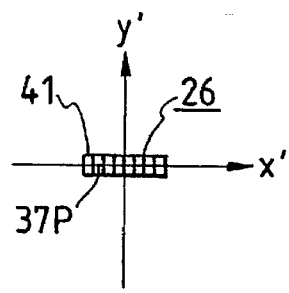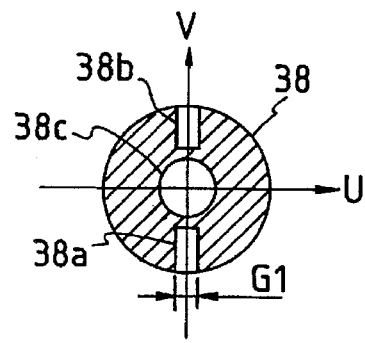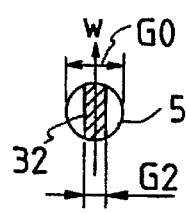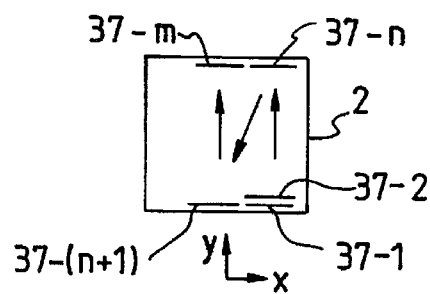
FIG. 1A
FIG. 1C
FIG. 1D
FIG. 1B
FIG. 1E

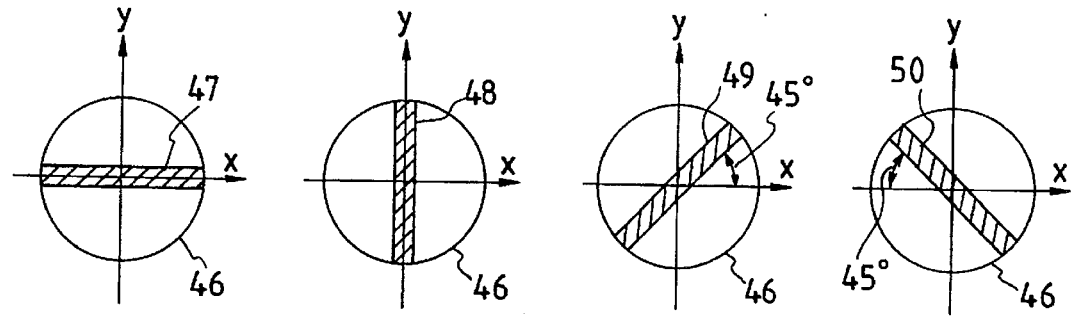
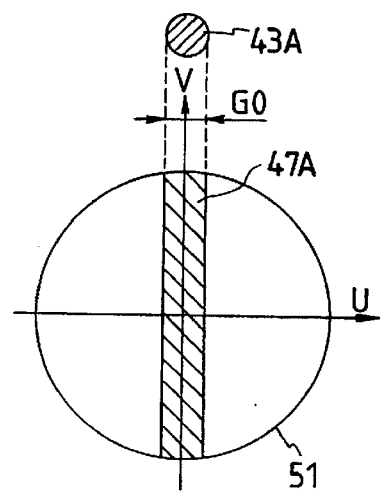
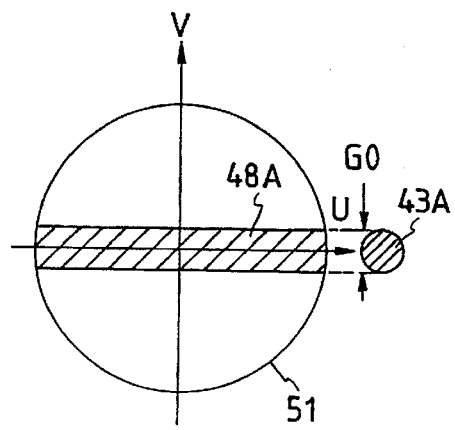
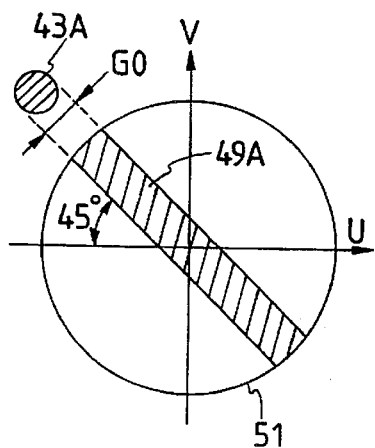
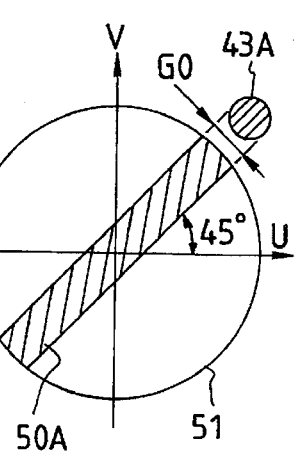
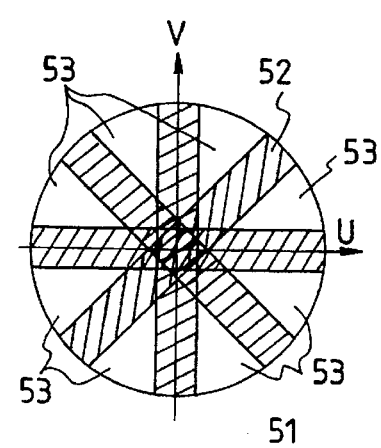

FIG. 17A
FIG. 17B
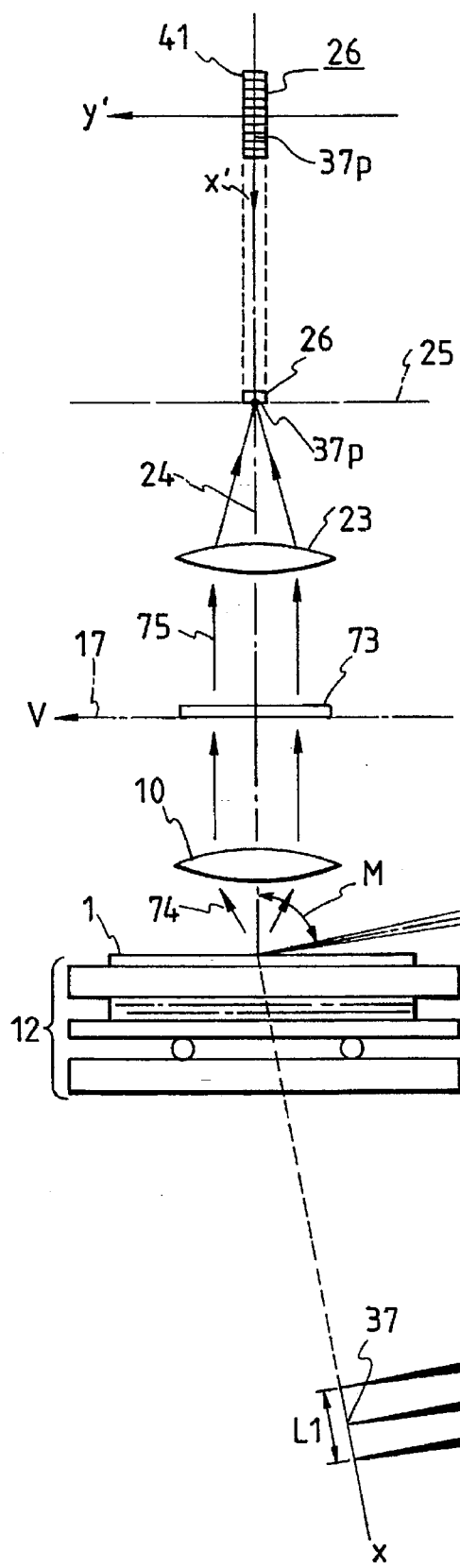
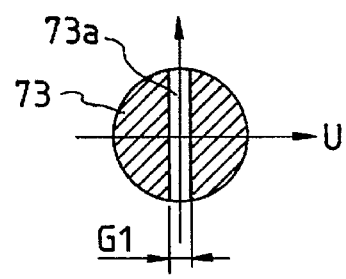
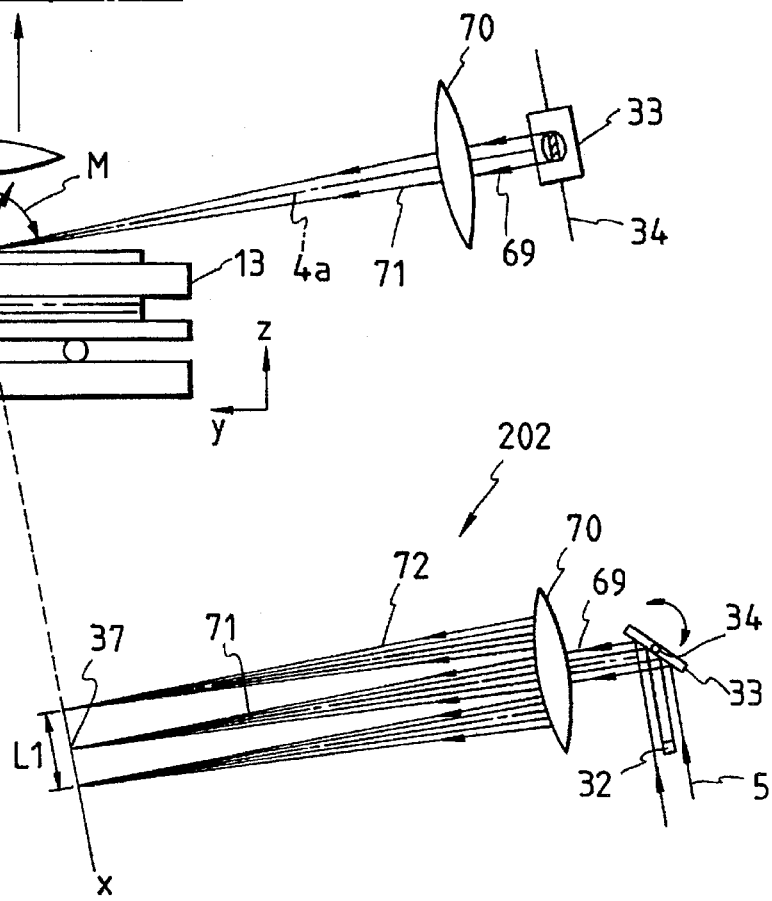

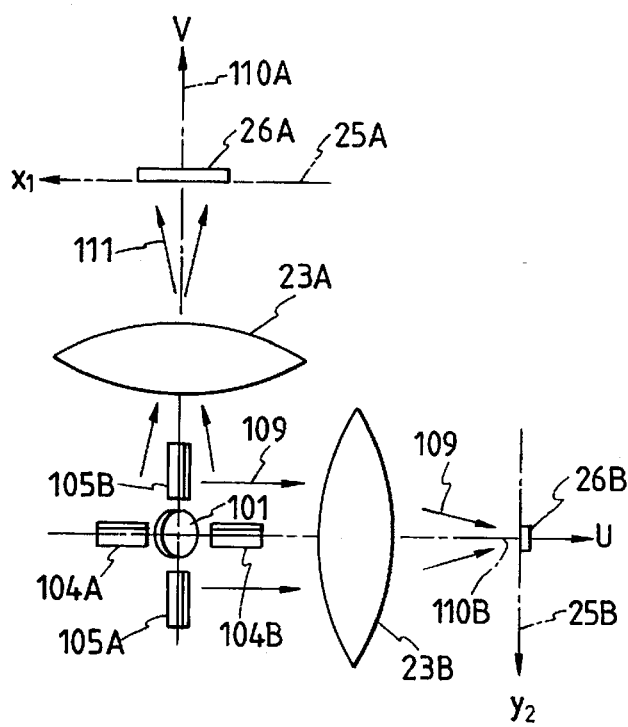
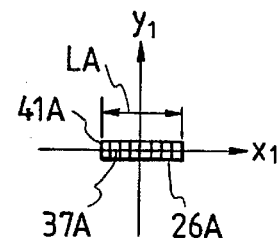
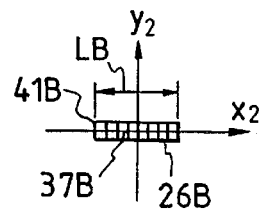
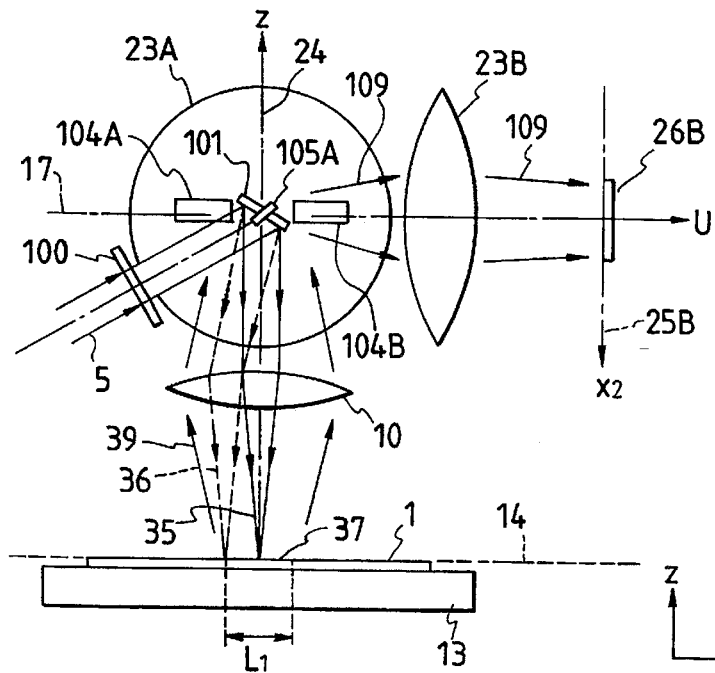
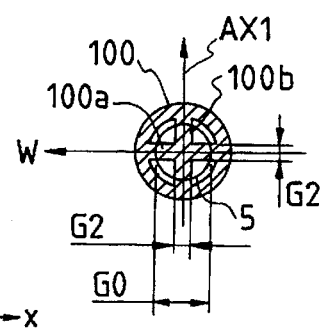

DEFECT INSPECTING APPARATUS

This is a continuation of application Ser. No. 08/187,492 filed Jan. 28, 1994, now abandoned.

BACKGROUND OF THE INVENTION

1. Field of the Invention

This invention relates to a defect inspecting apparatus, and particularly to a defect inspecting apparatus suitable for use in detecting the defect of a circuit pattern or a reticle or a photomask used as a negative in the manufacture of a semiconductive element or the like, or defects such as foreign substances on a substrate such as a semiconductive wafer.

2. Related Background Art

A defect inspecting apparatus is used in detecting, for example, the defect of a circuit pattern on a reticle or a photomask used as a negative in the manufacture of a semiconductive element or the like, or foreign substances on a substrate such as a semiconductive wafer.

FIG. 35A of the accompanying drawings shows a defect inspecting apparatus according to the prior art, and this defect inspecting apparatus is used to detect, for example, defects (including foreign substances) present on a semiconductive wafer. The wafer is provided with a number of redundant circuit patterns having periodical structure. FIG. 35B of the accompanying drawings shows a semiconductive wafer 1 which is the object of inspection. The semiconductive wafer 1 generally includes a regular array of circuit units (hereinafter referred to as the "dies") 2. Each die 2 has at least several tens of redundant circuit patterns along x axis and y axis, respectively. Each die 2 typically is a square having a side of about 20 mm.

In FIG. 35A, the inspecting apparatus is provided with a laser source 3, and a monochromatic laser beam emitted from the laser source 3 is converted into a substantially parallel beam of light 5 having a predetermined diameter by a beam expander 4. The beam of light 5 is then converged on a focus 7 positioned in the rearward focal plane of a lens 6, by the lens 6. A beam of light 8 diverging from the focus 7 is reflected by a small reflecting mirror 9 located near the focus 7. A beam of light of a circular cross-sectional shape reflected by the reflecting mirror 9 travels toward a Fourier transform lens 10.

The lens 10 is located such that the distance from the reflecting mirror 9 to the actually effective center of the lens 10 is a distance slightly smaller than one time the focal length of the lens 10. A parallel beam of light 11 emerging from the lens 10 is projected onto the surface of the semiconductive wafer 1 on which the patterns are formed. The semiconductive wafer 1 is held in a chuck 13 forming a part of two-dimensional parallel-moving means 12. The two-dimensional parallel-moving means 12 can move the semiconductive wafer 1 two-dimensionally in a plane perpendicular to the optical axis of the lens 10. The semiconductive wafer 1 is located in the object plane (i.e., the forward focal plane) 14 of the lens 10, and the parallel beam of light 11 illuminates the surface of the semiconductive wafer 1 on which the patterns are formed. In the optical system of FIG. 35A, the reflecting mirror 9 is a half mirror.

The portion 206 of FIG. 35A shows the manner in which the object plane 14 of the lens 10 is seen from above (from Z direction). As shown in the portion 206 of FIG. 35A, the parallel beam of light 11 illuminates the illuminated area 15 of a diameter 20 mm on the surface of the semiconductive wafer 1. As shown in FIG. 35A, a beam of light 16 diffracted by the illuminated area on the semiconductive wafer 1 is directed to the Fourier transform plane (i.e., the rearward focal plane) 17 of the lens 10 by the lens 10. The Fourier transform patterns of the circuit patterns in the illuminated area on the surface of the semiconductive wafer 1 are imaged in the Fourier transform plane 17.

Where the semiconductive wafer 1 is a wafer having no circuit (i.e., a wafer on which the circuit patterns are not yet formed), it is as shown in FIG. 36 of the accompanying drawings. FIG. 36 is a schematic view of the essential portions of the inspecting apparatus of FIG. 35A. In the inspecting apparatus of FIG. 36, the diameter of the beam spot at the rearward focus of the lens 6 is in inverse proportional relation with the diameter of the monochromatic parallel beam of light 5 projected from the beam expander 4 onto the lens 6. The beam of light 8 diverging from the focus 7 travels toward a half mirror 18, and the beam of light having a circular cross-section reflected by the half mirror 18 travels toward the Fourier transform lens 10. The parallel beam of light 11 emerging from the lens 10 is reflected by the wafer 1A having no circuit, whereafter it is again transmitted through the lens 10 and becomes a beam of light 19, which forms a beam spot 20 on the Fourier transform plane 17 of the lens 10. The beam diameter of the beam spot 20 becomes substantially equal to the beam diameter at the focus 7.

Turning back to FIGS. 35A and 35B, the illuminated area 15 of a diameter 20 mm on the semiconductive wafer 1 provides a Fourier transform pattern of sufficient accuracy. The reason is that the semiconductive wafer 1 comprises a number of redundant circuit patterns.

Also, a space filter 21 prepared in advance is disposed in the Fourier transform plane (the rearward focal plane) 17 of the Fourier transform lens 10. The space filter 21 can be made by exposing a recording medium like a photographic dry plate to light diffracted by all dies 2 of the semiconductive wafer 1. This can be done by the use of the semiconductive wafer 1 to be inspected. The reason is that even if the patterns on the semiconductive wafer 1 include defects, defect information will be conveyed by light of relatively low intensity and the light of low intensity including the defect information will not expose the photographic dry plate, whereas Fourier transform information of relatively high intensity from the original pattern on the semiconductive wafer 1 (light from the pattern) will expose the photographic dry plate.

Accordingly, the space filter 21 blocks the spatial frequency of the errorless Fourier transform information of the illuminated dies 2 on the semiconductive wafer (the Fourier transform information from the patterns free of defect), but passes therethrough the light created from the defect in these dies 2. The beam of light 22 conveying the defect information which is not blocked by the space filter 21 enters a reverse Fourier transform lens 23. This lens 23 is shown as a single lens, but includes a case where it is comprised of a plurality of lens elements. Also the lens 23 is located at a distance one time as great as the focal length of the lens 23 from the Fourier transform plane 17 of the lens 10. The lenses 10 and 23 are aligned along the same optical path 24, and the two-dimensional parallel-moving means 12 moves the semiconductive wafer 1 in a direction intersecting the optical axis 24. The lens 23 reversely Fourier-transforms the filtered light patterns of the illuminated dies 2 on the semiconductive wafer 1, and forms the images of the defects of the dies 2 in the rearward focal plane, i.e., the image plane, of the lens 23.

A photodetector array 26 is disposed about the optical axis 24 on the rearward focal plane of the lens 23, i.e., the image plane 25 on which the images of the defects are formed, and the respective light receiving elements of the photodetector array 26 receive the images of the defects present in the dies 2 on the optical axis 24.

In such prior art, to make electronic or optical noise sufficiently small, the design conditions of the Fourier transform lens 10 and reverse Fourier transform lens 23 become very severe.

To make optical noise sufficiently small, a severe limitation is imposed on the minimum spot diameter on the Fourier transform plane 17 and the minimum spot diameter on the image plane 25. Also, to make electronic noise sufficiently small, the lens 10 and lens 23 must be designed such that light diffracted in a telecentric cone of ±15° or greater from any point in the field of view located on the object plane (forward focal plane) 14 of the lens is made into parallel rays of light with sufficiently small aberrations and a paraxial diffracted light image is finally formed with very small geometric strain.

From the conditions as described above, as shown in FIGS. 35A and 35B, in the illuminated area 15 on the semiconductive wafer 1, an observation field 27 which is a field of view in which the defect can be detected with sufficiently small electronic or optical noise becomes small as compared with the illuminated area 15. Also, the optimum illuminated area when exposing the space filter 21 is the illuminated area 15, and also when observing only the interior of the observation field 27, the illuminated area 15 of the same dimensions must be illuminated. The reason is that the Fourier transform patterns of the circuit patterns of the illuminated dies 2 need be made the same both during the making of the space filter 21 and during the defect inspecting operation.

With regard to this, as shown, for example, in FIG. 37 of the accompanying drawings, suppose an inspecting apparatus for illuminating the same area as the observation area 27 of FIGS. 35A and 35B. That is, in FIG. 37, a parallel beam of light 29 of a small diameter emerging from the Fourier transform lens 10 illuminates only the interior of the observation field. In this case, the useless illuminated area (the hatched portion of FIGS. 35A and 35B) created in the illuminated area 15 of FIGS. 35A and 35B is not created, but yet the diameter of a beam spot 31 formed in the Fourier transform plane 17 by the reflected light 30 from the wafer 1A of FIG. 37 having no circuit becomes large as compared with the diameter of the beam spot 20 in the case of FIG. 36, and this light cannot completely be intercepted by the space filter on the Fourier transform plane 17. Therefore, it is necessary to illuminate the illuminated area 15 during the detect inspection as well, and it has been difficult to apply illuminating light of sufficient illuminance to the interior of the observation field 27.

Also, the illuminance of the illuminating light in the observation field 27 shown in FIG. 35B affects the inspection time. That is, the observation field 27 is not so large as to enable the whole of each die 2 on the semiconductive wafer 1 to be observed at a time and therefore, it becomes necessary to move the observation field 27 relative to the dies 2 in the respective dies 2. The relative movement velocity depends on the light cumulation time of the photodetector array 26 and the luminance in the observation field 27, and as the luminance becomes lower, the relative movement velocity also becomes lower as a matter of course. Also, in some cases, a light cumulation method such as time delay integration (TDI) is used in the photodetector array 26, but in such cases, the requirement for the accuracy of the relative movement becomes severe.

In the prior art as described above, the light from the errorless pattern of each die 2 on the semiconductive wafer 1 is intercepted by the space filter 21, whereby only the light from the defective portion of each die 2 may be directed to the photodetector array 26. However, there has been the inconvenience that it is difficult to expose, for example, a photographic dry plate properly and thereby prepare a space filter 21 capable of effecting defect detection accurately. Also this space filter 21 must strictly be prepared for each circuit pattern on the semiconductive wafer 1, and this has been very cumbersome.

SUMMARY OF THE INVENTION

In view of the above-noted points, the present invention has as its object the provision of a defect inspecting apparatus capable of inspecting in common the surface state of a substrate having various circuit patterns formed thereon, without using an exclusive space filter prepared by exposing a photographic dry plate or the like for each circuit pattern formed on the substrate which is the object of inspection and without creating any false defect which is originally not a defect but may be regarded as a defect.

In order to achieve such object, the defect inspecting apparatus of the present invention is provided with a light source for applying illuminating light, illuminating means for applying the illuminating light from the light source onto the surface of a substrate to be inspected, a lens system for condensing the beam of light from the surface to be inspected and creating a spatial frequency spectrum on a Fourier transform plane to the surface to be inspected or a plane conjugate therewith, a light intercepting member for setting a spectrum-free area in the spatial frequency spectrum of the light from a pattern, the light intercepting member being disposed between the light source and the substrate and being effective to intercept part of the illuminating light, a space filter disposed in the Fourier transform plane or the plane conjugate therewith and passing therethrough the light in the spectrum-free area, light receiving means for receiving the beam of light passed through the space filter and outputting a photoelectric signal, the beam of light passed through the space filter being created from a defect on the surface to be inspected, and signal processing means for inspecting the surface state of the substrate on the basis of the photoelectric signal.

According to such present invention, when the circuit pattern on the surface to be inspected is an errorless circuit pattern having no defect, a spectrum-free area is set on the Fourier transform plane of that circuit pattern. When the circuit pattern on the surface to be inspected has any defect, a spectral component is created in the spectrum-free area. So, the light in the spectrum-free area is directed to the light receiving means by the space filter, whereby only the defect information is extracted.

According to the present invention, provision is made of the light intercepting member for setting the spectrum-free area, and the space filter for passing therethrough the light in the spectrum-free area, and this leads to the advantage that the surface state of a substrate having various circuit patterns formed thereon can be inspected in common without using an exclusive space filter prepared by exposing a photographic dry plate or the like for each circuit pattern formed on the substrate which is the object of inspection and without creating any false defect which is originally not a defect but may be regarded as a defect.

According to the defect inspecting apparatus of the present invention, which is provided with the light intercepting member for setting the spectrum-free area and a dividing member for dividing the light in the spectrum-free area, there is the advantage that the surface state of a substrate having various circuit patterns formed thereon can be inspected in common without using an exclusive space filter prepared by exposing a photographic dry plate or the like for each circuit pattern formed on the substrate which is the object of inspection and without creating any false defect which is originally not a defect but may be regained as a defect.

Also, if the illuminating means has condensing means for condensing the illuminating light incident on the substrate and provision is made of relative scanning means for scanning the illuminating light condensed on the substrate and the substrate relative to each other, the SN ratio of a detection signal obtained from the light receiving means could be improved.

Also, if provision is made of first driving means for rotating the light intercepting member about the optical axis of the illuminating means, second driving means for rotating the space filter about the optical axis of the lens system, and control means for controlling the first driving means and the second driving means so that the light intercepting member and the space filter may be rotated in synchronism with each other, a detection signal of a high SN ratio could be obtained in conformity with the circuit patterns on the surface to be inspected.

The illuminating light may be any of monochromatic light, a plurality of monochromatic lights and light having a continuous wavelength spectrum, and can accomplish defect detection at a high SN ratio.

According to another embodiment of the present invention, the defect inspecting apparatus includes a light source for applying illuminating light, illuminating means for applying the illuminating light from the light source onto the surface of a substrate to be inspected, a lens system for condensing a beam of light created from the surface to be inspected and creating a spatial frequency spectrum on a Fourier transform plane to the surface to be inspected or a plane conjugate therewith, a light intercepting member for setting a spectrum-free area in the spatial frequency spectrum of a pattern, the light intercepting member being disposed between the light source and the substrate and being effective to intercept part of the illuminating light, a dividing member disposed on the Fourier transform plane or the plane conjugate therewith for dividing the beam of light from the substrate into a plurality of beams of light, a plurality of light receiving means for converting the plurality of beams of light into photoelectric conversion signals, and signal processing means for inspecting the surface state of the substrate on the basis of the plurality of photoelectric conversion signals.

According to such defect inspecting apparatus of the present invention, where the circuit pattern on the surface to be inspected is an errorless circuit pattern having no defect, a spectrum-free area is set on the Fourier transform plane of that circuit pattern by the light intercepting member. Where the circuit pattern on the surface to be inspected has a defect, a spectral component is created in the spectrum-free area. So, the light in the spectrum-free area is divided into a plurality of beams of light by the dividing member and these beams of light are directed to the plurality of light receiving means, whereby substantially only the defect information is extracted. Further, one of the photoelectric conversion signals from the plurality of light receiving means which is smaller is selected by the signal processing means, whereby a signal corresponding to a true defect can be detected.

According to the present invention, since provision is made of the light intercepting member for setting the spectrum-free area and the dividing member for dividing the light in the spectrum-free area, the surface state of a substrate having various circuit patterns formed thereon can be inspected in common without using an exclusive space filter prepared by exposing a photographic dry plate or the like for each circuit pattern formed on the substrate which is the object of inspection and without creating any false defect which is originally not a defect but may be regarded as a defect.

Next, if the illuminating means has condensing means for condensing the illuminating light incident on the substrate and provision is made of relative scanning means for scanning the illuminating light condensed on the substrate and the substrate relative to each other, the surface to be inspected will be illuminated by illuminating light of high illuminance and therefore, the SN ratio of the signals outputted from the light receiving means will be improved.

Also, when the dividing member has a plurality of mirrors and a space filter for intercepting the spatial frequency spectrum component of the circuit pattern on the substrate, the spatial frequency spectrum of that circuit pattern itself can be eliminated more completely and the SN ratio of the detection signal corresponding to the defect will be improved.

Further, where the incidence plane of the illuminating light is inclined with respect to the patterns on the surface to be inspected, the 0-order light from the circuit patterns on the surface to be inspected can be easily eliminated and therefore, the original influence of the circuit patterns can be further reduced.

Also, when the dividing member is disposed in the spectrum-free area, defect detection is effected at a particularly high SN ratio.

Also, when the dividing member has a plurality of mirrors and a space filter, defect detection can be effected with the original influence of the circuit patterns reduced.

The illuminating light may be any of monochromatic light, a plurality of monochromatic lights and light having a continuous wavelength spectrum, and can accomplish defect detection at a high SN ratio.

According to still another embodiment, the defect inspecting apparatus includes a light source for applying illuminating light, illuminating means for applying the illuminating light from the light source onto the surface of a substrate to be inspected, a lens system for condensing a beam of light created from the surface to be inspected and creating a spatial frequency spectrum on a Fourier transform plane to the surface to be inspected or a plane conjugate therewith, a space filter disposed between the light source and the substrate for intercepting the spatial frequency spectrum of a circuit pattern on the substrate, a dividing member disposed in the Fourier transform plane or the plane conjugate therewith for dividing the beam of light from the substrate into a plurality of beams of light, a plurality of light receiving means for converting the plurality of beams of light after divided into photoelectric conversion signals, and signal processing means for inspecting the surface state of the substrate on the basis of the plurality of photoelectric conversion signals.

According to the defect inspecting apparatus of the present invention, the spatial frequency spectrum of the circuit pattern on the substrate is intercepted by a light intercepting member. This spatial frequency spectrum after intercepted becomes free of spectrum when the circuit pattern on the surface to be inspected is an errorless circuit pattern having no defect. When the circuit pattern on the surface to be inspected has a defect, a spectral component is created in the spatial frequency spectrum after intercepted. So, the light in the spectrum-free area is divided into a plurality of beams of light by the dividing member and the plurality of beams of light are directed to the plurality of light receiving means, whereby substantially only the defect information is extracted. Further, one of the photoelectric conversion signals from the plurality of light receiving means which is smaller is selected by the signal processing means, whereby a signal corresponding to a true defect can be detected.

Also, when the illuminating means applies the illuminating light from an inclined direction onto the circuit pattern on the substrate and the dividing means is provided in an area wherein the spatial frequency spectrum of the circuit pattern when there is no defect in the substrate does not exist, the original Fourier spectrum of the circuit pattern on the substrate is eliminated substantially completely, and the defect information can be detected at a high SN ratio.

Also, the defect inspecting apparatus of the present invention, which is provided with the dividing member for dividing chiefly the light in the spectrum-free area and the plurality of light receiving means for receiving the beams of light from the dividing member, has the advantage that it can inspect in common the surface state of a substrate having various circuit patterns formed thereon, without using an exclusive space filter prepared by exposing a photographic dry plate or the like for each circuit patterns formed on the substrate which is the object of inspection and without creating any false defect which is originally not a defect but may be regarded as a defect.

Again in this case, when the dividing member is disposed in the spectrum-free area, defect detection is effected at a particularly high SN ratio.

BRIEF DESCRIPTION OF THE DRAWINGS

FIG. 1A shows the construction of a defect inspecting apparatus according to a first embodiment of the present invention.

FIG. 1B shows a light intercepting member 32 in FIG. 1A as it is seen in the direction of travel of a beam of light 5.

FIG. 1C is a plan view showing a photodetector array 26 in FIG. 1A.

FIG. 1D is a plan view showing a light intercepting member 38 in FIG. 1A.

FIG. 1E is a plan view showing an example of a method of moving a die 2 and an illuminated area on a semiconductive wafer 1 in FIG. 1A relative to each other.

FIGS. 4A, 4B, 4C and 4D are plan views showing some examples of linear patterns in various directions which are the objects of defect inspection.

FIGS. 5A, 5B, 5C, 5D and 5E are plan views showing Fourier transform patterns obtained by the linear patterns of FIGS. 4A to 4D being Fourier-transformed by the optical system of FIG. 2A.

FIG. 17A shows the construction of a fourth embodiment of the present invention.

FIG. 17B shows a light intercepting member 32 in the fourth embodiment as it is seen in the direction of travel of the beam of light 5.

FIG. 21A is a front view showing a defect inspecting apparatus according to a sixth embodiment of the present invention.

FIG. 21B is a plan view of the apparatus of FIG. 21A as it is seen in Z direction.

FIG. 21C shows an aperture plate 100 in FIG. 21A.

FIG. 21D shows a photodetector array 26A in FIG. 21B.

FIG. 21E shows a photodetector array 26B in FIG. 21B.

DESCRIPTION OF THE PREFERRED EMBODIMENTS

Figures 35A, 35B:
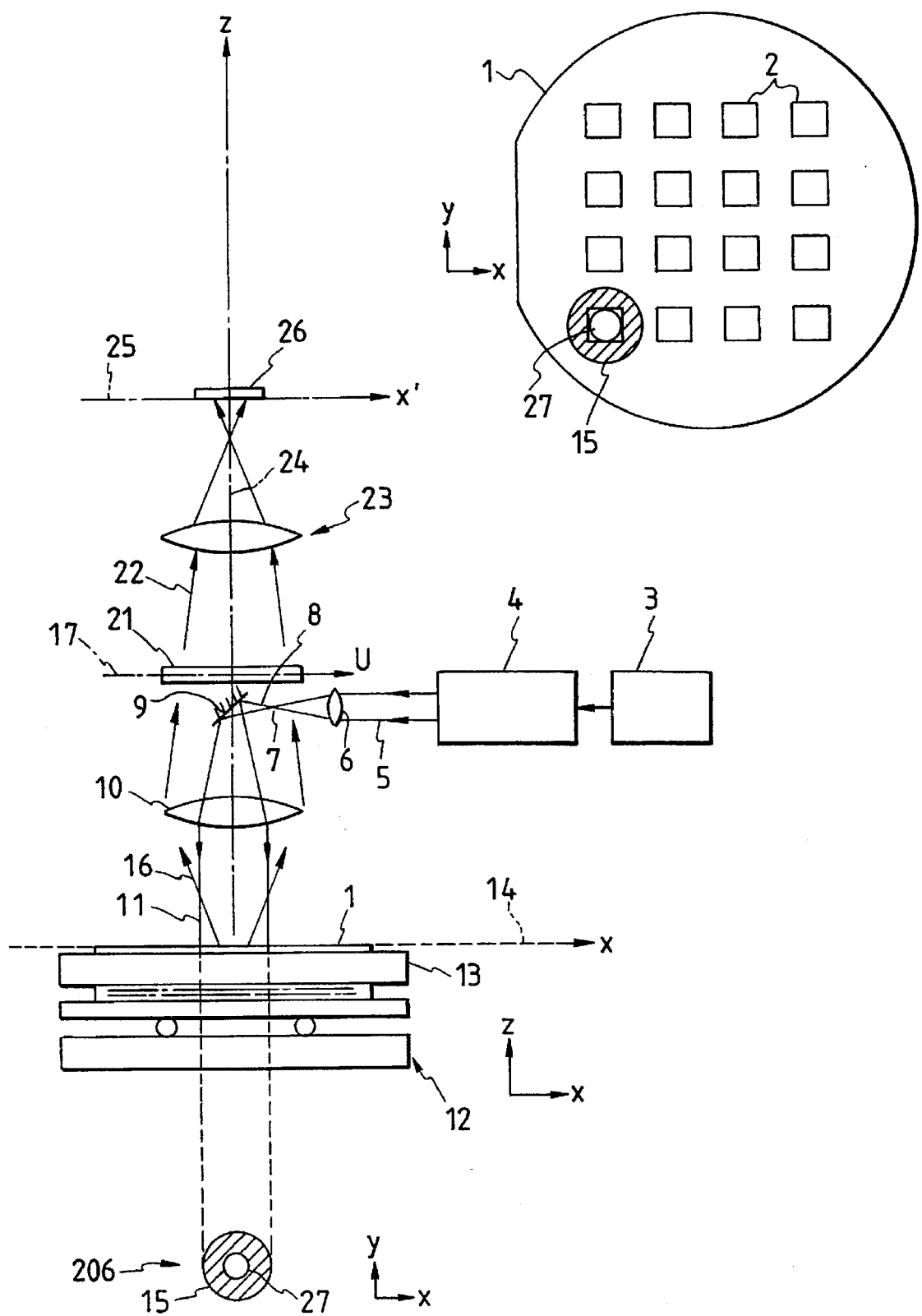
FIG. 35A shows the construction of a defect inspecting apparatus according to the prior art.
FIG. 35B is a plan view showing an illuminated area on a semiconductive wafer 1 in FIG. 35A.
Figure 36:
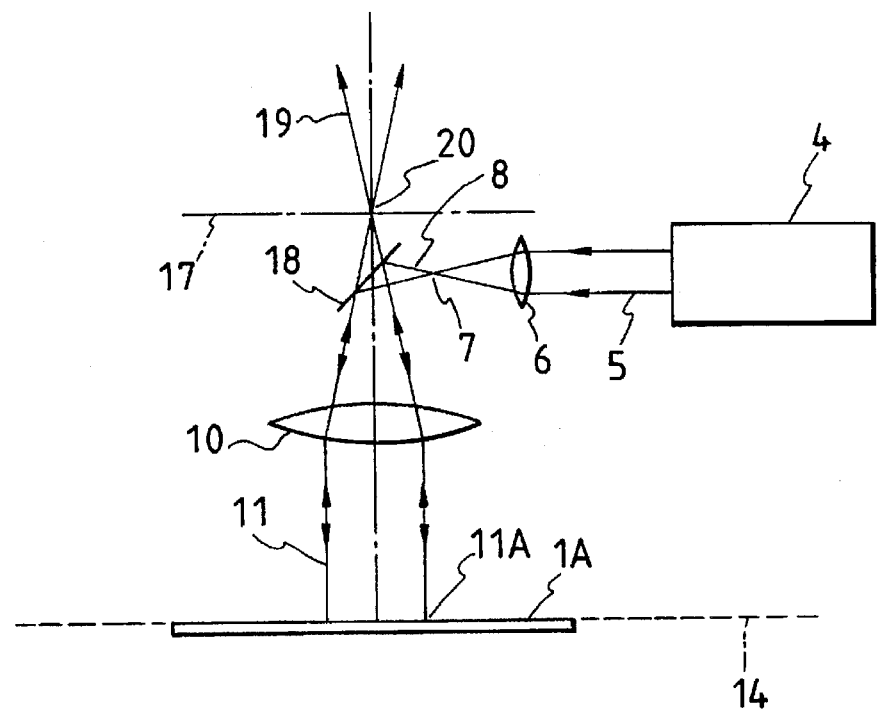
FIG. 36 shows the construction of the essential portions of the defect inspecting apparatus according to the prior art.
Figure 37:
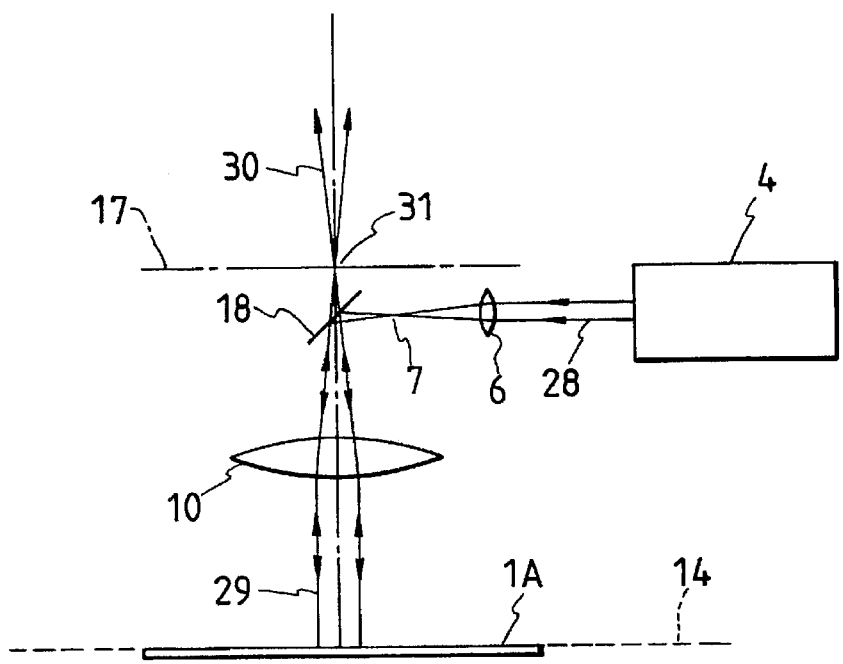
FIG. 37 shows the construction of the essential portions when the illuminated area is narrowed in the defect inspecting apparatus according to the prior art.

A first embodiment of the defect inspecting apparatus of the present invention will hereinafter be described with reference to FIG. 1A, etc. This embodiment is one in which the present invention is applied to an apparatus for detecting any defect present on a semiconductive wafer provided with a number of redundant circuit patterns having periodic structure, and in FIG. 1A, portions corresponding to those in FIG. 35A are given the same reference numerals and need not be described in detail. FIG. 1A schematically shows the construction of the defect inspecting apparatus according to the present embodiment. In FIG. 1A, a monochromatic laser beam from a laser source 3 is converted into a substantially parallel beam of light 5 of a diameter G0 by a beam expander 4, and this beam of light 5 is projected onto a light intercepting member 32 of a width G2. The light intercepting member 32 is a rectangular light intercepting pattern. The light intercepting member 32 has its lengthwise direction in W axis (see FIG. 1B). W axis is an axis passing through the center of the beam of light 5 extending in a direction perpendicular to the plane of the drawing sheet (xz plane) of FIG. 1A (i.e., a direction parallel to y axis). FIG. 1B is a cross-sectional view containing the W axis and perpendicular to the direction of travel of the beam of light 5. As shown in FIG. 1B, the beam of light 5 has its area of a width G2 about the W axis intercepted by the light intercepting member 32. The width G2 is about 20% of the diameter G0 of the beam of light 5. In FIG. 1A, the beam of light 5 passed through the light intercepting member 32 is incident on a vibratory mirror 33 located near the rearward focal plane (Fourier transform plane) of a Fourier transform lens 10. The vibratory mirror 33 is supported for vibration about a rotational axis 34 perpendicular to xz plane. The beam of light 5 is reflected by the vibratory mirror 33 and is reflected in the direction of a beam of light 35 or a beam of light 36. The beam of light 35 and the beam of light 36 are converged onto a semiconductive wafer 1 through a Fourier transform lens 10.

That is, the actually effective center of the Fourier transform lens 10 is disposed at a distance one time as great as the focal length of the lens 10 from the surface (xy plane) of the semiconductive wafer 1. The scanned beam of light 35 and beam of light 36 are converged onto the surface of the semiconductive wafer 1 by the angle of the vibratory mirror 33. As indicated by a portion 200 in FIG. 1A, convergence points 35A and 36A are formed. An illuminated area 37 of a distance L1 along x axis can be continuously scanned at those convergence points by a variation in the angle of the vibratory mirror 33. The portion 200 of FIG. 1A is a plan view of the surface of the semiconductive wafer 1 (xy plane) as it is seen from z direction. The x axis and y axis orthogonal to each other are parallel to the reference orthogonal axes during the depiction of circuit patterns formed on the semiconductive wafer 1. The xy plane of the portion 200 in FIG. 1A coincides with the object plane 14, and the origin thereof is on an optical axis 24.

In FIG. 1A, the semiconductive wafer 1 is mounted on a chuck 13. The chuck 13 is a part of two-dimensional parallel-moving means 12. The pattern formation surface of the semiconductive wafer 1 is located on the object plane (forward focal plane) 14 of the Fourier transform lens 10, and the converged beams of light 35 and 36 illuminate the surface of the semiconductive wafer 1 on which patterns are formed. A beam of light 39 diffracted by the illuminated area of the semiconductive wafer 1 passes through the Fourier transform lens 10 and arrives in the Fourier transform plane (rearward focal plane) 17 of the lens 10, and the Fourier transform patterns of the circuit patterns on the semiconductive wafer 1 are formed on the Fourier transform plane 17.

Description will now be made of the relation between the circuit patterns in the illustrated area of the semiconductive wafer 1 and the created Fourier transform patterns. The U axis and V axis of an orthogonal coordinates system having the point of intersection between the optical axis 24 and the rearward focal plane 17 of the lens 10 as its origin are first plotted in the rearward focal plane of the Fourier transform lens 10. The U axis and V axis indicate the image height of the Fourier transform lens 10.

The Fourier transform lens 10 has the characteristics of the following equations (1) and (2):

$$U = f \sin\theta_x = f \cdot l \quad (1)$$

$$V = f \sin\theta_y = f \cdot m \quad (2)$$

In this case, f is the focal length of the Fourier transform lens 10, $\theta_x$ is the x component of the angle of field and $\theta_y$ is the y component of the angle of field.

Now, Fourier transform information is usually indicated on an orthogonal coordinates system of spatial frequencies u and v. When the wavelength of the illuminating light converged onto the semiconductive wafer 1 is $\lambda$, the following equations are established by the definition of Fourier transform:

$$u = (l - l_0)/\lambda \quad (3)$$

$$v = (m - m_0)/\lambda \quad (4)$$

where respective variables are defined as follows:

l: the direction cosine of diffracted light (a component parallel to x axis)

$l_0$: the direction cosine of 0-order diffracted light (a component parallel to x axis)

m: the direction cosine of diffracted light (a component parallel to y axis)

$m_0$: the direction cosine of 0-order diffracted light (a component parallel to y axis)

Next, the positions $U_0$ and $V_0$ of 0-order diffracted light on UV plane are expressed by the following equations:

$$U_0 = f \cdot l_0 \quad (5)$$

$$V_0 = f \cdot m_0 \quad (6)$$

The following relations are derived from the above equations (1)–(6):

$$u = (U - U_0)/(\lambda \cdot f) \quad (7)$$

$$v = (V - V_0)/(\lambda \cdot f) \quad (8)$$

These equations (7) and (8) show that when the UV coordinates, i.e., the image heights, are similarly converted by a coefficient $(1/(\lambda \cdot f))$ and are parallel-moved by $(U_0/(\lambda \cdot f), V_0/(\lambda \cdot f))$, they become the orthogonal coordinates of the spatial frequencies u and v. In the present embodiment and second and third embodiments which will be described later, $U_0 = V_0 = 0$.

Figure 2A:
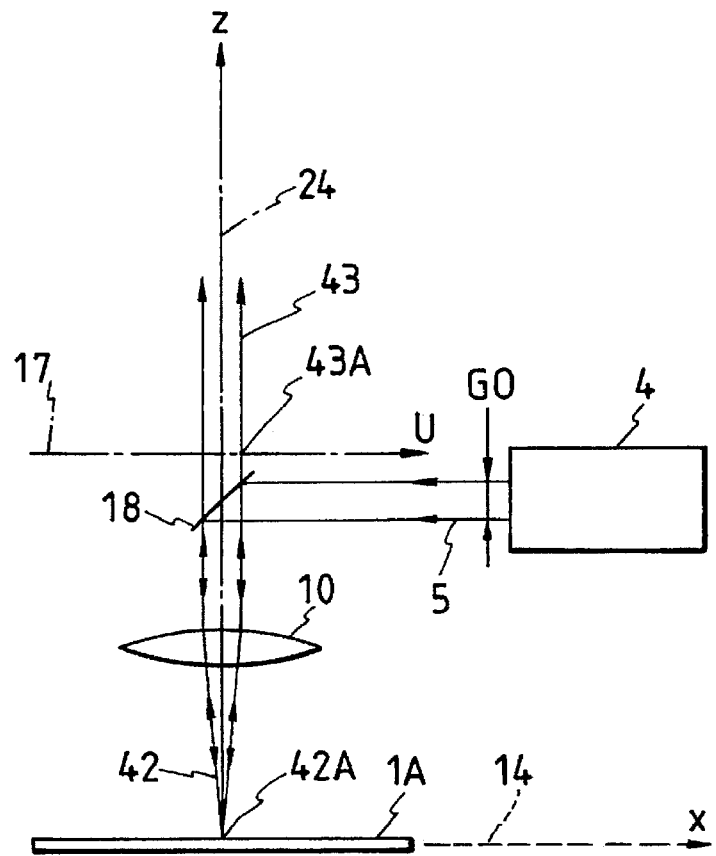
FIG. 2A shows the construction of the essential portions of an optical system equivalent to the optical system in the first embodiment from which the light intercepting member 32 is eliminated.

Next, suppose the optical system of FIG. 2A to compare it with the present embodiment. In FIG. 2A, there is formed no pattern on the surface of a semiconductive wafer 1A. A parallel beam of light 5 having a circular cross-section of a diameter G0 emerging from a beam expander 4 is reflected by a half mirror 18. The beam of light 5 then travels toward a Fourier transform lens 10 having an optical axis 24 coincident with z axis perpendicular to the semiconductive wafer 1A. The actually effective center of the Fourier transform lens 10 is disposed at a distance one time as great as the focal length of the lens 10 from the surface of the semiconductive wafer 1A having no pattern thereon. A beam of light 42 converged by the lens 10 is applied to the surface of the semiconductive wafer 1A having no pattern thereon.

Figure 2B:
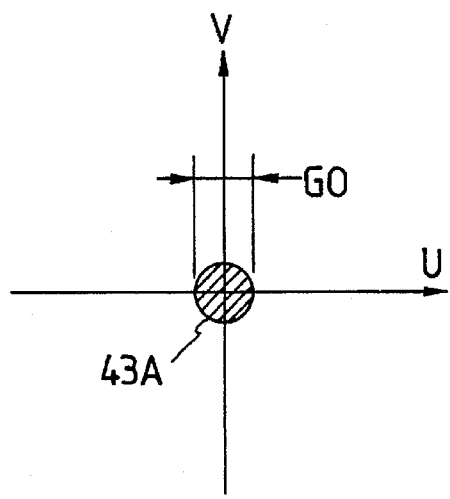
FIG. 2B shows the Fourier transform pattern of the optical system of FIG. 2A to a semiconductive wafer having no pattern thereon.

The surface of the semiconductive wafer 1A is located on the object plane (forward focal plane) 14 of the lens 10, and the converged beam of light 42 is reflected by the semiconductive wafer 1A. The beam of light 42 then travels back along the same optical path as when it impinges on the semiconductive wafer 1A and arrives at the half mirror 18. A beam of light 43 passed through the half mirror 18 forms the Fourier transform pattern 43A of the beam of illuminating light itself in the rearward focal plane 17 of the Fourier transform lens 10. FIG. 2B shows the Fourier transform pattern 43A on the Fourier transform plane (UV plane). This Fourier transform pattern 43A is nothing but the cross-sectional shape of the beam of light 5 (i.e., the circle of a diameter G0).

Figure 3A:
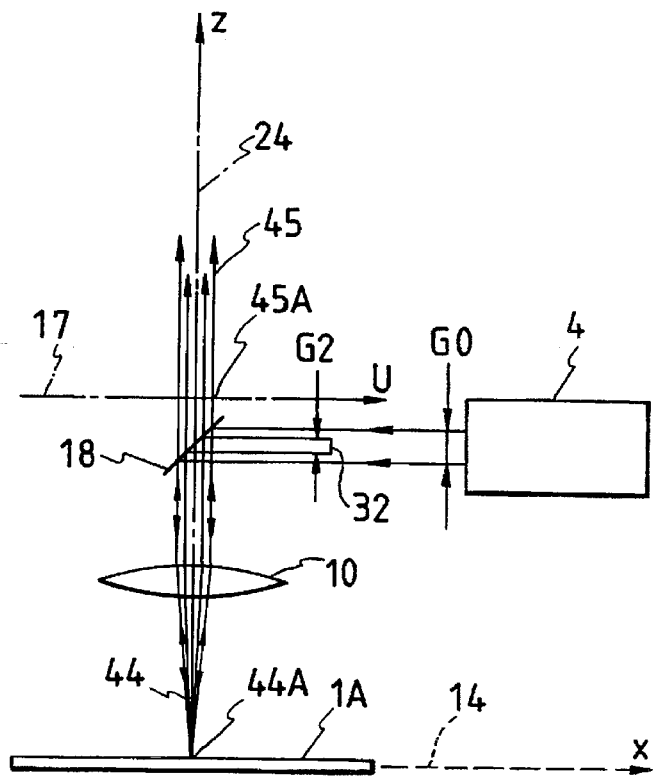
FIG. 3A shows the construction of the essential portions of an optical system equivalent to the optical system in the first embodiment.

Next, an optical system equivalent to the optical system of FIG. 1A and corresponding to FIG. 2A is such as shown in FIG. 3A.

In FIG. 3A, the parallel beam of light 5 having a circular cross-section of a diameter G0 emerging from the beam expander 4 is divided into two by a light intercepting member 32. That is, again in FIG. 3A, the beam of light 5 has its area of a width G2 about W axis intercepted by the light intercepting member 32.

Figure 3B:
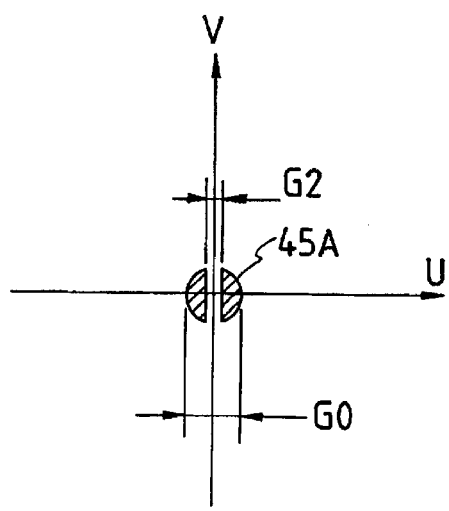
FIG. 3B shows the Fourier transform pattern of the optical system of FIG. 3A to a semiconductive wafer having no pattern thereon.

In FIG. 3A, the beam of light 5 passed through the light intercepting member 32 is reflected by the half mirror 18 and travels toward the Fourier transform lens 10. The optical axis 24 of the Fourier transform lens 10 coincides with z axis perpendicular to the semiconductive wafer 1A. The actually effective center of the Fourier transform lens 10 is located at a distance one time as great as the focal length of the lens 10 from the surface of the semiconductive wafer 1A having no pattern thereon, and a beam of light 44 converged by the Fourier transform lens 10 is applied onto the semiconductive wafer 1A having no pattern thereon. The surface of the semiconductive wafer 1A is located in the object plane (forward focal plane) 14 of the lens 10, and the converged beam of light 44 is converged at a point 44A. The converged beam of light 44 is reflected by the semiconductive wafer 1A, and travels back along the same optical path as that until it impinges on the semiconductive wafer 1A, and arrives at the half mirror 18. A beam of light 45 transmitted through the half mirror 18 forms the Fourier transform pattern 45A of the beam of illuminating light itself in the rearward focal plane 17 of the Fourier transform lens 10. This Fourier transform pattern 45A is such that as shown in FIG. 3B, the area of a width G2 along V axis passing through the center from the circular pattern of a diameter G0 is a patternless portion.

In order to compare the optical system of FIG. 2A and the optical system of FIG. 3A with each other, it is to be understood that in the optical system of FIG. 2A, instead of the semiconductive wafer 1A having no pattern thereon, a semiconductive wafer 1 on which circuit patterns 47, 48, 49 and 50 as shown in FIGS. 4A, 4B, 4C and 4D are formed in a die 2 is observed. In FIGS. 4A, 4B, 4C and 4D, an illuminated area 46 is an area to which the beam of light 42 of FIG. 2A is applied, and the circuit patterns 47 and 48 in the illuminated area 46 of FIGS. 4A and 4B are linear patterns of a predetermined width extending along x axis and y axis, respectively. Also the circuit patterns 49 and 50 in the illuminated area 46 of FIGS. 4C and 4D are ones formed by the circuit patterns 47 and 48 being each rotated counter-clockwisely.

When in the optical system of FIG. 2A, the circuit patterns 47, 48, 49 and 50 of FIGS. 4A, 4B, 4C and 4D, respectively, are Fourier-transformed, Fourier transform patterns 47A, 48A, 49A and 50A as shown in the transform area 51 of FIGS. 5A, 5B, 5C and 5D are obtained on UV plane which is the Fourier transform plane 17. The transform area 51 is a limit area in a spatial frequency area determined by the Fourier transform lens 10. In this case, the Fourier transform patterns 47A and 48A of FIGS. 5A and 5B are band-like patterns of a width G0 extending along V axis and U axis, respectively. The Fourier transform patterns 49A and 50A of FIGS. 5C and 5D are patterns formed by the Fourier transform patterns 47A and 48A being rotated counter-clockwisely. The width G0 of those Fourier transform patterns 47A, 48A, 49A and 50A are the same as the width G0 of the Fourier transform pattern 43A of the beam of illuminating light itself shown in FIG. 2B.

Accordingly, if a light intercepting member 52 made coincident with the width and directions of the band-like Fourier transform patterns 47A, 48A, 49A and 50A of FIGS. 5A, 5B, 5C and 5D is disposed in UV plane as shown in FIG. 5E so that only the beams of light from the areas 53 in the transform area 51 defined by the light intercepting member 52 may pass, the Fourier transform patterns by the circuit patterns 47–50 in the die on the semiconductive wafer shown in FIGS. 4A, 4B, 4C and 4D will not pass.

Figure 6A:
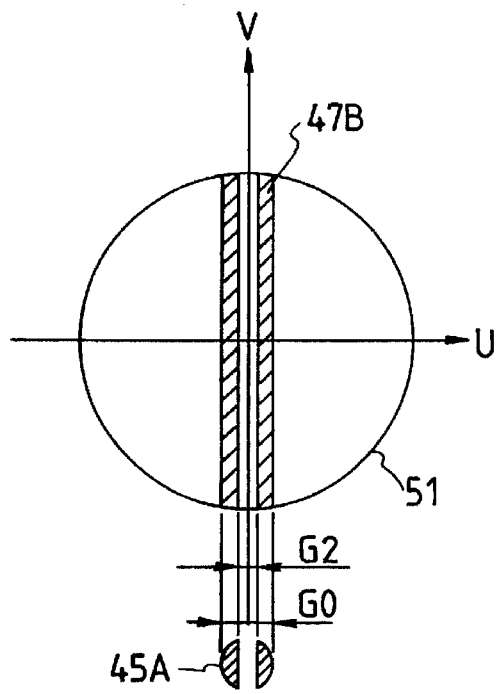
FIG. 6A is a plan view showing a Fourier transform pattern obtained by the linear pattern of FIG. 4A being Fourier-transformed by the optical system of FIG. 3A in the first embodiment.

On the other hand, when in the optical system of FIG. 3A according to the present embodiment, the circuit pattern 47 shown in FIG. 4A is present in the illuminated area 46, a Fourier transform pattern 47B shown in the transform area 51 of FIG. 6A is created on the Fourier transform plane 17. The transform area 51 is a limit area in a spatial frequency area determined by the Fourier transform lens 10. The Fourier transform pattern 47B is a band-like pattern of a width G0 extending along V axis, and a patternless portion of a width G2 is formed in the central portion thereof. These widths G0 and G2 in U direction are the same as the outer diameter of the Fourier transform pattern 45A of the beam of illuminating light itself and the width of the patternless portion, respectively, shown in FIG. 3C.

Figure 6B:
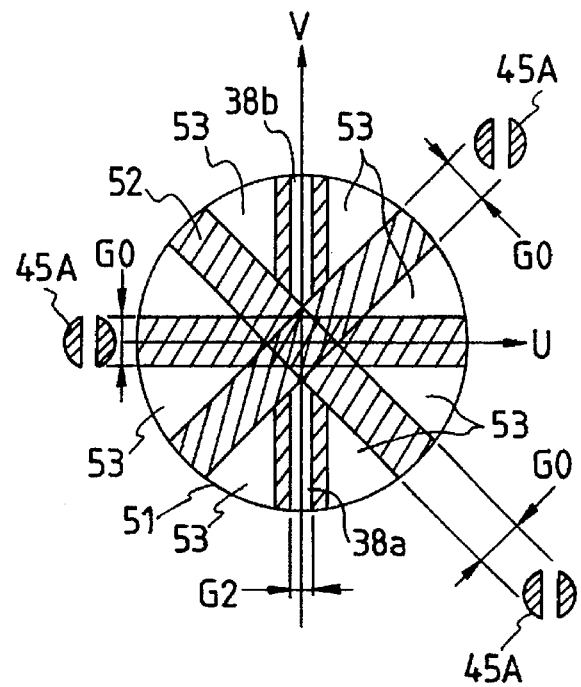
FIG. 6B is a plan view showing a Fourier transform pattern obtained by the mixed pattern of the linear patterns of FIGS. 4A, 4B, 4C and 4D being Fourier-transformed by the optical system of FIG. 3A in the first embodiment.

Likewise, the widths of band-like Fourier transform patterns created when the circuit patterns 48–50 of FIGS. 4B, 4C and 4D in the respective directions are Fourier-transformed by the optical system of FIG. 3A depend on the Fourier transform pattern 45A of the beam of illuminating light itself. To intercept the Fourier transform patterns created by these circuit patterns, the light intercepting member 52 of FIG. 5E will suffice. However, as shown in FIG. 6A, in the Fourier transform pattern 47B, the area of a width G2 on V axis is a patternless portion. Therefore, even if as shown in FIG. 6B, use is made of a light intercepting member in which rectangular areas 38a and 38b of a width G2 on V axis have been eliminated from the light intercepting member 52, the Fourier transform patterns obtained by the circuit patterns 47, 48, 49 and 50 of FIGS. 4A, 4B, 4C and 4D being Fourier-transformed by the optical system of FIG. 3A will not pass. A light intercepting member provided by further simplifying the light intercepting member of FIG. 6B is the light intercepting member 38 of FIG. 6C. This light intercepting member 38 is such that in a transform area 51, light can pass through only rectangular areas 38a and 38b of a width G2 along V axis, and those rectangular areas 38a and 38b are a portion of the patternless area in which the Fourier transform pattern of a defect-free circuit pattern is not present. The light intercepting member 38 is used in the embodiment of FIG. 1A.

Figure 7A:
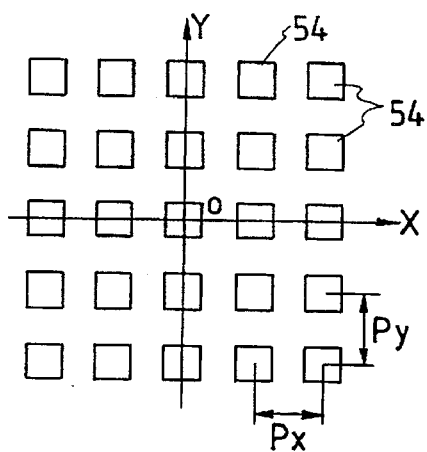
FIGS. 7A, 7B and 7C are plan views showing various two-dimensional periodic patterns on a semiconductive wafer.
Figure 7B:
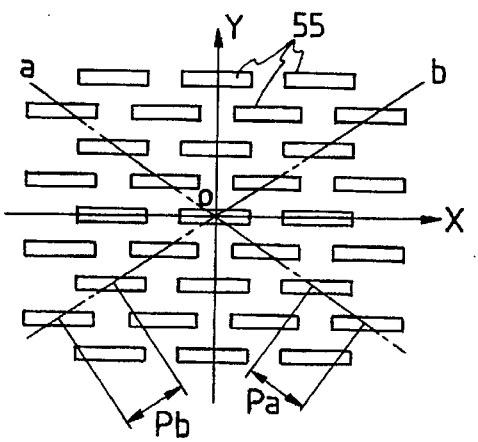
Figure 7C:
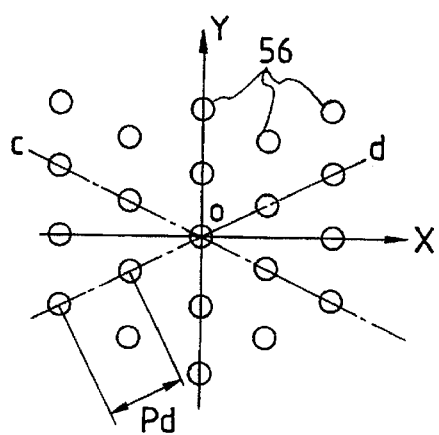

Next, it is to be understood that two-dimensional periodic patterns 54, 55 and 56 shown in FIGS. 7A, 7B and 7C are present in the illuminated area in the die 2 on the semiconductive wafer to be inspected by the optical system of FIG. 3A. That is, the two-dimensional periodic pattern 54 of FIG. 7A is one in which square patterns are arranged at pitches Px and Py in the direction of x axis and the direction of y axis, respectively. The two-dimensional periodic pattern 55 of FIG. 7B is one in which rectangular patterns long in x direction are arranged at pitches Pa and Pb in the direction of a axis and the direction of b axis, respectively. The two-dimensional periodic pattern 56 of FIG. 7C is one in which circular patterns are arranged at a pitch Pd in the direction of c axis and the direction of d axis.

Figure 8A:
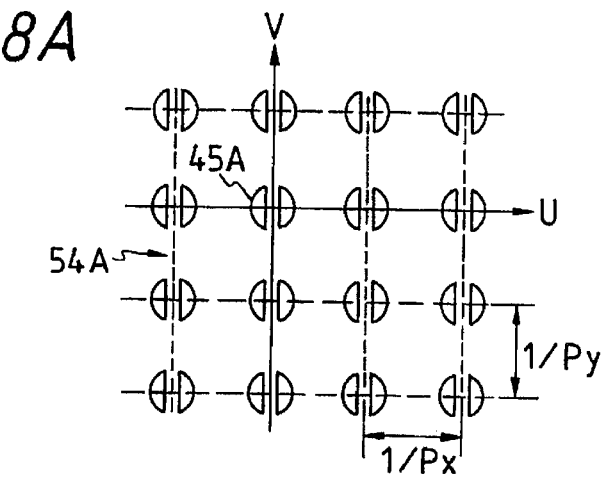
FIGS. 8A, 8B and 8C are plan views showing Fourier transform patterns obtained by the various two-dimensional periodic patterns of FIGS. 7A to 7C being Fourier-transformed by the defect inspecting apparatus of FIG. 1A according to the first embodiment.
Figure 8B:
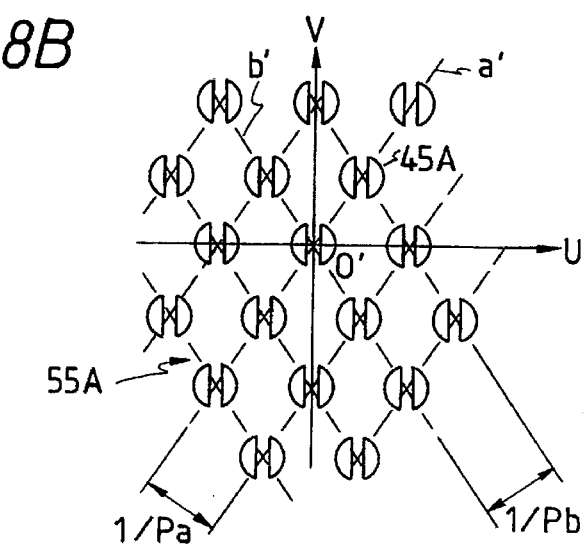
Figure 8C:
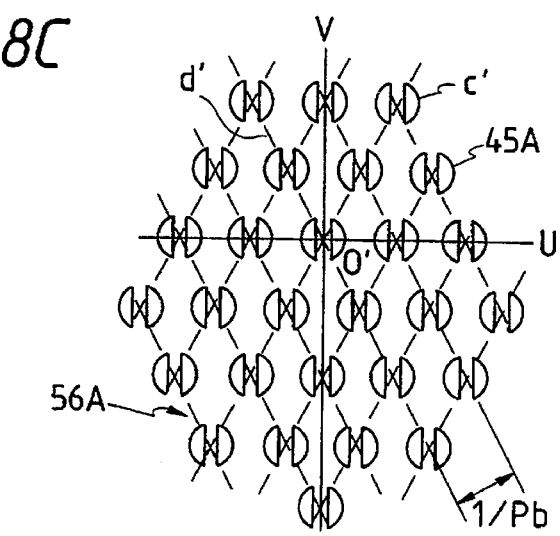

The Fourier transform patterns of the two-dimensional periodic patterns 54, 55 and 56 become the Fourier transform patterns 54A, 55A and 56A of FIGS. 8A, 8B and 8C, respectively. Any of the Fourier transform patterns 54A, 55A and 56A is such that the Fourier transform pattern (Fourier spectrum) 45A of the beam of illuminating light itself is discretely distributed. That is, the Fourier transform pattern 54A is one in which Fourier transform patterns 45A are arranged at pitches 1/Px and 1/Py along U axis and V axis, respectively, the Fourier transform pattern 55A is one in which Fourier transform patterns 45A are arranged at pitches 1/Pb and 1/Pa along a' axis orthogonal to a axis and b' axis orthogonal to b axis, respectively, and the Fourier transform pattern 56A is one in which Fourier transform patterns 45A are arranged at a pitch 1/Pd along c' axis orthogonal to c axis and d' axis orthogonal to d axis.

Figure 6C:
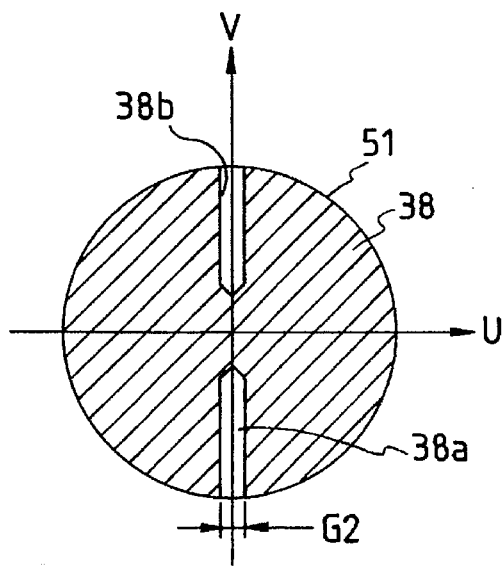
FIG. 6C is a plan view showing a light intercepting member 38 used in the first embodiment.

These Fourier transform patterns 54A, 55A and 56A are such that no Fourier transform pattern is present on and near V axis, but yet exhibit various distributions in the other portion on UV plane. Accordingly, to intercept all of these two-dimensional periodic patterns 54A, 55A and 56A as well, use can be made of a light intercepting member 38 passing therethrough only the light information in areas 38a and 38b of a width G2 along V axis, as shown in FIG. 6C. In the foregoing description, the illuminating light has been described as monochromatic light, but even when the illuminating light is white light or a plurality of monochromatic lights, the light intercepting member 38 of FIG. 6C will operate without any problem in principle.

Now, turning back to FIG. 1A, the same light intercepting member (space filter) 38 as the light intercepting member 38 of FIG. 6C is disposed in the rearward focal plane (Fourier transform plane) 17 of the Fourier transform lens 10. FIG. 1D shows the light intercepting member 38 of FIG. 1A, and the width G1 of two areas 38a and 38b along V axis which are the light transmitting portions of this light intercepting member 38 are made coincident with the width G2 of the light intercepting member 32 of FIG. 1B. Also, an aperture 38c is formed in the central portion of the light intercepting member 38 so that the light intercepting member may not interfere with the vibratory mirror 33.

Almost all of the circuit patterns in the dies on the semiconductive wafer 1 of FIG. 1A are the two-dimensional periodic patterns 47, 48, 49 and 50 of FIGS. 4A, 4B, 4C and 4D or the two-dimensional periodic patterns 54, 55 and 56 of FIGS. 7A, 7B and 7C. Accordingly, the light intercepting member (space filter) 38 can be one which blocks the spatial frequency of the Fourier transform information (errorless Fourier transform information) when there is no error in these circuit patterns, but passes therethrough light created from any defect in the dies on the semiconductive wafer 1. The structure of the light intercepting member 38 of FIG. 1D would satisfy these conditions. A beam of light 39 returned from the semiconductive wafer 1 enters the light intercepting member 38 via the Fourier transform lens 10, but a beam of light (defect carrying beam of light) 40 including a defect information which has not been blocked by the light intercepting member 38 enters the reverse Fourier transform lens 23.

The reverse Fourier transform lens 23 reversely Fourier-transforms the light pattern of the light from the illuminated dies on the semiconductor wafer 1 which has passed through the light intercepting member 38. The reverse Fourier transform lens 23 is disposed at a distance one time as great as the focal length of the lens 23 from the rearward focal plane 17 of the Fourier transform lens 10, and the lenses 10 and 23 are arranged along the same optical axis 24. Also, the light receiving surface of a one-dimensional photodetector array 26 is disposed about the optical axis 24 on the image plane 25 which is the rearward focal plane of the reverse Fourier transform lens 23, and the coordinates axis on the light receiving surface of the photodetector array 26 which is conjugate with the x axis on the semiconductive wafer 1 is defined as x' axis.

As shown in FIG. 1C, each image pickup element 41 of the photodetector array 26 receives the image of a defect present in each die on the semiconductive wafer 1 and produces an image pickup signal. That is, the one-dimensional photodetector array 26 has a plurality of image pickup elements 41 arranged in a one-dimensional direction (x' direction) with substantially the same width as the spot diameter of an image on the image plane 25 conjugate with the spot diameter on the semiconductive wafer 1 at the convergence points 35A, 36A, etc. of the beams of light 35, 36, etc. converged on the semiconductive wafer 1. The number of those image pickup elements 41 is a number great enough to receive all of the linear images 37P of the illuminated area 37 of a length L1 on the semiconductive wafer 1.

Description will now be made of the relative scanning of the illuminated area (inspected area) in each die on the semiconductive wafer 1 of FIG. 1A.

FIG. 1E shows each die 2 on the semiconductive wafer 1. In FIG. 1E, a right lower point in the die 2 is positioned on the optical axis 24 of FIG. 1A, and the vibratory mirror 33 is vibrated and scans on an illuminated area 37-1 by the converged light. Subsequently, the die 2 is moved in y direction by the two-dimensional parallel-moving means 12 to thereby shift the optical axis 24 relatively outwardly, and the vibratory mirror scans on an illuminated area 37-2 by the converged light. In this manner, the scanning by the vibratory mirror 33 and the movement by the two-dimensional parallel-moving means 12 are repeated, whereby scanning is sequentially effected up to a right upper illuminated area 37-n in the die 2 by the converged light, and subsequently the die 2 is moved in x and y directions by the two-dimensional parallel-moving means 12 to thereby position a central lower point in the die 2 on the optical axis 24, and the vibratory mirror scans on an illuminated area 37-(n+1) by the converged light. Thereafter, like the vibratory mirror has previously scanned the illuminated areas 37-1 to 37-n, the vibratory mirror sequentially scans on the illuminated areas 37-(n+1) to 37-m by the converged light. The relative scanning as described above is repeated to thereby relatively scan the whole interior of the die 2 by the converged light, and the images of any defects created during this scanning are received by the image pickup elements 41 of the photodetector array 26. The images of the defects introduced by the image pickup elements 41 are converted into defect signals in the form of electrical signals.

As described above, according to the present embodiment, the angles of incidence of the beams of light 35, 36, etc. as the illuminating light onto the semiconductive wafer 1 are limited by the light intercepting member 32 between the beam expander 4 and the semiconductive wafer 1. Thereby, a spectrum-free area (i.e., an area in which no light component appears when there is no defect in the circuit patterns on the semiconductive wafer 1) is set in the Fourier transform plane 17 of the Fourier transform lens 10.

The light intercepting member 38 passes therethrough the light component in that spectrum-free area and therefore, only the light from a defective pattern on the semiconductive wafer 1 passes through the light intercepting member 38. Accordingly, the photodetector array 26 can receive only the image of the defect.

In the above-described embodiment, the photodetector array 26 is used the photoelectrically convert the image of the defect, but a single light receiving element may be used to simply obtain the signal intensity of the image of the defect. Again in such case, scanning can be effected by the two-dimensional scanning means 12 to thereby find the location of the defect.

A second embodiment of the present invention will now be described with reference to FIG. 9A, etc. The second embodiment is an improvement over the first embodiment of FIG. 1A, and in FIG. 9A, portions corresponding to those in FIG. 1A are given the same reference characters and need not be described in detail.

Figure 9A:
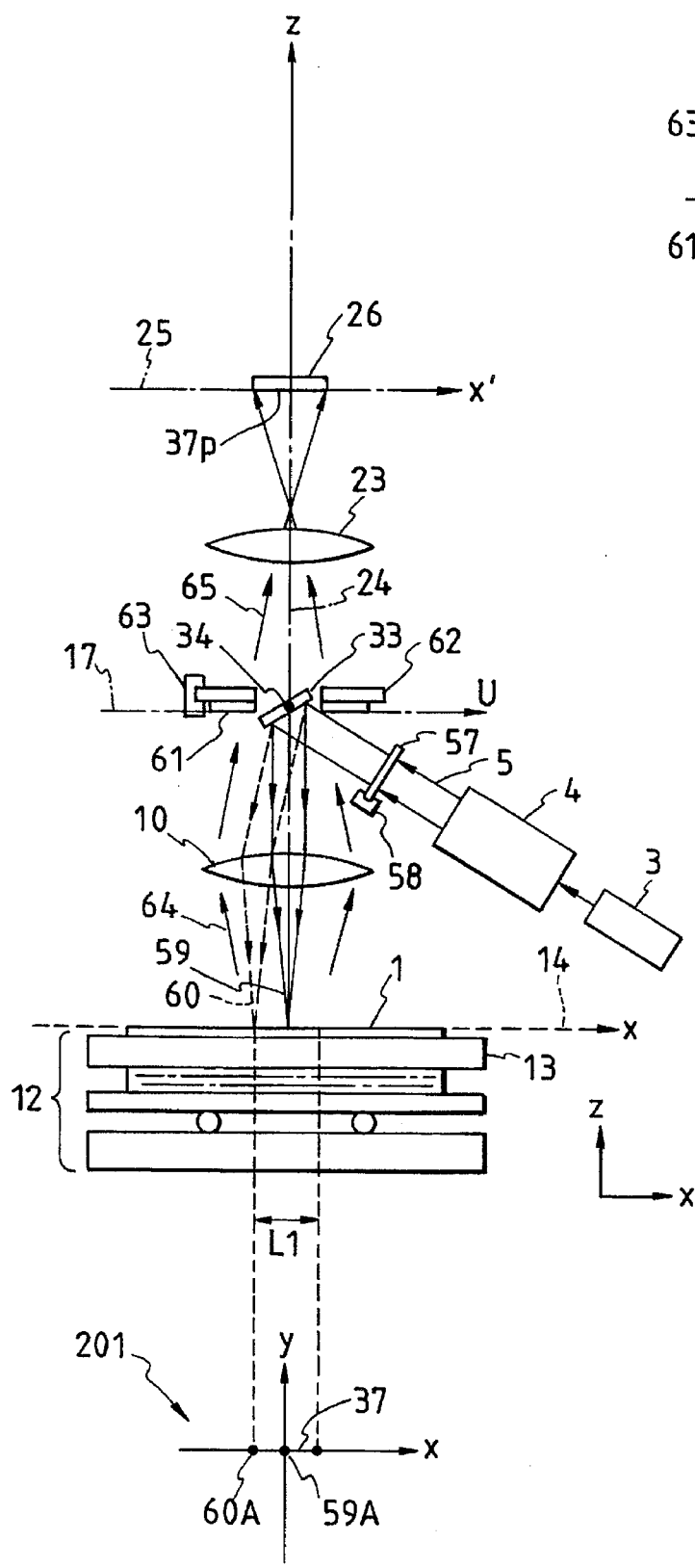
FIG. 9A shows the construction of a defect inspecting apparatus according to a second embodiment of the present invention.

FIG. 9A shows a defect inspecting apparatus according to the present embodiment, and in FIG. 9A, an aperture plate 57 is disposed in the optical path of the beam of light 5 between the beam expander 4 and the vibratory mirror 33. The aperture plate 57 is disposed for rotation about the optical axis of the beam of light 5. A driver 58 is a driving mechanism for rotating the aperture plate 57.

Figure 9C:
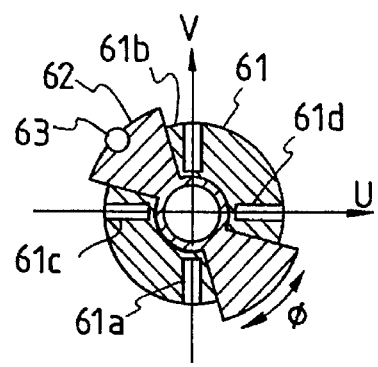
FIG. 9C is a plan view showing a light intercepting member 61 and a shutter 62 in FIG. 9A.
Figure 9B:
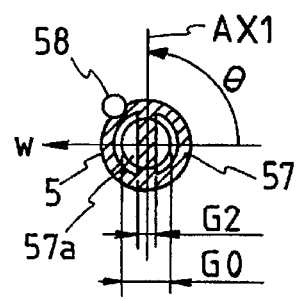
FIG. 9B shows an aperture plate 57 in FIG. 9A as it is seen in the direction of travel of the beam of light 5.

As shown in FIG. 9B, the aperture plate 57 has a rectangular light intercepting portion 57a of a width G2 crossing the center of the beam of light 5 of a diameter G0. The lengthwise direction of the light intercepting portion 57a can be changed over at two stages in a direction parallel to W axis or an axis AX1 perpendicular to this W axis. That is, when the angle formed between the lengthwise direction of the light intercepting portion 57a and W axis is θ, the angle θ can be changed over to 0° or 90° by the driver 58. Accordingly, the beam of light 5 has its area of a width G2 about W axis or the axis AX1 intercepted by the light intercepting portion 57a. The width G2 is about 20% of the diameter G0 of the beam of light 5. W axis is an axis perpendicular to the plane of the drawing sheet of FIG. 9A (xz plane) and crossing the center of the beam of light 5.

In FIG. 9A, the beam of light 5 passed through the aperture plate 57 is reflected by the vibratory mirror 33. The beam of light 5 reflected by the vibratory mirror 33 is converged by the Fourier transform lens 10 and scans on the semiconductive wafer 1 as a beam of light 59 or 60, etc. The beams of light 59, 60, etc. are converged at convergence points 59A, 60A, etc., respectively, on the semiconductive wafer 1, as indicated in the portion 201 of FIG. 9A (which corresponds to the portion 200 of FIG. 1A), and a linear illuminated area 37 of a length L1 is formed by these convergence points.

In FIG. 9A, a beam of light 64 diffracted by the circuit pattern on the semiconductive wafer 1 arrives at the Fourier transform plane 17 via the Fourier transform lens 10, and a circuit pattern and the Fourier transform pattern of a defect are formed on the Fourier transform plane 17. In the present embodiment, a light intercepting member 61 as a space filter is disposed on the Fourier transform plane 17, and a shutter 62 is disposed so as to be in intimate contact with the light intercepting member 61, and a driver 63 for rotating the shutter 62 is disposed.

As shown in FIG. 9C, the light intercepting member 61 is formed at the center thereof with an aperture in which the vibratory mirror 33 is disposed, and two rectangular areas 61a and 61b of a width G2 along V axis and two rectangular areas 61c and 61d of a width G2 along U axis provide opening portions, and the other area of the light intercepting member 61 is a light intercepting portion. Also, the shutter 62 is comprised of an axisymmetric sector-shaped light intercepting pattern coaxial with the light intercepting member 61. The angles of broadening of the two sector-shaped portions of the shutter 62 are smaller than 90°. Accordingly, by the shutter 62 being rotated in φ direction which is the circumferential direction of the light intercepting member 61, one of the two rectangular areas 61a and 61b of the light intercepting member 61 along V axis or the two rectangular areas 61c and 61d along U axis can be shielded from the light.

In the other points, the construction of the present embodiment is similar to the construction of the first embodiment of FIG. 1A and therefore need not be further described. Description will now be described of the relation between the circuit pattern in the die in the illuminated area on the semiconductive wafer 1 in the present embodiment and the created Fourier transform pattern. First, when in FIG. 9B, the angle θ of the aperture plate 57 is 0°, the cross-sectional shape of the beam of light 5 after passed through the aperture plate 57 becomes just the same as the cross-sectional shape of the beam of light 5 after passed through the light intercepting member 32 of FIG. 1A. Accordingly, the Fourier transform pattern created on the Fourier transform plane 17 of FIG. 9A becomes just the same as that by the first embodiment.

Figure 10A:
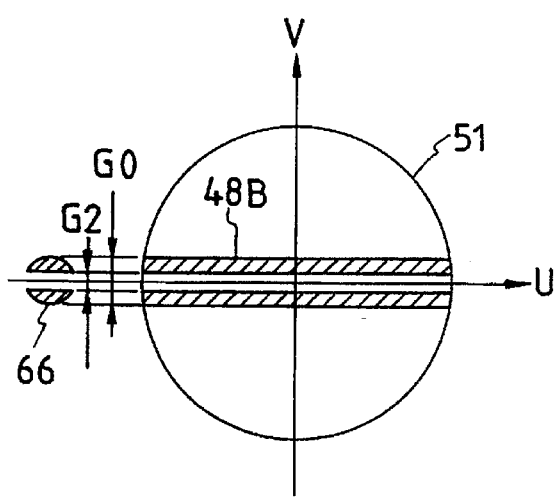
FIG. 10A is a plan view showing a Fourier transform pattern obtained by the linear pattern of FIG. 4B being Fourier-transformed by the optical system in the second embodiment.
Figure 10B:
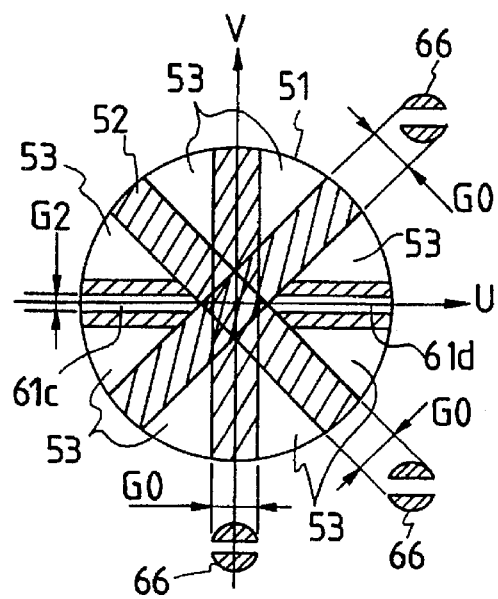
FIG. 10B is a plan view showing a Fourier transform pattern obtained by the mixed pattern of the linear patterns of FIGS. 4A, 4B, 4C and 4D being Fourier-transformed by the optical system in the second embodiment.
Figure 10C:
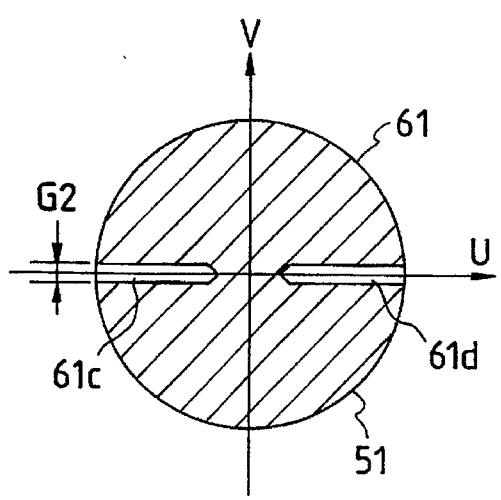
FIG. 10C is a plan view showing a light intercepting member 61 used in the second embodiment.
Figure 10D:
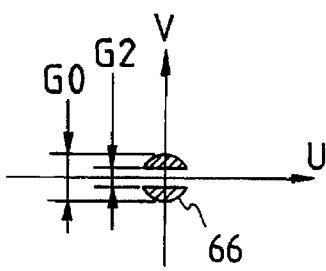
FIG. 10D shows a Fourier transform pattern obtained by an incident beam of light itself in the second embodiment being Fourier-transformed.

In contrast, when in FIG. 9B, the angle θ of the aperture plate 57 is 90°, the Fourier transform pattern of the incident beam of light itself created when there is no pattern on the semiconductive wafer 1 becomes like the Fourier transform pattern 66 of FIG. 10D. Accordingly, the Fourier transform pattern created when the circuit pattern 48 of FIG. 4B is in the illuminated area of the semiconductive wafer 1 of FIG. 9A becomes like the Fourier transform pattern 48B of FIG. 10A along U axis. In FIG. 10A, the transform area 51 shows a limit area in the spatial frequency area determined by the Fourier transform lens 10 of FIG. 9A, and the width G0 of the whole of the Fourier transform pattern 48B and the width G2 of the central patternless area depend on the Fourier transform pattern 66 of the beam of illuminating light itself shown in FIG. 10D.

Likewise, the widths of band-like Fourier transform patterns created by the circuit patterns of FIGS. 4A, 4C and 4D in respective directions also depend on the Fourier transform pattern 66 of the beam of illuminating light itself. To intercept the Fourier transform patterns of these circuit patterns, the light intercepting member 52 of FIG. 5E will suffice. However, as regards areas 61c and 61d of a width G2 on the U axis of FIG. 10B, the Fourier transform patterns of the circuit patterns will not pass even if the light intercepting member is absent.

Figure 11A:
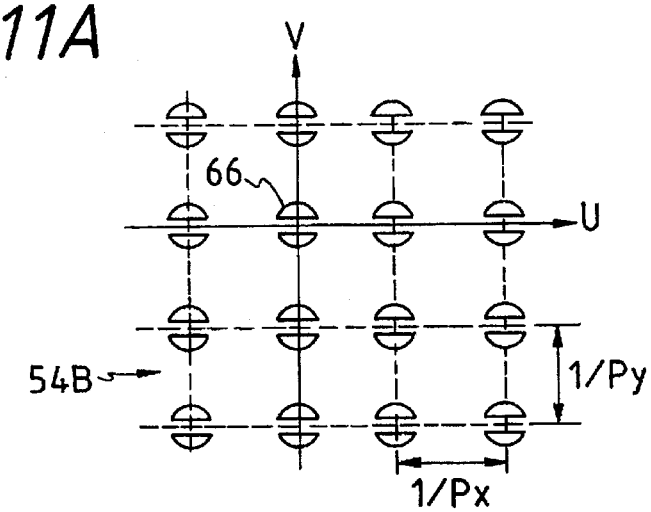
FIGS. 11A, 11B and 11C are plan views showing Fourier transform patterns obtained by the various two-dimensional periodic patterns of FIGS. 7A, 7B and 7C being Fourier-transformed by the defect inspecting apparatus according to the second embodiment.
Figure 11B:
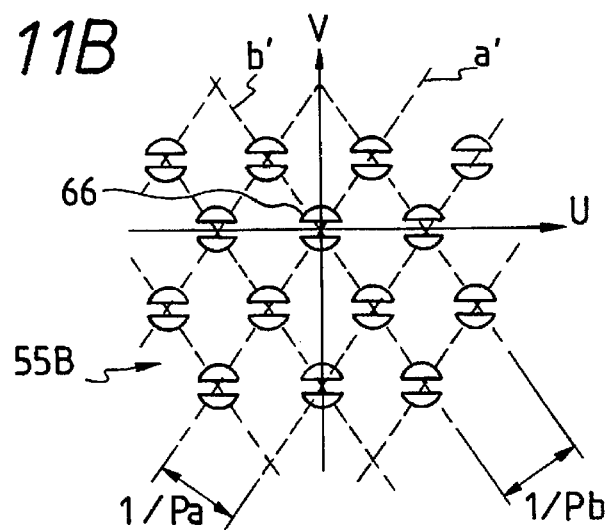
Figure 11C:
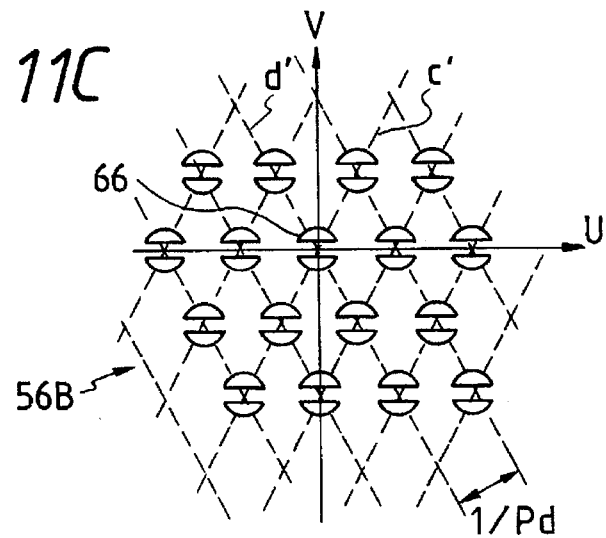

Also, when two-dimensional periodic patterns 54, 55 and 56 shown in FIGS. 7A, 7B and 7C exist in the illuminated area in the die on the semiconductive wafer 1 of FIG. 9A, the Fourier transform patterns thereof become like the Fourier transform patterns 54B, 55B and 56B of FIGS. 11A, 11B and 11C, respectively. These Fourier transform patterns 54B, 55B and 56B are ones in which the Fourier transform patterns 66 of the beam of illuminating light itself are regularly and discretely arranged. The Fourier transform patterns 54B, 55B and 56B of FIGS. 11A, 11B and 11C do not exist on and near U axis, but yet exhibit various distributions with respect to the other portions on UV plane. Accordingly, to intercept the Fourier transform patterns 54B, 55B and 56B of these two-dimensional periodic patterns as well, use can be made of a light intercepting member 61 passing therethrough light information in areas 61c and 61d of a width G2 as shown in FIG. 10C. This light intercepting member 61 of FIG. 10C is equivalent to the areas 61a and 61b of the light intercepting member 61 of FIG. 9C which are covered with the shutter 62.

Accordingly, in the present embodiment, the angle θ of the aperture plate 57 of FIG. 9B can be selected to one of 0° and 90°, and the light distributions of the Fourier transform patterns produced on the Fourier transform plane 17 by such selection differ. To detect a defect alone, when the angle θ of the aperture plate 57 of FIG. 9B is selected to 0°, it is necessary in FIG. 9C to drive the shutter 62 by the driver 63 to thereby cover the two areas 61c and 61d of the light intercepting member 61 along U axis. Also, when the angle θ of the aperture plate 57 is selected to 90°, it is necessary in FIG. 9C to drive the shutter 62 by the driver 63 to thereby cover the two areas 61a and 61b of the light intercepting member 61 along V axis. Also, again in the present embodiment, as in the first embodiment, the illuminating light may be either monochromatic light or white light without any inconvenience.

Figure 12A:
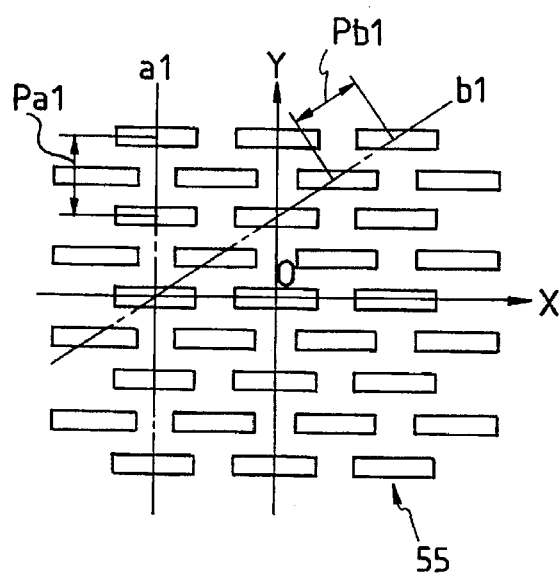
FIG. 12A shows the two-dimensional periodic pattern of FIG. 7B as it is seen from another point of view.

Also, the circuit pattern 55 shown in FIG. 7B, when considering the central point of each pattern, is regarded as being comprised of two periodic point trains a1 and b1 of pitches Pa1 and Pb1, respectively, as shown in FIG. 12A. The direction of the periodic point train a1 is perpendicular to x axis, and the Fourier transform pattern of the periodic point train a1 becomes the periodic line train a1' of FIG. 12B, the direction of which is parallel to U axis. Also, the Fourier transform pattern of the periodic point train b1 of FIG. 12A becomes the periodic line train b1' of FIG. 12B, the direction of which is perpendicular to the direction of the periodic point train b1. After all, the created Fourier transform patterns are ones in which the Fourier transform patterns 66 of the beam of illuminating light itself are arranged on the lattice points of the periodic line trains a1' and b1'. However, this is in the case where the angle θ of the aperture plate 57 of FIG. 9B is 0°.

Figure 13A:
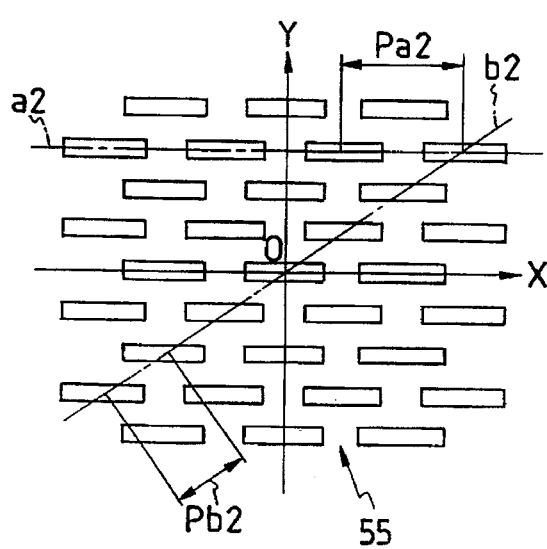
FIG. 13A shows the two-dimensional periodic pattern of FIG. 7B as it is seen from still another point of view.

Also, the circuit pattern 55 of FIG. 7B, when considering the central point of each pattern, is regarded as being comprised of two periodic point trains a2 and b2 of pitches Pa2 and Pb2, respectively, as shown in FIG. 13A. The periodic point train a2 is parallel to y axis, and the Fourier transform pattern of the periodic point train a2 becomes the periodic line train a2' of FIG. 13B parallel to V axis. Also, the Fourier transform pattern of the periodic point train b2 is the periodic line train b2' of FIG. 13B, the direction of which is perpendicular to the direction of the periodic point train b2. Accordingly, the created Fourier transform patterns are ones in which the Fourier transform patterns 45A of the beam of illuminating light itself are arranged on the lattice points of the periodic line trains a2' and b2'. However, this is in the case where the angle θ of the aperture plate 57 of FIG. 9B is 90°.

Figure 12B:
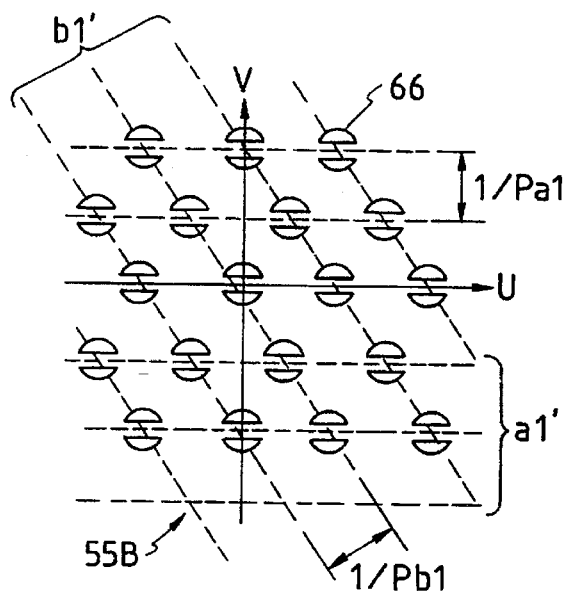
FIG. 12B shows a Fourier transform pattern according to the second embodiment of FIG. 12A.
Figure 13B:
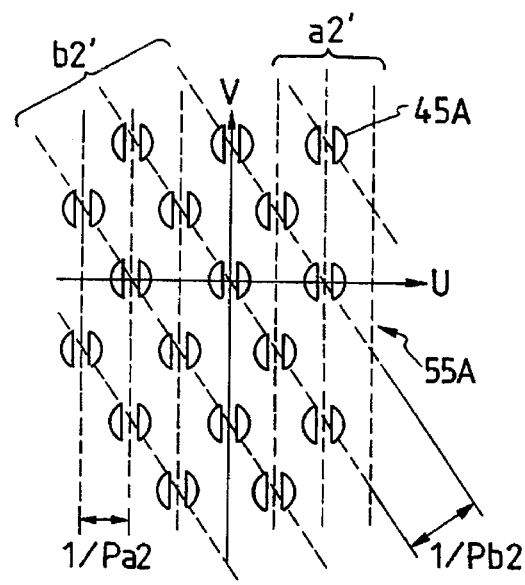
FIG. 13B shows a Fourier transform pattern according to the second embodiment of FIG. 13A.

FIG. 8B and FIG. 13B are just the same, and FIG. 11B and FIG. 12B are just the same. As regards an ordinary two-dimensional periodic pattern, when it is decomposed into two periodic point trains, at least one of them is parallel to x direction or y direction. Accordingly, a Fourier transform pattern created becomes parallel to U direction or V direction. For such a Fourier transform pattern, the angle θ of the aperture plate 57 of FIG. 9B is selected to 0° or 90° whereby an area in which no Fourier transform pattern will be created can be formed in the area of a width G2 on U axis or V axis. The present embodiment is suitable for inspecting the defects of ordinary circuit patterns.

Figure 14A:
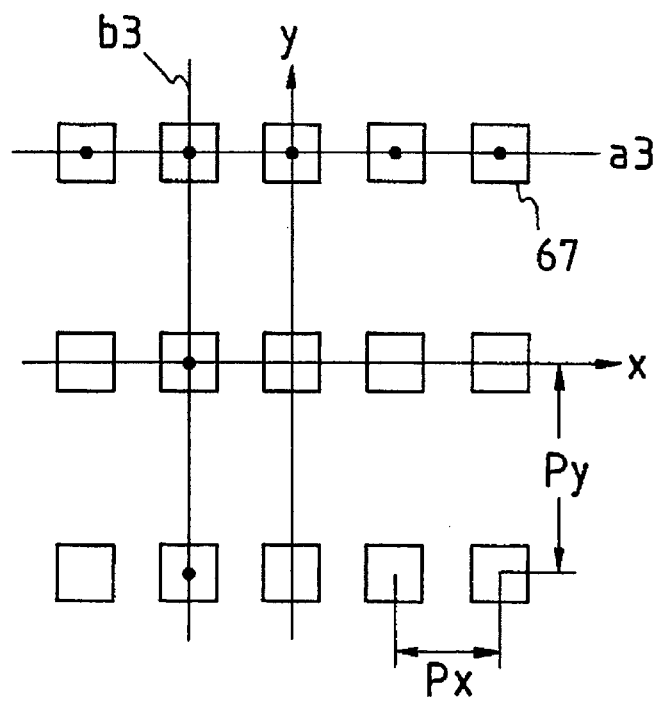
FIG. 14A is a plan view showing another example of the two-dimensional periodic pattern.
Figure 14B:
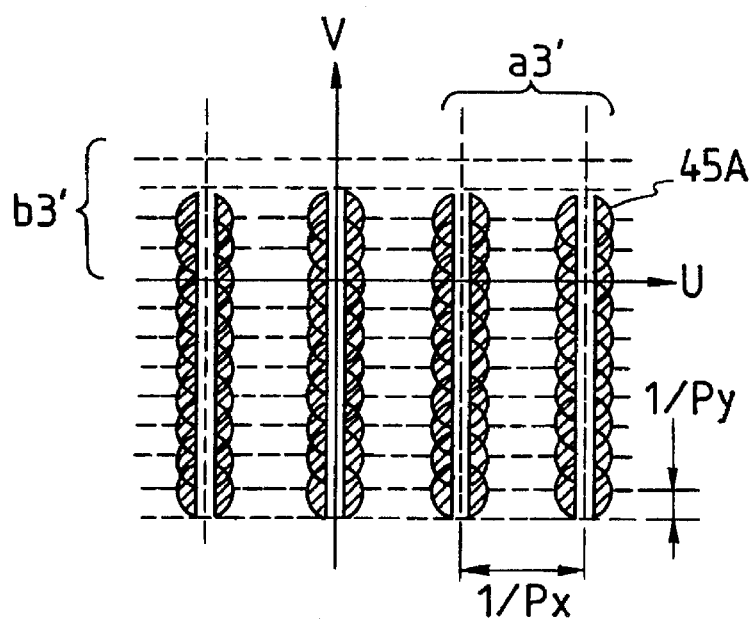
FIG. 14B is a plan view showing a Fourier transform pattern according to the second embodiment of FIG. 14A.

Also, the present embodiment is suitable for detecting the defect of a circuit pattern as shown in FIG. 14A. The circuit pattern of FIG. 14A comprises square patterns 67 arranged at pitches Px and Py (Py>Px) in x direction and y direction, respectively. When the circuit pattern of FIG. 14A is decomposed into two periodic point trains a3 and b3, these are parallel to x direction and y direction, respectively. However, the pitch Py of the periodic point train b3 is relatively great and therefore, the Fourier transform pattern thereof, as shown in FIG. 14B, is comprised of a periodic line train b3' of a pitch 1/Py small in V direction and a periodic line train a3' of a pitch 1/Px in U direction. FIG. 14B shows the Fourier transform pattern when the angle θ of the aperture plate 57 of FIG. 9B is selected to 90°. The pitch 1/Py is small as compared with the pitch 1/Px and therefore, the Fourier transform pattern of FIG. 14B ranges in V direction. Therefore, when the pitch 1/Py becomes small to a certain degree, even if the angle θ of the aperture plate 57 of FIG. 9B is selected to 0°, there may be a case where the area in which no Fourier transform pattern is created on or near U axis is lost. In the present embodiment, even in such a case, the optimum direction within 90° or 0° as the angle θ can be selected.

Turning back to FIG. 9A, almost all of the circuit patterns in the dies on the semiconductive wafer 1 are circuit patterns shown in FIGS. 4A, 4B, 4C and 4D or FIGS. 7A, 7B and 7C. Therefore, the light intercepting member 61 and shutter 62 block the spatial frequency component of the errorless Fourier transform information, but pass therethrough the light created from the defects in the dies. The defect carrying beam of light 65 which has not been blocked by the light intercepting member 61 and shutter 62 enters the reverse Fourier transform lens 23. The light receiving surface of the photodetector array 26 is disposed on the image plane 25 of the reverse Fourier transform lens 23, and as in FIG. 1C, the conjugate image 37P of the defect in the illuminated area 37 on the semiconductive wafer 1 is formed on the light receiving surface of the photodetector array 26. Also, as in FIG. 1E, the illuminated area 37 and the dies 2 on the semiconductive wafer 1 are scanned relative to each other, whereby the detection of the defect on the whole surface of the dies 2 is effected as in the first embodiment.

A third embodiment of the present invention will now be described with reference to FIG. 15A, etc. This embodiment is an improvement over the second embodiment, and in FIG. 15A, portions corresponding to those in FIG. 9 are given the same reference numerals and need not be described in detail.

Figure 15A:
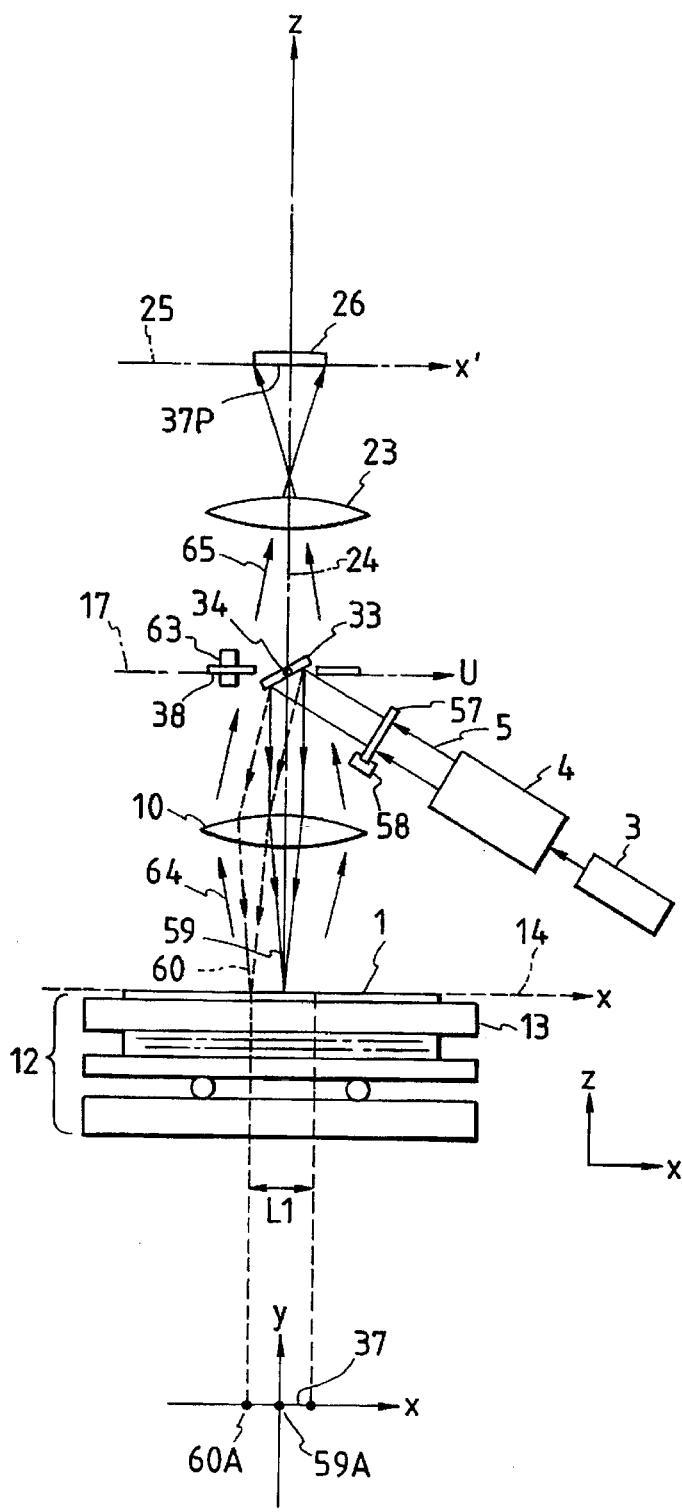
FIG. 15A shows the construction of a third embodiment of the present invention.
Figure 15C:
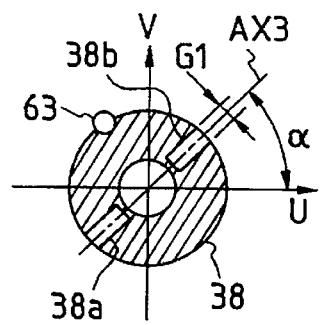
FIG. 15C is a plan view showing a light intercepting member 38 in the third embodiment.
Figure 15B:
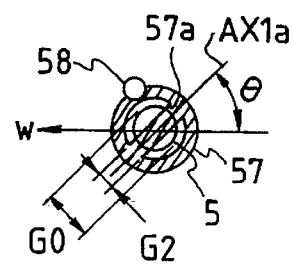
FIG. 15B shows an aperture plate 57 in the third embodiment as it is seen in the direction of travel of the beam of light 5.

FIG. 15A shows a defect inspecting apparatus according to the present embodiment, and in FIG. 15A, an aperture plate 57 is disposed in the optical path of the beam of light 5 between the beam expander 4 and the vibratory mirror 33, and this aperture plate 57 is supported for rotation about the optical axis of the beam of light 5. The angle of rotation of the aperture plate 57 is set by a driver 58. When an axis passing through the center of the beam of light 5 and perpendicular to the plane of the drawing sheet of FIG. 15A (xz plane) is defined as W axis, as shown in FIG. 15B, the aperture plate 57 is a zonal light intercepting member having an inner diameter larger than the outer diameter G0 of the beam of light 5 and provided with a light intercepting portion 57a of a width G2 so as to pass through the center of the aperture plate 57 (with the zonal light intercepting portion and the light intercepting portion 57a being made coaxial with each other). When an axis AX1a is plotted along the lengthwise direction of the light intercepting portion 57a, the angle θ formed between the negative direction of W axis and the axis AX1a can be set to any angle by the driver 58. Accordingly, the beam of light 5 having an outer diameter G0 has its area of a width G2 about the axis AX1a intercepted by the aperture plate 57. The width G2 is about 20% of the outer diameter G0 of the beam of light 5. Turning back to FIG. 15A, in the present embodiment, only a light intercepting member 38 and a driver 63 are disposed around the vibratory mirror 33 on the Fourier transform plane 17 of the Fourier transform lens 10. The light intercepting member 38 in the present embodiment, as shown in FIG. 15C, is formed with an aperture for the vibratory mirror 33 at the center thereof and only two areas 38a and 38b of a width G1 disposed so as to be opposed to each other provide light transmitting portions (opening portions). When an axis passing through the centers of these areas 38a and 38b through which light passes is defined as an axis AX3, the angle α formed between U axis and the axis AX3 can be set to any angle by the driver 63. In the other points, the construction of the present embodiment is the same as the construction of the embodiment of FIG. 9A and therefore need not be described. Also, it is to be understood that x axis and y axis which are the orthogonal axes on the surface of the semiconductive wafer 1 of FIG. 15A, i.e., the object plane of the Fourier transform lens 10, are parallel to the reference orthogonal axes during the depiction of circuit patterns and the origins of x axis and y axis lie on the optical axis 24.

Figure 15D:
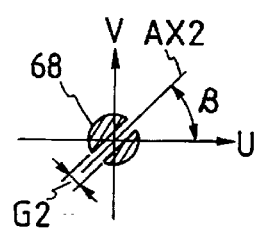
FIG. 15D is a plan view showing a Fourier transform pattern obtained by an incident beam of light in the third embodiment being intactly Fourier-transformed.

In the present embodiment, when a semiconductive wafer having no pattern thereon is placed in lieu of the semiconductive wafer 1, the Fourier transform pattern obtained on the Fourier transform plane 17 depends on the angle θ of the axis AX1a of the aperture plate 57 of FIG. 15B. That is, the Fourier transform pattern 68 on the Fourier transform plane 17 of the incident beam of light itself when the semiconductive wafer having no pattern thereon is placed is such that as shown in FIG. 15D, the area of a width G2 about an axis AX2 passing through the origin in a circular pattern is a patternless area. The angle β formed by the axis AX2 of the Fourier transform pattern 68 with respect to U axis becomes equal to the angle θ formed by the axis AX1a of the aperture plate 57 of FIG. 15B with respect to the negative direction of W axis.

Accordingly, in the present embodiment, as shown in FIG. 15D, the area of a width G2 along the axis AX2 of the Fourier transform pattern 68 is a patternless area. So, it is necessary for the light intercepting member 38 of FIG. 15C to pass therethrough only the beam of light in that patternless area and therefore, the angle α of the axis AX3 of the light intercepting member 38 is always made equal to the angle β of the axis AX2 of the Fourier transform pattern 68 of FIG. 15D, i.e., the angle θ of the axis AX1 of the aperture plate 57 of FIG. 15B. For this purpose, the drivers 58 and 63 can be operated in synchronism with each other.

Assuming that usually the angle θ of FIG. 15B is set to 0° or 90°, the apparatus of this third embodiment performs the same operation as the apparatus of the second embodiment shown in FIG. 9A. Further, in the present embodiment, the angle θ can be set to any other value and therefore, the present embodiment can also be applied to a two-dimensional periodic circuit pattern as shown in FIG. 16A.

Figure 16A:
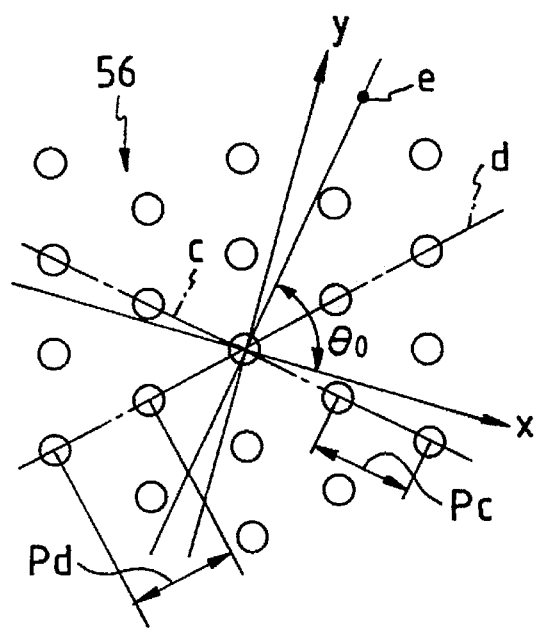
FIG. 16A is a plan view showing an example of the two-dimensional periodic pattern.

The two-dimensional periodic pattern 56 shown in FIG. 16A is such that when the central point of each circular pattern is decomposed into two periodic point trains c and d of pitches Pc and Pd, respectively, neither of the periodic point trains c and d is parallel to x axis or y axis. The Fourier transform pattern of the periodic point train c of FIG. 16A becomes the periodic line train c' of FIG. 16B. This periodic line train c' comprises a group of straight lines perpendicular to the periodic direction of the periodic point train c, and the pitch among these straight lines is 1/Pc. Also, the Fourier transform pattern of the periodic line train d becomes the periodic line train d' of FIG. 16B, which comprises a group of straight lines perpendicular to the periodic direction of the periodic point train d, and the pitch among these straight lines is 1/Pd.

Figure 16B:
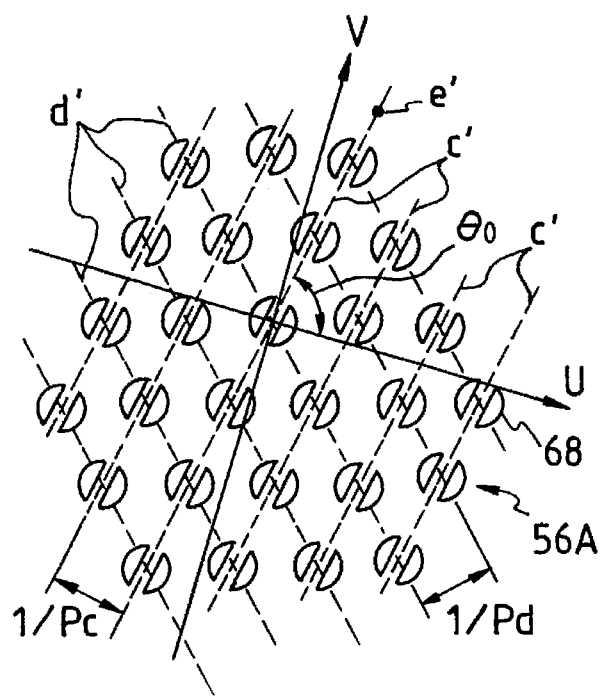
FIG. 16B is a plan view showing the Fourier transform pattern of the pattern of FIG. 16A by the third embodiment.

In this case, according to the present embodiment, the lengthwise direction of the patternless area of the Fourier transform pattern of the beam of illuminating light and the lengthwise direction of the areas 38a and 38b of the light intercepting member 38 of FIG. 15C as the space filter through which the light passes are made coincident with a direction perpendicular to one of the periodic directions of the two periodic point trains c and d of the two-dimensional periodic pattern 56 shown in FIG. 16A. That is, when in FIG. 16A, the angle formed by an axis e perpendicular to the direction of the periodic point train c with respect to x axis is $\theta_0$, the angle formed by the lengthwise direction of the patternless area of the Fourier transform pattern 68 of the beam of illuminating light itself with respect to U axis is also $\theta_0$, as shown in FIG. 16B, and the direction of the patternless area is coincident with the lengthwise direction of the areas 38a and 38b of the light intercepting member 38 of FIG. 15C through which the light passes.

As described above, according to the present embodiment, whatever direction may be the periodic direction of the circuit pattern, the angle of the aperture plate 57 of FIG. 15A and the angle of the light intercepting member 38 are adjusted in conformity therewith, whereby only the defect information on the semiconductive wafer 1 can always be extracted.

A fourth embodiment of the present invention will now be described with reference to FIG. 17A, etc. This embodiment, like the first embodiment, is one in which the present invention is applied to a defect inspecting apparatus for detecting any defect on a semiconductive wafer, and in the present embodiment, portions corresponding to those in FIGS. 1A, 6A, etc. are given the same reference numerals and need not be described in detail.

FIG. 17A is a side view of a defect inspecting apparatus according to the present embodiment. The portion 202 of FIG. 17A shows the construction of an illuminating system in a plane containing the optical axis of the illuminating system of FIG. 17A and x axis (corresponds to an illuminated area L1 as it is seen from Z direction). In the portion 202 of FIG. 17A, a substantially parallel beam of light 5 of a diameter G0 comprising monochromatic light emitted from a beam expander, not shown, enters a rectangular light intercepting member 32 of a width G2. The shape of the light intercepting member 32 is similar to that shown in FIG. 1B, and the beam of light 5 has its area of a width G2 about W axis intercepted. The beam of light 5 passed through the light intercepting member 32 is reflected by the vibratory mirror 33 located near the entrance pupil of a scanning lens 70, and the beam of light 69 reflected by the vibratory mirror 33 becomes a convergent beam of light 71 by the scanning lens 70. The convergent beam of light 71 forms a beam spot on the point of intersection between the surface of the semiconductive wafer 1 and the optical axis 4a of the illuminating system. By the cooperative operation of the vibratory mirror 33 and scanning lens 2, the convergent beam of light 71 becomes, for example, a convergent beam of light 72, and the beam spot thereof can move on a linear illuminated area 37 of a length L1 on the surface of the semiconductive wafer 1. The lengthwise direction of this illuminated area 37 is coincident with x direction perpendicular to the plane of the drawing sheet of FIG. 17A. Also, the scanning lens 70 is a telecentric scan lens, and the optical axis of the convergent beam of light enters always perpendicularly to x axis as long as the beam spot moves from one end point to the other end point on the illuminated area 37.

Further, the direction of the light intercepting member 32 is determined so that for example, in the cross-section of the convergent beam of light 71, the lengthwise direction of the area intercepted by the light intercepting member 32 may always be perpendicular to x axis. Therefore, in the present embodiment, W axis which is the lengthwise direction of the light intercepting member 32 is perpendicular to a plane containing x axis and the optical axis 4a of the scanning lens 70. Also, x axis is parallel to one of the axes of the reference orthogonal coordinates during the depiction of circuit patterns formed on the semiconductive wafer 1. The optical axis 4a of the illuminating system obliquely enters the surface of the semiconductive wafer 1. Also, the center of the illuminated area 37 on the semiconductive wafer 1 is located on the optical axis 24 of the Fourier transform lens 10, and the optical axis 24 coincides with z axis. The object plane (forward focal plane) of the Fourier transform lens 10 is xy plane, on which the illuminated area 37 is located. A beam of light 74 diffracted by the circuit pattern included in the illuminated area 37 of the semiconductive wafer 1 passes through the Fourier transform lens 10 to the Fourier transform plane (rearward focal plane) 17, in which a Fourier transform pattern is formed.

In the present embodiment, the optical axis 4a of the illuminating optical system intersects z axis at an angle M. Therefore, the area of the Fourier transform pattern observed in the Fourier transform plane 17 of the Fourier transform lens 10 deviates by $V_0$ (=$fm_0$=fin M) (see equation (6)) along V axis, relative to the area of the Fourier transform pattern observed in the Fourier transform plane in the first embodiment of FIG. 1A. So, in the present embodiment, a light intercepting member 73 shown in FIG. 17B which is simpler than that in the first embodiment is used as a space filter on the Fourier transform plane 17. In the light intercepting member 73, an area 73a of a width G1 along V axis is a light passing area.

Figure 18A:
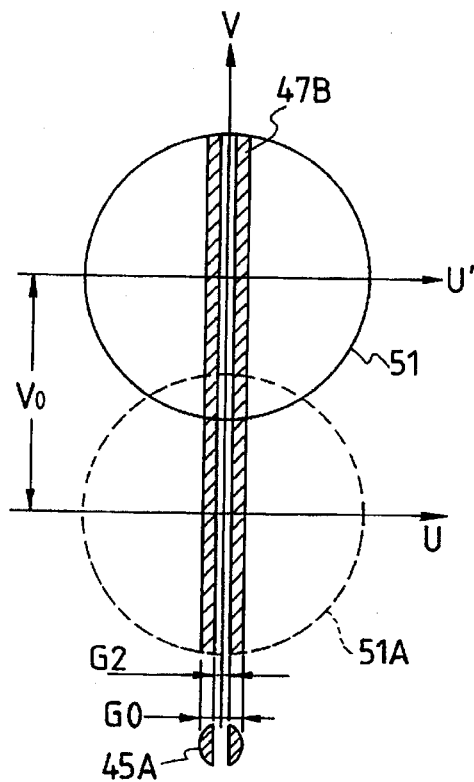
FIG. 18A is a plan view showing a Fourier transform pattern obtained by the linear pattern of FIG. 4A being Fourier-transformed by the optical system in the fourth embodiment.
Figure 18B:
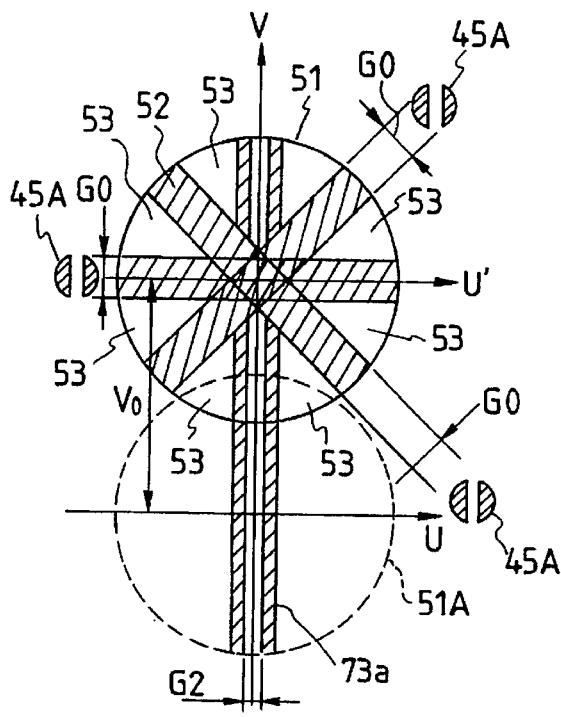
FIG. 18B is a plan view showing a Fourier transform pattern obtained by the mixed pattern of the linear patterns of FIGS. 4A, 4B, 4C and 4D being Fourier-transformed by the optical system in the fourth embodiment.

This will now be described in detail. When the circuit pattern 47 shown in FIG. 4A is present in the illuminating area 37 of the illuminating system in the present embodiment, the Fourier transform pattern observed in the Fourier transform plane 17 is the Fourier transform pattern 47B of FIG. 18A. FIG. 18A corresponds to FIG. 6A for the first embodiment. In the first embodiment, the interior of the transform area 51 around the point of intersection between the V axis and U' axis of FIG. 18A has been observable, while in the present embodiment, the optical axis 4a of the illuminating system obliquely enters the semiconductive wafer 1 and thus, in FIG. 18A, the interior of a transform area 51A around the point of intersection between U axis shifted by $V_0$ along V axis and V axis is observed. The point of intersection between V axis and U' axis indicates the direction of 0-order diffracted light or regularly reflected light.

Where the circuit patterns 48–50 of FIGS. 4B, 4C and 4D in various directions are formed on the semiconductive wafer 1 in the present embodiment of FIG. 17A, the Fourier transform pattern created on the Fourier transform plane 17 is the Fourier transform pattern of FIG. 18B. In the first embodiment, the interior of the transform area 51 has been observed, while in the present embodiment, the interior of the transform area 51A shifted by $V_0$ due to oblique incidence is observed and therefore, only two band-like patterns spaced apart by an area 73a of a width G2 near V axis are observed. The Fourier transform pattern in this transform area 51A is the same as the Fourier transform pattern 47B of FIG. 18A.

Figure 19A:
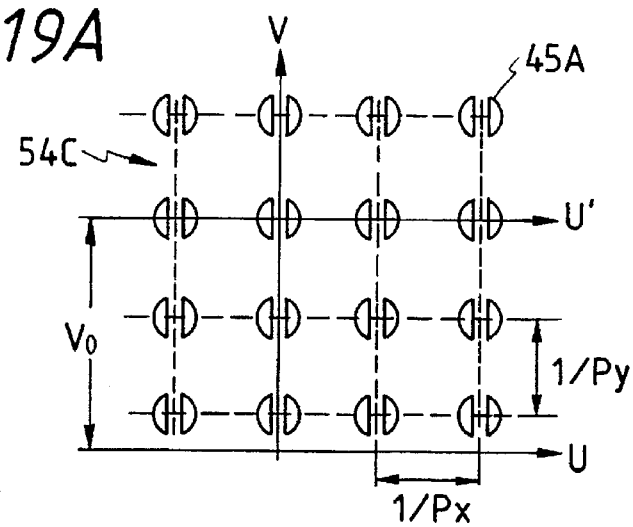
FIGS. 19A, 19B and 19C are plan views showing Fourier transform patterns obtained by the various two-dimensional periodic patterns of FIGS. 7A, 7B and 7C being Fourier-transformed by the defect inspecting apparatus according to the fourth embodiment.
Figure 19B:
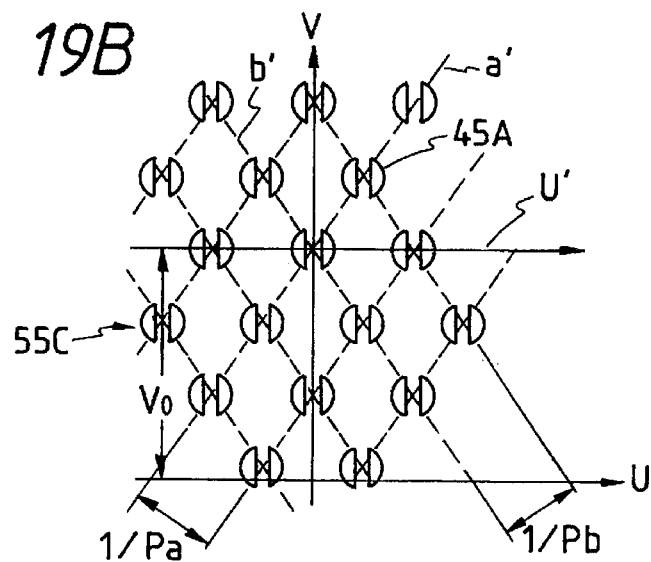
Figure 19C:
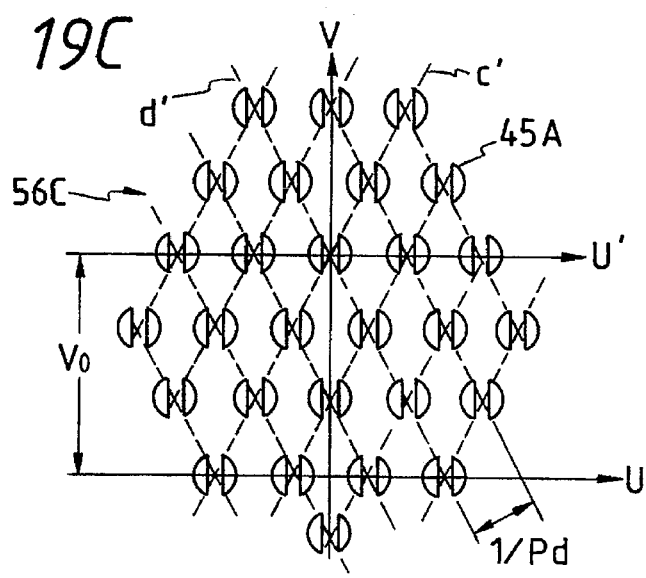

Likewise, where the two-dimensional periodic patterns 54 shown in FIGS. 7A, 7B and 7C are formed on the semiconductive wafer 1 of FIG. 17A, patterns created on the Fourier transform plane 17 are Fourier transform patterns 54C, 55C and 56C shown in FIGS. 19A, 19B and 19C, respectively. With regard also to these Fourier transform patterns 54C, 55C and 56C, observation is effected in an area shifted by $V_0$ with respect to V axis. FIGS. 19A, 19B and 19C correspond to FIGS. 8A, 8B and 8C, respectively. Also, the points of intersection between V axis and U axis shown in FIGS. 19A, 19B and 19C indicate the direction of 0-order diffracted light.

To intercept all of the above-described Fourier transform patterns and permit the light in the patternless area to pass, use can be made of a light intercepting member 73 as a space filter shown in FIG. 18B. The light intercepting member 73 may be of a shape in which the light transmitting area 38a of a width G2 of the light intercepting member 38 used in the first embodiment is extended along V axis. That is, in the light intercepting member 73, a light transmitting area 73a of a width G2 is formed along V axis and the other area is a light intercepting portion, and the light intercepting member 73 is disposed on the Fourier transform plane 17 of FIG. 17A.

Again in the present embodiment, not only monochromatic light but also white light or a combination of a plurality of monochromatic lights may be used as the illuminating light without any problem in principle.

From the foregoing description, the width G1 of the area 73a of the light intercepting member 73 of FIG. 17B which passes the light therethrough is made coincident with the width G2 of the patternless area of the Fourier transform pattern observed. For this purpose, the circuit pattern 47 of FIG. 4A may be formed on the semiconductive wafer 1 and the width of the patternless area of the Fourier transform pattern formed on the Fourier transform plane 17 may be actually measured. Alternatively, from the definition expression of the spatial frequency comprising equations (3) and (4), the width of the u component of the spatial frequency of the gap portion of the incident beam of light 69 can be made coincident with the width of the u component of the spatial frequency corresponding to the width G in U direction on the rearward focal plane 17 of the Fourier transform lens 10 to thereby determine the width G1 of the area 73a of the light intercepting member 73.

In FIG. 17A, the light intercepting member 73 as a space filter blocks the spatial frequency of errorless Fourier transform information, but passes therethrough the light created from the defects in the dies on the semiconductive wafer 1. The beam of light 75 carrying the defect information which has not been blocked by the light intercepting member 73 enters the reverse Fourier transform lens 23. The arrangement relationship between the Fourier transform lens 10 and the reverse Fourier transform lens 23 is similar to that in the first embodiment, and the image of the defect is formed on the image plane (rearward focal plane) 25 of the reverse Fourier transform lens 23. The light receiving surface of the one-dimensional photodetector array 26 is disposed on this image plane 25, and as shown in FIG. 17A, the series of image pickup elements 41 of the photodetector array 26 photoelectrically convert the image 37P of the defect in the illuminated area 37. The illuminated area 37 is moved on the semiconductive wafer 1 by the use of the two-dimensional parallel-moving means 12, whereby the detection of any defect on the whole surface of each die on the semiconductive wafer 1 is effected.

As described above, according to the present embodiment, the condensed beam of light from the illuminating system obliquely impinges on the semiconductive wafer 1 and therefore, as shown, for example, in FIG. 18A, the beam of defect carrying light of the patternless area of a width G2 is detected in the transform area 51A far from 0-order diffracted light which is the point of intersection between U' axis and V axis. Generally, as the distance from 0-order diffracted light becomes greater, a Fourier transform component corresponding to more minute structure is provided and therefore, according to the present embodiment, the detection of a more minute defect is possible by oblique incidence. Also, in the present embodiment, the vibratory mirror 33 is not disposed in the light intercepting member 73 and therefore, the reflected light from the semiconductive wafer 1 can be efficiently received and from this point, more minute defects can be detected at a good S/N ratio.

Figure 20:
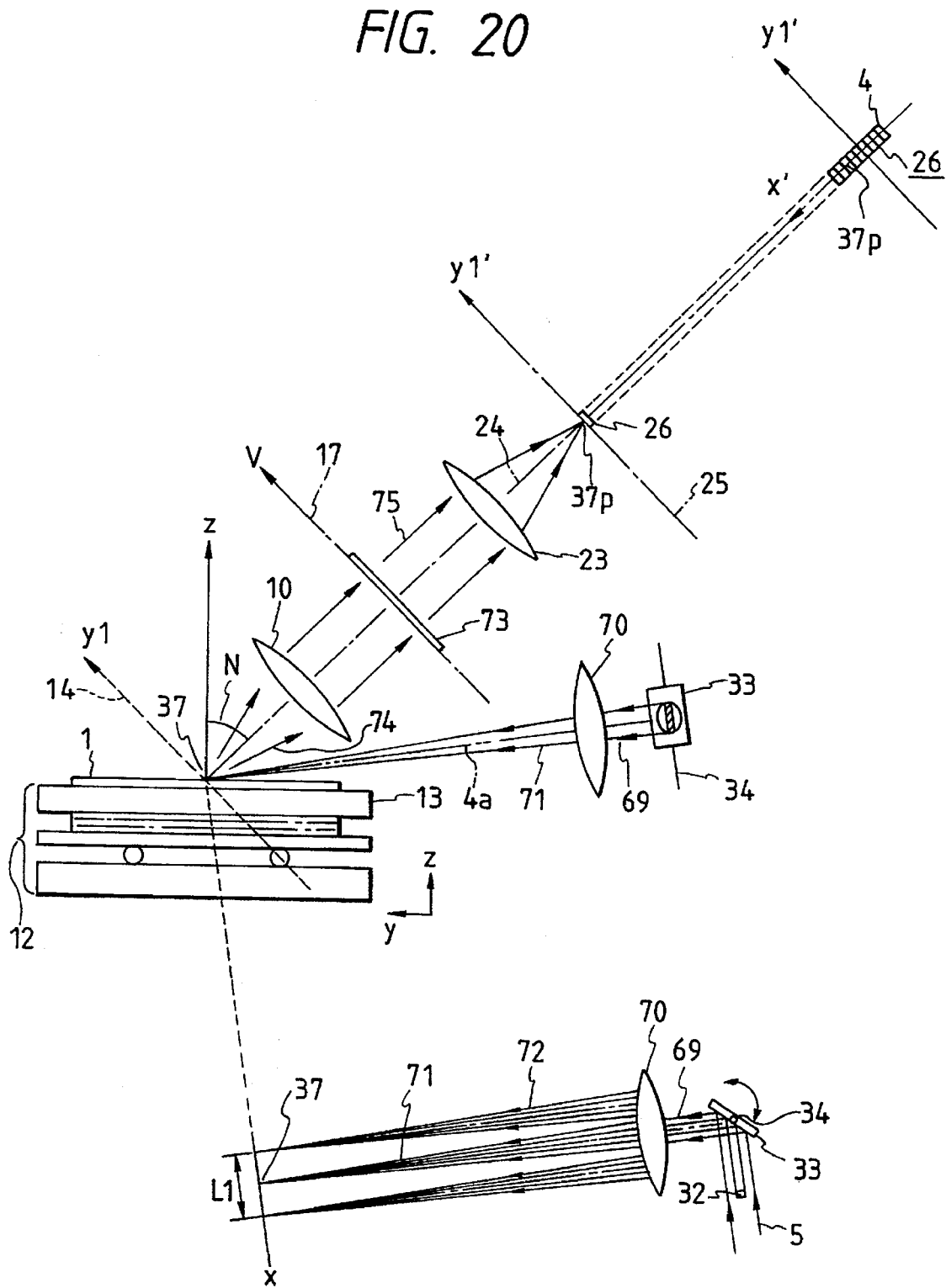
FIG. 20 shows the construction of a fifth embodiment of the present invention.

A fifth embodiment of the present invention will now be described with reference to FIG. 20. This embodiment is one in which the optical axis 24 of the light receiving system in the fourth embodiment of FIG. 17A is inclined toward the optical axis 4a of the illuminating system. In FIG. 20, portions corresponding to those in FIG. 17A are given the same reference numerals and need not be described in detail. That is, FIG. 20 shows the defect inspecting apparatus according to the present embodiment, and the present embodiment is entirely the same as the fourth embodiment of FIG. 17A with the exception that the optical axis 24 of the light receiving system is inclined by an angle N in yz plane with respect to z axis.

In FIG. 20, the optical axis 24 is inclined with respect to the surface of the semiconductive wafer 1 and therefore, the Fourier transform pattern observed in the Fourier transform plane 17 of the Fourier transform lens 10, i.e., UV plane, becomes a pattern farther from 0-order diffracted light than in the fourth embodiment, but a light intercepting member 73 as a space filter may be the same as that in the fourth embodiment. This is because even if the optical axis 24 is inclined in yz plane, equation (1) will be established with respect to the u component of the spatial frequency.

In the present embodiment, the observation area on the Fourier transform plane 17 is farther from 0-order diffracted light than in the fourth embodiment and therefore, the influence of the errorless pattern is further reduced and more minute defects can be detected.

A sixth embodiment of the defect inspecting apparatus according to the present invention will now be described with reference to FIG. 21A, etc. This embodiment is one in which the present invention is applied to an apparatus for detecting any defect present in periodic structure provided with a number of redundant circuit patterns on a semiconductive wafer, and in FIGS. 21A to 21E, members similar to those in the aforedescribed embodiments are given the same reference numerals and need not be described in detail.

FIG. 21A is a front view of the mechanism portion of the defect inspecting apparatus according to the present embodiment, and FIG. 21B is a plan view of the mechanism portion. In FIG. 21A, a monochromatic laser beam from a laser source, not shown, is converted into a substantially parallel beam of light 5 of a diameter G0 by a beam expander, not shown, and this beam of light 5 enters an aperture plate 100. W axis is set so as to pass through the center of the beam of light 5 extending in a direction perpendicular to the plane of the drawing sheet (xz plane) of FIG. 21A (i.e., a direction parallel to y axis). As shown in FIG. 21C, the aperture plate 100 has a light intercepting portion 100a along W axis and a light intercepting portion 100b along an axis AX1. The light intercepting portion 100a is a light intercepting portion of a width G2 crossing the center of the beam of light 5 along W axis. The light intercepting portion 100b is a light intercepting portion of a width G2 crossing the center of the beam of light 5 along the axis AX1 perpendicular to W axis. Accordingly, the beam of light 5 of an outer diameter G0 has its cruciform area of a width G2 along W axis and the axis AX1 intercepted by the aperture plate 100. The width G2 is about 20% of the diameter G0 of the beam of light 5.

In FIG. 21A, the beam of light 5 passed through the aperture plate 100 impinges on a vibratory mirror 101 located near the rearward focal plane (Fourier transform plane) 17 of the Fourier transform lens 10. The vibratory mirror 29 is supported for vibration about a rotational axis perpendicular to xz plane. The beam of light 5 is reflected by the vibratory mirror 101, and is reflected in the direction of a beam of light 30 or a beam of light 31, etc. The beam of light 30, the beam of light 31, etc. are converged on the semiconductive wafer 1 through the Fourier transform lens 10.

That is, the actually effective center of the Fourier transform lens 10 is disposed at a distance one time as great as the focal length of the lens 10 from the surface of the semiconductive wafer 1 (xy plane), and the beam of light 35, the beam of light 36, etc. scanned by the angle of the vibratory mirror 101 are converged on the surface of the semiconductive wafer 1 and form convergence points, respectively. By a variation in the angle of the vibratory mirror 101, a linear illuminated area 37 of a distance L1 along x axis can be continuously scanned at those convergence points. The center of the illuminated area 37 is on the optical axis 24 of the Fourier transform lens 10.

In FIG. 21A, the semiconductive wafer 1 is mounted on the chuck 13 which is a part of the two-dimensional parallel-moving means 12 (see FIG. 1A). The pattern formation surface of the semiconductive wafer 1 is located on the object plane (forward focal plane) 14 of the Fourier transform lens 10, and the converged beams of light 35, 36, etc. illuminate the surface of the semiconductive wafer 1 on which patterns are formed. A beam of light 39 diffracted by the illuminated area of the semiconductive wafer passes through the Fourier transform lens 10 to the Fourier transform plane (rearward focal plane) 17 of the lens 10. The Fourier transform patterns of the circuit patterns on the semiconductive wafer 1 are formed on the Fourier transform plane 17.

The relation between the circuit patterns in the illuminated area of the semiconductive wafer 1 and the created Fourier transform patterns is as previously described. The substance contrastively described in the first embodiment with reference to FIGS. 2A, 3A, etc. also applies to the case of the present embodiment. The optical system equivalent to the optical system of FIG. 21A and corresponding to FIG. 3A is as shown in FIG. 22A.

Figure 22A:
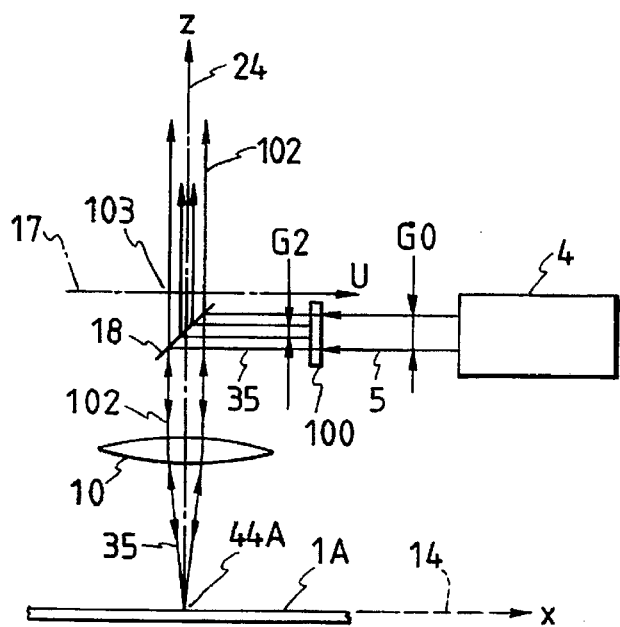
FIG. 22A shows the construction of the essential portions of an optical system equivalent to the optical system in the sixth embodiment.
Figure 22B:
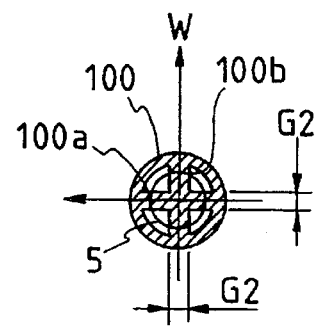
FIG. 22B is a front view of an aperture plate 100.

In FIG. 22A, the parallel beam of light 5 of a circular cross-sectional shape having a diameter G0 emerging from the beam expander 4 is divided into four by the aperture plate 100. The aperture plate 100, as shown in FIG. 22B, has light intercepting portions 100a and 100b crossing the center of the beam of light 5 of a circular cross-section in a cruciform shape. That is, the light intercepting portion 100b is a rectangular light intercepting area of a width G2 around W axis perpendicular to the plane of the drawing sheet of FIG. 22A, and the light intercepting portion 100a is a rectangular light intercepting area of a width G2 around an axis perpendicular to W axis. As shown in FIG. 22B, the beam of light 5 has its cruciform area of a width G2 along W axis and the axis perpendicular to W axis intercepted by the aperture plate 100. The width G2 is about 20% of the diameter G0 of the beam of light 5.

Figure 22C:
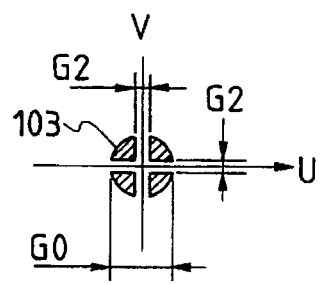
FIG. 22C shows the Fourier transform pattern of the optical system of FIG. 22A to a semiconductive wafer having no pattern thereon.

In FIG. 22A, the beam of light 5 passed through the aperture plate 100 is reflected by the half mirror 18 and travels toward the Fourier transform lens 10. The optical axis 24 of the Fourier transform lens 10 is parallel to z axis perpendicular to the semiconductive wafer 1A. The actually effective center of the Fourier transform lens 10 is located at a distance one time as great as the focal length of the lens 10 from the surface of the semiconductive wafer 1A having no pattern thereon. The beam of light 35 converged by the Fourier transform lens 10 is applied onto the semiconductive wafer 1A having no pattern thereon. The surface of the semiconductive wafer 1A is located in the object plane (forward focal plane) 14 of the lens 10, and the converged beam of light 35 is converged at a point 44A. The converged beam of light 35 is reflected by the semiconductive wafer 1A, and travels back along the same optical path as the optical path until it impinges on the semiconductive wafer 1A, and arrives at the half mirror 18. A beam of light 102 transmitted through the half mirror 18 forms the Fourier transform pattern 103 of the beam of illuminating light itself in the rearward focal plane 17 of the Fourier transform lens 10. This Fourier transform pattern 103, as shown in FIG. 22C, is such that a cruciform area of a width G2 along V axis and U axis passing through the center from a circular pattern of a diameter G0 is a spectrum-free portion.

If the light intercepting member 52 made coincident with the width and direction of the band-like Fourier transform patterns 47A, 48A, 49A and 50A of FIGS. 5A, 5B, 5C and 5D as previously described is disposed in UV plane as shown in FIG. 5E so as to pass only the beam of light from the area 53 in the light intercepting member 52 within the transform area 51, the Fourier transform patterns by the circuit patterns 47, 48, 49 and 50 in the dies on the semiconductive wafer shown in FIGS. 4A, 4B, 4C and 4D will not pass.

Figure 23A:
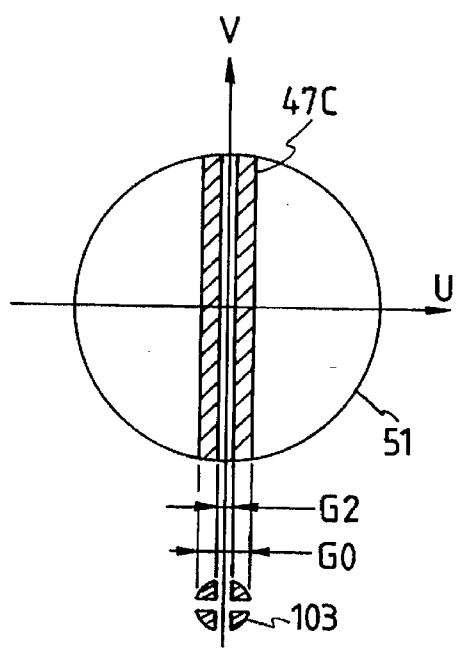
FIG. 23A is a plan view showing a Fourier transform pattern obtained by the linear pattern of FIG. 4A being Fourier-transformed by the optical system in the sixth embodiment of FIGS. 21A to 21E.

On the other hand, when in the optical system of FIG. 22A in the present embodiment, the circuit pattern 47 shown in FIG. 4A is present in the illuminated area 46, a Fourier transform pattern 47C shown in the transform area 51 of FIG. 23A is created on the Fourier transform plane 17. The transform area 51 is a limit area in the spatial frequency area determined by the Fourier transform lens 10. The Fourier transform pattern 47C is a band-like pattern of a width G0 along V axis, but has a spectrum-free portion of a width G2 formed in the central portion thereof. These widths G0 and G2 in U direction are the same as the outer diameter of the Fourier transform pattern 103 of the beam of illuminating light itself and the width of the spectrum-free portion.

Figure 23B:
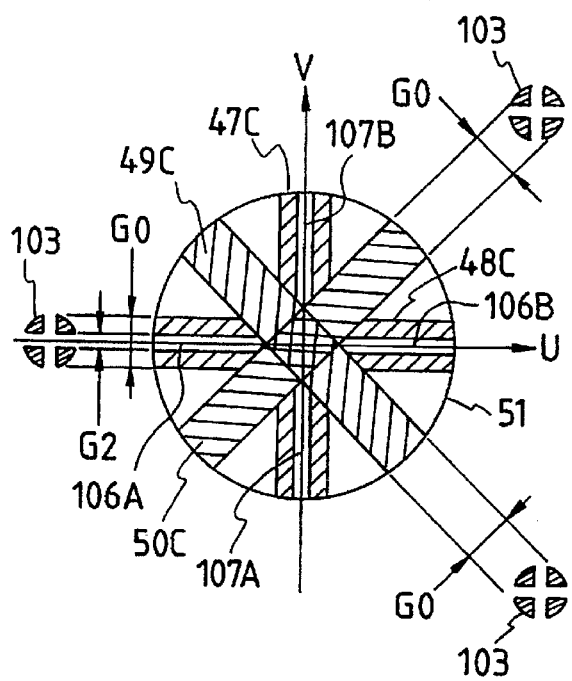
FIG. 23B is a plan view showing a Fourier transform pattern obtained by the mixed pattern of the linear patterns of FIGS. 4A, 4B, 4C and 4D being Fourier-transformed by the optical system in the sixth embodiment of FIGS. 21A to 21E.

Likewise, band-like Fourier transform patterns created when the circuit patterns 48, 49 and 50 of FIGS. 4B, 4C and 4D in respective directions are Fourier-transformed by the optical system of FIG. 22A are the Fourier transform patterns 48C, 49C and 50C, respectively, of FIG. 23B. The widths of these Fourier transform patterns also depend on the Fourier transform pattern 103 of the beam of illuminating light itself. To intercept the Fourier transform patterns created by these circuit patterns, the light intercepting member 52 of FIG. 5E will suffice. However, as shown in FIG. 23B, in the Fourier transform patterns 47C and 48C, the areas of a width G2 on V axis and U axis, respectively, are spectrum-free portions and therefore, even if use is made of a light intercepting member in which as shown in FIG. 23B, rectangular areas 106A and 106B of a width G2 on U axis and rectangular areas 107A and 107B of a width G2 on V axis are eliminated from the light intercepting member 52, Fourier transform patterns obtained by the circuit patterns 47, 48, 49 and 50 of FIGS. 4A, 4B, 4C and 4D being Fourier-transformed by the optical system of FIG. 22A will not pass.

Next, it is to be understood that the two-dimensional periodic patterns 54, 55 and 56 shown in FIGS. 7A, 7B and 7C are present in the illuminated area in the die 2 on the semiconductive wafer which is the object of the inspection by the optical system in the present embodiment of FIG. 22A.

Figure 24A:
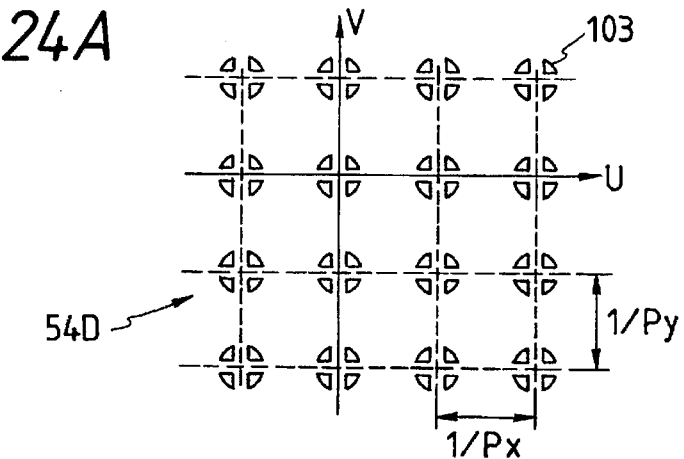
FIGS. 24A, 24B and 24C are plan views showing Fourier transform patterns obtained by the various two-dimensional periodic patterns of FIGS. 7A, 7B and 7C being Fourier-transformed by the defect inspecting apparatus according to the sixth embodiment.
Figure 24B:
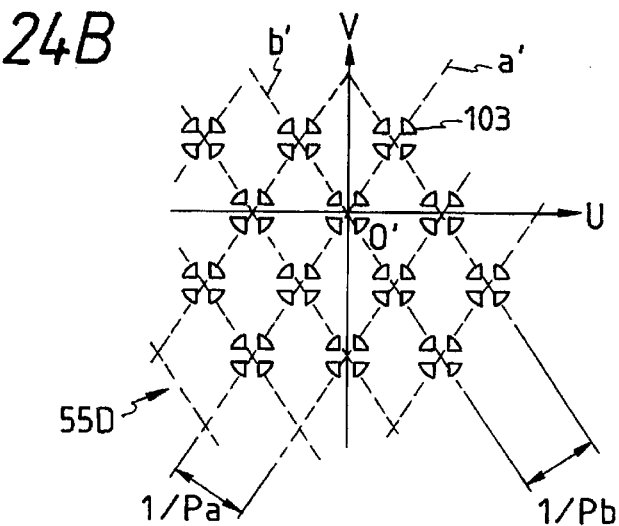
Figure 24C:
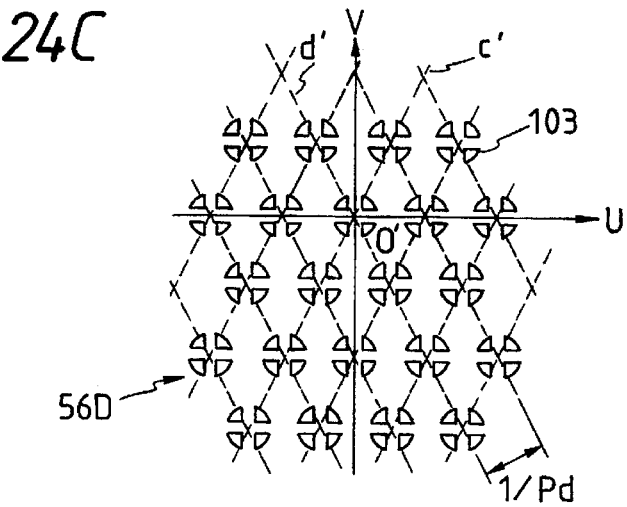

The Fourier transform patterns of the two-dimensional periodic patterns 54, 55 and 56 become the Fourier transform patterns 54D, 55D and 56D, respectively, of FIGS. 24A, 24B and 24C, and in any of these, the Fourier transform pattern (Fourier spectrum) 103 of the beam of illuminating light itself is discretely distributed. That is, the Fourier transform pattern 54D is one in which Fourier transform patterns 103 are arranged at pitches 1/Px and 1/Py along U axis and V axis, respectively, and the Fourier transform pattern 55D is one in which Fourier transform patterns 103 are arranged at pitches 1/Pb and 1/Pa along a' axis orthogonal to a axis and b' axis orthogonal to b axis, respectively. The Fourier transform pattern 56D is one in which Fourier transform patterns 103 are arranged at a pitch 1/Pd along c' axis orthogonal to c axis and d' axis orthogonal to d axis.

Figure 23C:
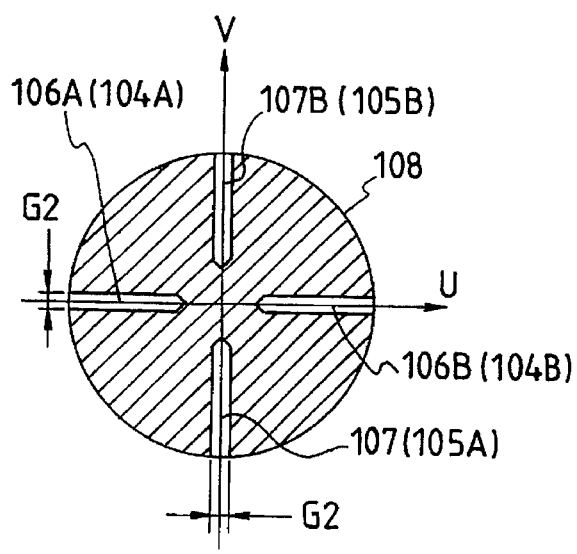
FIG. 23C is a plan view showing a space filter corresponding to the sixth embodiment.

These Fourier transform patterns 54D, 55D and 56D are such that no Fourier transform patterns are present near U axis and near V axis, but exhibit various distributions in the other portions on UV plane. Accordingly, to intercept all of the Fourier transform patterns 54D, 55D and 56D of these two-dimensional periodic patterns as well, use can be made of a light intercepting member 108 as shown in FIG. 23C wherein light can pass through only substantially rectangular areas 106A and 106B of a width G2 along U axis and substantially rectangular areas 107A and 107B of a width G2 along V axis. Those four substantially rectangular areas are portions of the spectrum-free area in which the Fourier transform patterns of circuit patterns having no defect are not present. In the present embodiment, instead of using the light intercepting member 108 itself, as shown in FIG. 21B, reflecting mirrors 104A, 104B, 105A and 105B are obliquely disposed in those areas 106A, 106B, 107A and 107B, respectively.

In the foregoing description, the illuminating light has been described as monochromatic light, but even when the illuminating light is white light or a plurality of chromatic lights or the like, the light intercepting member 108 of FIG. 23C will operate without any problem in principle.

In the present embodiment, as described above, the spatial frequency component of the beam of illuminating light itself and the spatial frequency component of the received beam of light are limited, whereby the spectrum-free area which is not affected by the Fourier transform patterns diffracted by the errorless circuit patterns on the semiconductive wafer is set on the Fourier transform plane 17 of FIG. 21A. This spectrum-free area corresponds to the four areas 106A, 106B, 107A and 107B on the light intercepting member 108 of FIG. 23C.

In FIG. 21B, of the Fourier transform patterns formed on the UV coordinates on the Fourier transform plane (rearward focal plane) 17 of the Fourier transform lens 10, a beam of light passing through areas corresponding to the areas 107A and 107B of FIG. 23C is bent by 90° with respect to z axis by the reflecting mirrors 105A and 105B, respectively, and is reflected in the direction of U axis. The reflected beam of light 109, i.e., a first defect carrying beam of light, enters a reverse Fourier transform lens 23B having U axis as its optical axis.

The reverse Fourier transform lens 23B reversely Fourier-transforms the light patterns reflected by the reflecting mirrors 105A and 105B, of the light from the illuminated die on the semiconductive wafer 1. The reverse Fourier transform lens 23B is disposed at a distance one time as great as the focal length of the lens 23B from V axis on the rearward focal plane 17 of the Fourier transform lens 10. Also, the light receiving surface of a one-dimensional photodetector array 26B is disposed about an optical axis 110B on the image plane 25B which is the rearward focal plane of the reverse Fourier transform lens 23B, and the coordinates axes on the light receiving surface of the photodetector array 26B which are conjugate with x axis and y axis on the semiconductive wafer 1 are defined as $x_2$ axis and $Y_2$ axis, respectively. The image pickup elements 41B of the photodetector array 26B, as shown in FIG. 21E, are aligned within the range of a length LB on $x_2$ axis conjugate with x axis of the Fourier transform patterns formed on the Fourier transform plane 17, a beam of light passing through areas corresponding to the areas 106A and 106B of FIG. 23C is bent by 90° with respect to z axis by the reflecting mirrors 104A and 104B, as shown in FIG. 21B, and is reflected in the direction of V axis. The reflected beam of light 111, i.e., a second defect carrying beam of light, enters a reverse Fourier transform lens 23A having V axis as its optical axis 110A.

The reverse Fourier transform lens 23A reversely Fourier-transforms the light patterns of the light from the illuminated die on the semiconductive wafer 1 which have been reflected by the reflecting mirrors 104A and 104B. The reverse Fourier transform lens 23A is disposed at a distance one time as great as the focal length of the lens 23A from U axis on the rearward focal plane 17 of the Fourier transform lens 10. Also, the light receiving surface of a one-dimensional photodetector array 26A is disposed about an optical axis 110A on the image plane 25A which is the rearward focal plane of the reverse Fourier transform lens 23A, and the coordinates axes on the light receiving surface of the photodetector array 26A which are conjugate with x axis and y axis on the semiconductive wafer 1 are defined as $x_1$ axis and $y_1$ axis, respectively. The image pickup elements 41A of the photodetector array 26A, as shown in FIG. 21D, are aligned within the range of a length LA on $x_1$ axis conjugate with x axis. In the present embodiment, design is made such that the images 37A and 37B of the same magnification of the defects in the linear illuminated area 37 on the semiconductive wafer 1 of FIG. 21A are formed on the image planes 25A and 25B, respectively.

When the spot diameters on the image planes 25A and 25B relative to the spot diameter $d_1$ at the convergence points of the beams of light 35, 36, etc. applied onto the semiconductive wafer 1 are $d_{21}$ and $d_{22}$, respectively, the one-dimensional photodetector array 26A has a plurality of image pickup elements 41A of substantially the same size as the spot diameter $d_{21}$ and aligned in $x_1$ direction. The number of these image pickup elements 41A is a number great enough to cover the area of a length LA on the image plane 25A corresponding to the illuminated area 37 of a length L1 on the semiconductive wafer 1.

Likewise, the one-dimensional photodetector array 26B also has a plurality of image pickup elements 41B of substantially the same size as the spot diameter $d_{22}$ and aligned in $x_2$ direction. The number of these image pickup elements 41B is a number great enough to cover the area of a length LB on the image plane 25B corresponding to the illuminated area 37 of a length LB on the semiconductive wafer 1. Also, in the present embodiment, design is made such that the image pickup elements of the photodetector arrays 26A and 26B correspond at one to one another and the corresponding image pickup elements pick up the image of the same object point.

[Description of the Signal Processing Systems]

A first signal processing system in the present embodiment will now be described. In the present embodiment, the number of the one-dimensional photodetector arrays is two and therefore, two image pickup signals of a defect are obtained. So, description will hereinafter be made of a method of obtaining the result of defect inspection from these two defect image pickup signals.

Figure 25A:
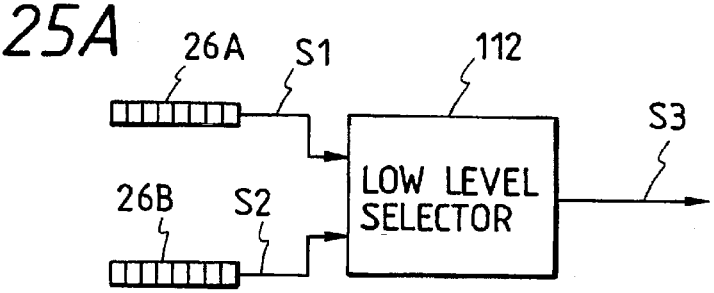
FIG. 25A is a block diagram of a first signal processing system.

FIG. 25A shows a first example of the construction of the signal processing system. In FIG. 25A, an image pickup signal S1 outputted from the photodetector array 26A and an image pickup signal 26B outputted from the photodetector array 26B are supplied to a low level selector 112, which compares the two image pickup signals S1 and S2 with each other for each image pickup element (pixel), selects smaller one of the two signals and outputs it as an image pickup signal S3. This image pickup signal S3 corresponds to the defect image.

Figure 25B:
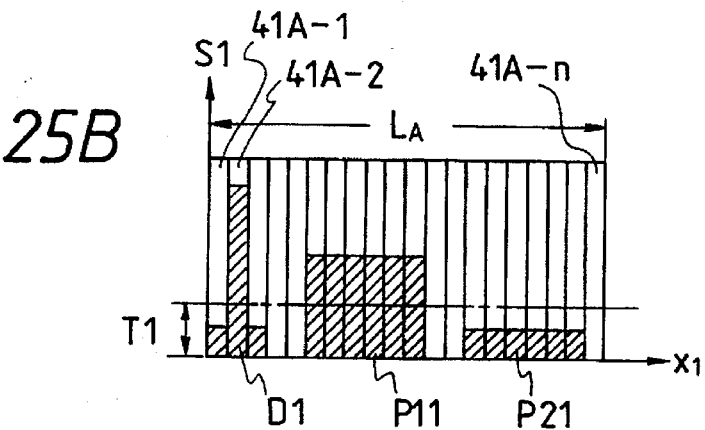
FIGS. 25B, 25C and 25D are waveform graphs showing image pickup signals in FIG. 25A.
Figure 25C:
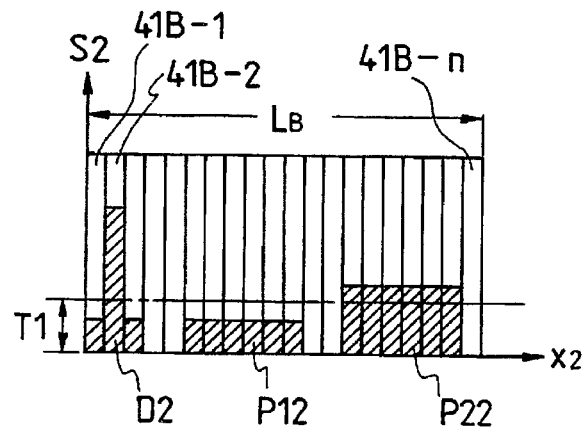

An example of those image pickup signals S1 and S2 each is shown in FIGS. 25B and 25C. In FIG. 25B, the axis of abscissa represents $x_1$ axis within the range of a width LA, and the axis of ordinate represents the image pickup signals of image pickup elements (pixels) 41A-1, 41A-2, ..., 41A-n. Likewise, in FIG. 25C, the axis of abscissa represents $x_2$ axis within the range of a width LB, and the axis of ordinate represents the image pickup signals of image pickup elements (pixels) 41B-1, 41B-2, ..., 41B-n. The signals S1 and S2 show signals obtained by the illuminated area 37 on the semiconductive wafer being scanned once by the vibratory mirror 101 with the aid of the illuminating light in FIG. 21A. Also, D1 and D2 designate the images of defects, and P11, P21 and P12, P22 denote the images of circuit patterns which could not be removed by filtering in the Fourier plane. In FIGS. 25B and 25C, a threshold value T1 is one set to eliminate electrical noise and residual noise from the circuit, and the image pickup signals S1 and S2 exceeding the threshold value T1 are regarded as being effective.

In FIG. 25B, the portions which exceed the threshold value level T1 are the image D1 of a defect and the image P11 of a circuit pattern, and in FIG. 25C, the portions which exceed the threshold value level T1 are the image D2 of a defect and the image P22 of a circuit pattern. In FIGS. 25A and 25B, the image pickup elements 41A-1 to 41A-n on $x_1$ axis and the image pickup elements 41B-1 to 41B-n on $x_2$ axis correspond to the same position on the semiconductive wafer 1. Thus, the image D1 of the defect of the image pickup element 41A-2 on $x_1$ axis and the image D2 of the defect of the image pickup element 41B-2 on $x_2$ axis coincide with each other on the semiconductive wafer 1, and are the signals from the same defect. Likewise, the images P11 and P12 of the circuit pattern are the images of the same circuit pattern, and the images P21 and P22 of the circuit pattern are the images of the same circuit pattern.

Generally, the Fourier transform pattern of a defect is distributed over the whole of the Fourier transform plane and therefore, substantially equal images are obtained in the one-dimensional photodetector arrays 26A and 26B. In contrast, the Fourier transform pattern of a circuit pattern exhibits a one-sided distribution on the Fourier transform plane. Therefore, when images corresponding to the reverse Fourier transformation of Fourier spectra remarkably different on locations like this are received, the image on the photodetector array 26A and the image on the photodetector array 26B may somewhat differ in intensity even though they are the images of the same circuit pattern. That is, the optimum direction of the spectrum-free area on the space filter may somewhat vary depending on the circuit pattern. For example, the images P11 and P12 of the circuit pattern are the images of the same circuit pattern, but differ in intensity, and this also holds true of the images P21 and P22 of another circuit pattern.

Figure 25D:
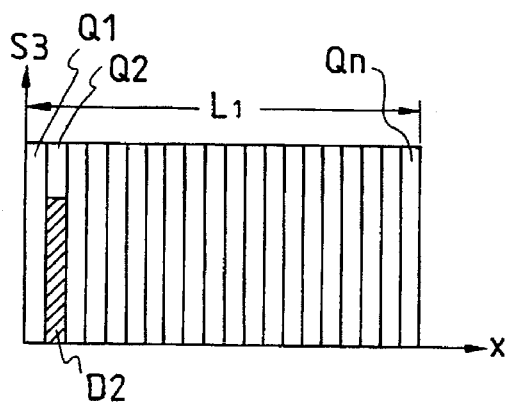

The first signal processing system is designed with attention paid to this point. The low level selector 112 of FIG. 25A compares the signal levels of the two image pickup signals S1 and S2 for each image pickup element corresponding to the same object point, and outputs lower one of the signal levels. However, it effects a calculation only about the signal of the image pickup element which has exceeded the threshold value T1 and as a result, there is obtained the image pickup threshold value S3 of FIG. 25D. The signal intensity of the image pickup element when it does not exceed the threshold value T1 is regarded as 0. Thus, only when both of the two image pickup signals corresponding to the same object point exceed the threshold value, any other signal level than 0 is outputted. This is equivalent to a method of judging the presence or absence of a defect by the logical product of signals binarized at the threshold value T1, and judging the intensity of the defect by the smaller signal intensity.

Figure 26A:
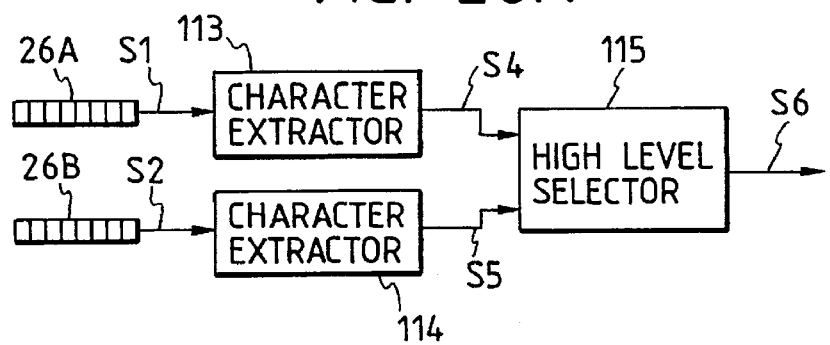
FIG. 26A is a block diagram of a second signal processing system.

FIG. 26A shows a second signal processing system. In FIG. 26A, the image pickup signal S1 of the photodetector array 26A and the image pickup signal S2 of the photodetector array 26B are supplied to character extractors 113 and 114, respectively, and an image pickup signal S4 outputted from the character extractor 113 and an image pickup signal S5 outputted from the character extractor 114 are supplied to a high level selector 115. An image pickup signal S6 corresponding to the image of a defect is outputted from the high level selector 115.

Figure 26B:
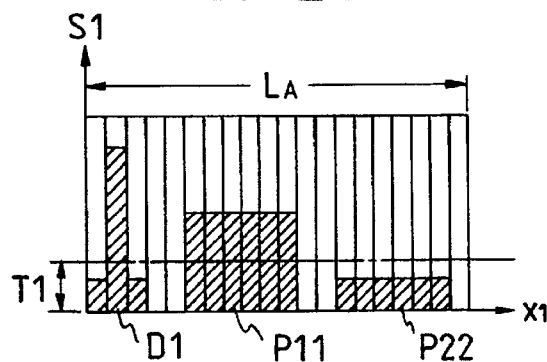
FIGS. 26B, 26C, 26D, 26E and 26F are waveform graphs showing image pickup signals in FIG. 26A.
Figure 26C:
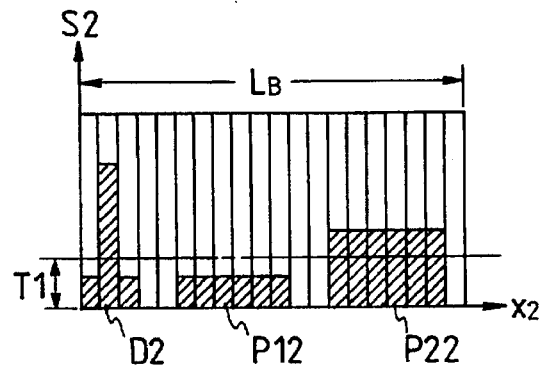
Figure 27A:
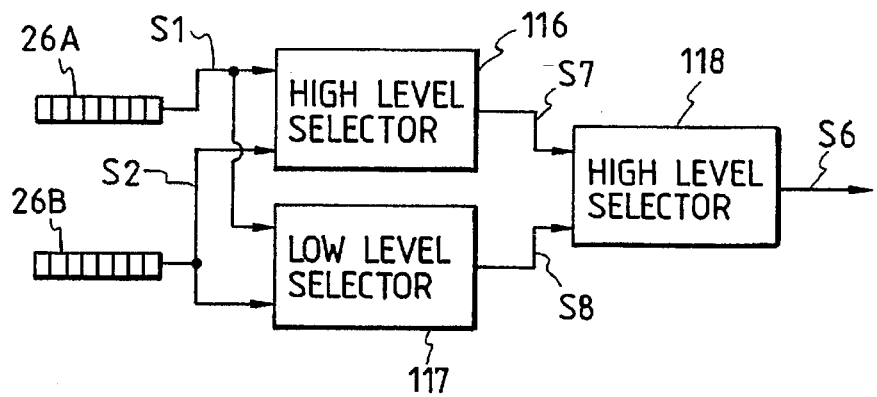
FIG. 27A is a block diagram of a third signal processing system.
Figure 27B:
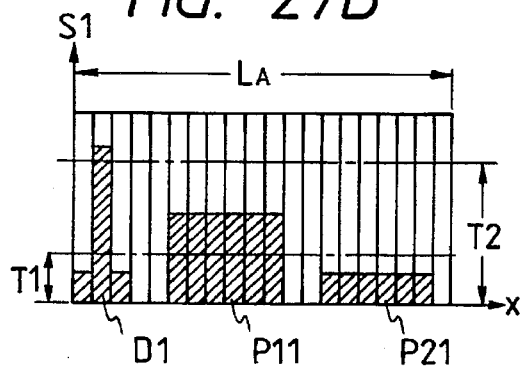
FIGS. 27B, 27C, 27D, 27E and 27F are waveform graphs showing image pickup signals in FIG. 27A.
Figure 27C:
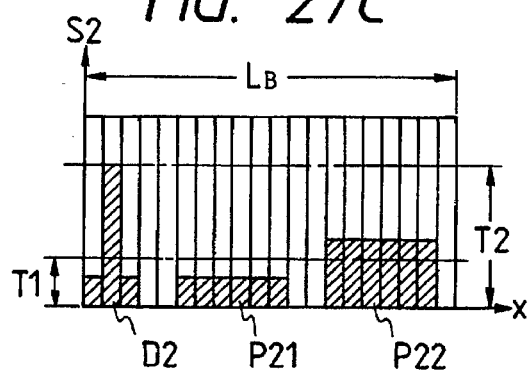

FIGS. 26B and 26C show the image pickup signals S1 and S2, respectively, and FIGS. 26B and 27C are the same as FIGS. 25B and 25C, respectively.

In this signal processing system, the images of excess circuit patterns are eliminated from the images on the two one-dimensional photodetector arrays 26A and 26B by ordinary image processing, and only the image of a defect is extracted. As the character extractors 113 and 114 shown in FIG. 26A, use is made of processing systems capable of extracting the characters of anticipated defect signals. The detected defect is generally very small, and is smaller than the diameter of the beam spot formed on the semiconductive wafer 1 by the beam of illuminating light. Accordingly, the image of the detected defect only has a size corresponding to one to several image pickup elements on the one-dimensional photodetector arrays 26A and 26B. This is because in the present embodiment, the spot on the image plane corresponding to the spot diameter is made substantially coincident with each image pickup element.

Figure 26D:
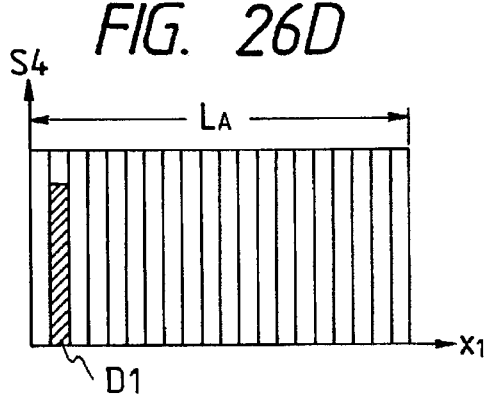
Figure 26E:
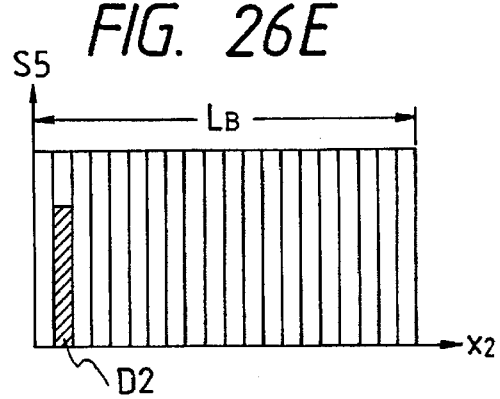
Figure 26F:
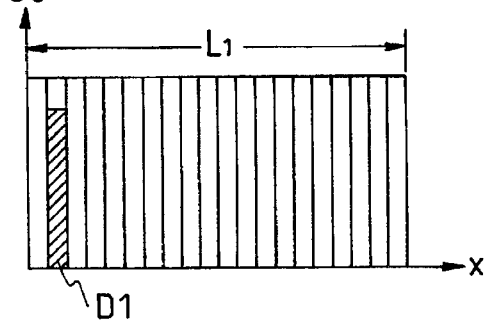

So, in this signal processing system, the character extractors 113 and 114 count how many image pickup elements the size of the image corresponding to the image pickup signal exceeding the threshold value T1 corresponds to, whereby they extract the images D1 and D2 of defects. Thus, the image pickup signal S4 of FIG. 26D and the image pickup signal S5 of FIG. 26E are obtained. These image pickup signals S4 and S5 are inputted to the high level selector 115, and are compared with each other for each corresponding image pickup element, and always the greater signal value is outputted. As a result, an image pickup signal S6 shown in FIG. 26F is obtained.

FIG. 27A shows a third signal processing system. In FIG. 27A, the image pickup signal S1 of the photodetector array 26A is supplied in common to a high level selector 116 and a low level selector 117, and the image pickup signal S2 of the photodetector array 26B is supplied in common to the high level selector 116 and the low level selector 117. An image pickup signal S7 outputted from the high level selector 116 and an image pickup signal S8 outputted from the low level selector 117 are supplied to a high level selector 118, from which is outputted an image pickup signal S6 corresponding to the image of a defect.

FIGS. 27B and 27C show the image pickup signals S1 and S2, respectively, and FIGS. 27B and 27C are the same as FIGS. 25B and 25C, respectively. However, in this signal processing system, a threshold value T1 equal to that in the first signal processing system and a higher threshold value T are set.

Figure 27D:
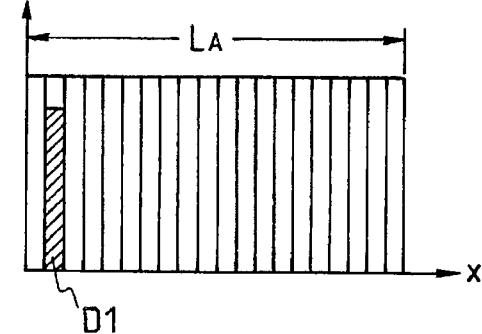
Figure 27E:
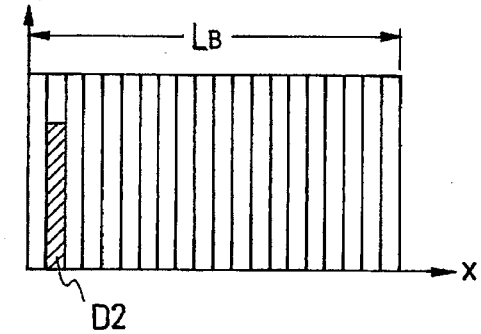

In this case, the operation of the low level selector 117 is the same as the operation of the low level selector 112 of FIG. 25A, and the image pickup signal S8 of FIG. 27E which is the result of the calculation by the low level selector 117 using the threshold value T1 is the same as the image pickup signal S3 in the first signal processing system of FIG. 25A.

In this signal processing system, another process is further carried out in parallel by the use of a threshold value T2. This is effected by the high level selector 116. The high level selector 116, in FIGS. 27B and 27C, selects an image pickup element exceeding the threshold value T2 and outputs higher one of the corresponding image pickup signals of the two photodetector arrays 26A and 26B always corresponding to the same object point. Accordingly, the signal intensity of the image pickup signal which does not exceed the threshold value T2 is regarded as 0, and if there is even one of the signals of two image pickup elements corresponding to the same object point which exceeds the threshold value T2, the greater signal is outputted as the image pickup signal S7. Thus, the image pickup signal S7 of FIG. 27D is obtained. This is equivalent to a method of judging the presence or absence of a defect by the logical sum of signals binarized at the threshold value T2, and judging the intensity of the defect by the greater signal intensity.

Figure 27F:
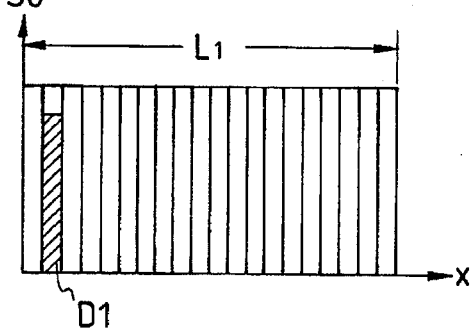

Further, in this signal processing system, the image pickup signals S7 and S8 are compared with each other for each image pickup element by the high level selector 118, and one of the two image pickup signals corresponding to the same object point which is always greater is outputted as the image pickup signal S6. Thus, the image pickup signal S6 of FIG. 27F is obtained. Thereby, only the image pickup signal corresponding to the image of the defect can be reliably detected and also, the SN ratio of that image pickup signal can be further enhanced.

The relative scanning of the illuminated area (inspected area) in each die on the semiconductive wafer 1 of FIG. 21A is similar to the relative scanning described with reference to FIG. 1F and therefore need not be described in detail. The relative scanning as shown in FIG. 1F is repeated to relatively scan the whole of the interior of the die 2 by converged light, and the images of defects created during this scanning are received by the image pickup elements of the photodetector arrays 26A and 26B. The image of the defect introduced by each image pickup element is converted into an image pickup signal corresponding to the defect.

As described above, according to the present embodiment, the angles of incidence of the beams of light 35, 36, etc. as the illuminating light onto the semiconductive wafer 1 are limited by the aperture plate 100 between the beam expander and the semiconductive wafer 1, whereby in the Fourier transform plane 17 of the Fourier transform lens 10, there is set a spectrum-free area in which no light component appears when there is no defect in the circuit patterns on the semiconductive wafer 1. The reflecting mirrors 104A, 105A, etc. extract the light component of the spectrum-free area and therefore, only the light from a defective pattern on the semiconductive wafer 1 is supplied to the photodetector arrays 26A and 26B. Accordingly, the photodetector arrays 26A and 26B can receive only the image of the defect.

In FIG. 21A, it is not always necessary to provide the aperture plate 100 in the optical path of the beam of light 5. Instead, by adjusting the angle of incidence of the principal ray of the illuminating light onto the semiconductive wafer 1, a spectrum-free area may be set on the Fourier transform plane 17, and the reflecting mirrors 104A, 105A, etc. may be disposed in this spectrum-free area.

A seventh embodiment of the present invention will now be described with reference to FIGS. 28A to 29E. This seventh embodiment is an improvement over the sixth embodiment of FIGS. 21A to 21E, and in FIGS. 28A to 29E, portions corresponding to those in FIGS. 21A to 21E are given the same reference characters and need not be described in detail.

Figure 28B:
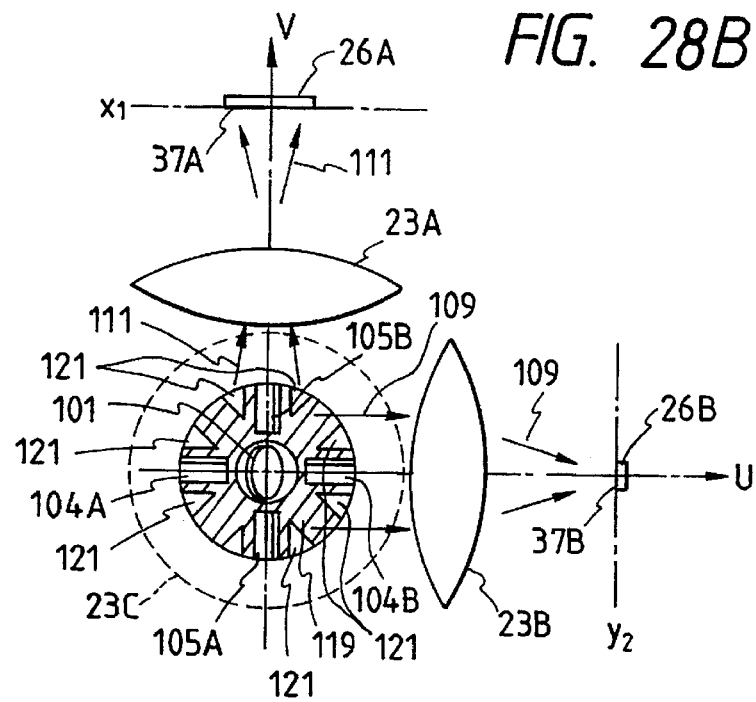
FIG. 28B is a plan view of the apparatus of FIG. 28A to a Fourier transform plane 17.
Figure 28A:
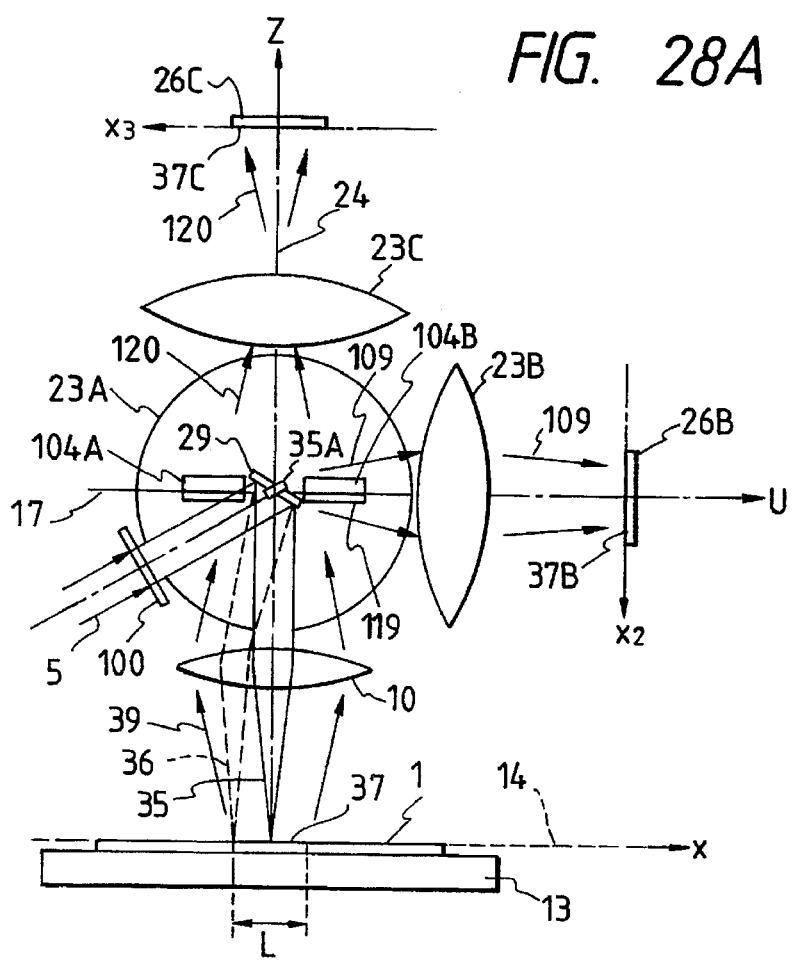
FIG. 28A is a front view showing a defect inspecting apparatus according to a seventh embodiment of the present invention.

FIG. 28A is a front view of the mechanism portion of the defect inspecting apparatus according to the present embodiment, and FIG. 28B is a plan view of the mechanism portion as it is seen from above the Fourier transform plane 17. In FIGS. 28A and 28B, a space filter 119 is disposed so as to cover the vicinity of the intermediate portions of the reflecting mirrors 104A, 104B and reflecting mirrors 105A, 105B on the Fourier transform plane 17. Further, a reverse Fourier transform lens 23C is disposed along the optical axis 24 and above the Fourier transform plane 17. The reverse Fourier transform lens 23C is located at a distance one time as great as the focal length of the lens 23C from the Fourier transform plane 17, and the light receiving surface of a one-dimensional photodetector array 26C is disposed on the image plane (rearward focal plane) of the reverse Fourier transform lens 23C. The light receiving surface of the photodetector array 26C is disposed about the optical axis 24 in the image plane, and the image pickup elements of the photodetector array 26C are aligned on $x_3$ axis conjugate with x axis, and the space filter 119 on the Fourier transform plane 17 has a light transmitting portion 121 as indicated by hatching in FIG. 28B. The space filter 119 corresponds to the light intercepting member 52 of FIG. 5E, and the light transmitting portion 121 corresponds to the light transmitting portion 53 of FIG. 5E. Thus, according to the space filter 119, the Fourier transform patterns of the simple circuit patterns 47, 48, 49 and 50 shown in FIGS. 4A, 4B, 4C and 4D or the rough circuit patterns of a size substantially equal to the size of the beam spot on the semiconductive wafer 1 by the beam of illuminating light are eliminated most efficiently. In the other points, the construction of the present embodiment is similar to that of the embodiment of FIG. 21A and need not be described any further.

The operation of the present embodiment will now be described. In FIG. 28A, a beam of defect carrying light 120 transmitted through the space filter 119 enters the reverse Fourier transform lens 23C. The lens 23C reversely Fourier-transforms the filtered light pattern, and forms the image 32C of a defect on the semiconductive wafer 1 on the light receiving surface of the photodetector array 26C on the image plane. In the present embodiment, design is made such that the images of defects of the same magnification are obtained on the light receiving surfaces of three photodetector arrays 26A, 26B and 26C. Accordingly, in the present embodiment, there are obtained the three images of the defects corresponding to the reverse Fourier transformation of the filtered light pattern.

Figure 29A:
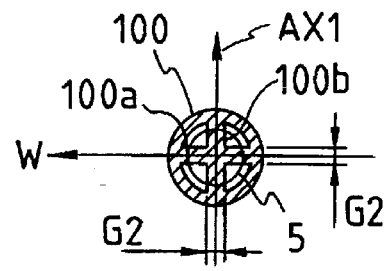
FIG. 29A shows an aperture plate 100 in FIG. 28A as it is seen in the direction of travel of the beam of light 5.
Figure 29B:
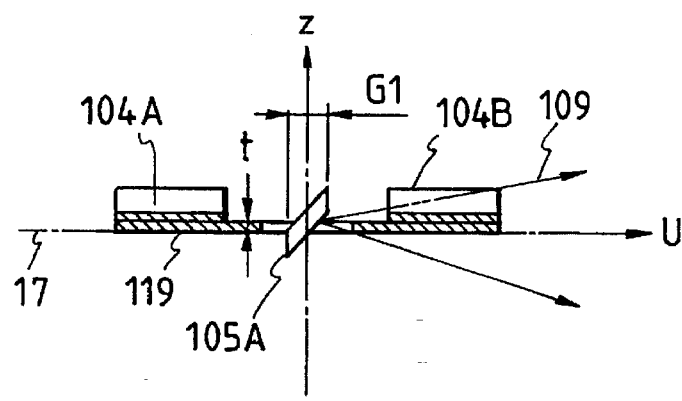
FIG. 29B is an enlarged view of the vicinity of the Fourier transform plane in FIG. 28A.

Also, FIG. 29B is a cross-sectional view of the space filter 119 on the Fourier transform plane 17 in Uz plane and the reflecting mirrors 104A, 104B. The reflecting mirror 105A turns back a beam of light of a width G1 by 90° in U direction and transmits it in the direction of U axis, and the reflecting mirrors 104A and 104B turn back a beam of light of a width G1 by 90° in V direction and transmit it in the direction of V axis. The beam of light 109 reversely Fourier-transformed by the reverse Fourier transform lens 23B of FIG. 28A is one reflected by the reflecting mirrors 105A and 105B, and thereafter, there is created more or less eclipse in it by the space filter 119. In order to minimize this eclipse, it is desirable that the thickness t of the space filter 119 in z direction be made as small as possible. Also, to render the eclipse zero, instead of installing the space filter 119 on the Fourier transform plane 17, a plane conjugate with the Fourier transform plane 17 may be made once again on the optical axis 24 by a relay optical system, and the space filter 119, the reverse Fourier transform lens 23C and the one-dimensional photodetector array 26C may be installed on that conjugate plane.

Figures 29C, 29D, 29E:
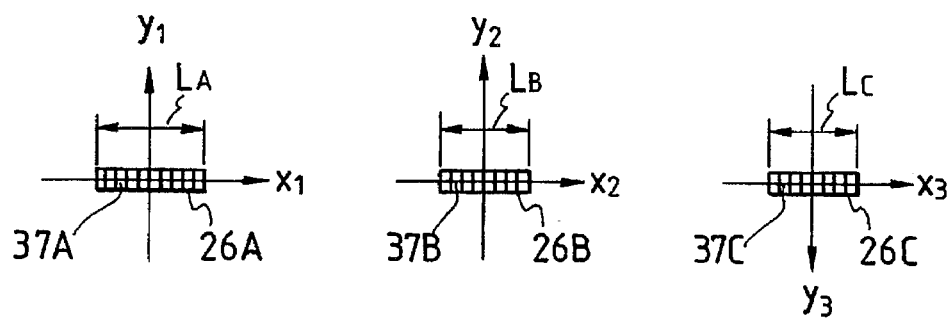
FIGS. 29C, 29D and 29E show photodetector arrays 26A, 26B and 26C, respectively, in FIGS. 28A and 28B.

FIGS. 29C, 29D and 29E show the one-dimensional photodetector arrays 26A, 26B and 26C, respectively, and the image pickup elements on the photodetector arrays 26A, 26B and 26C are designed so as to correspond to the same object point in one-to-one relationship with one another. Further, when the spot diameter on the image plane of the lens 23C relative to the spot diameter on the semiconductive wafer 1 at the convergence points of the beams of illuminating light 35, 36, etc. on the semiconductive wafer 1 is contrasted with each image pickup element of the photodetector array 26C, the photodetector array 26C has a plurality of image pickup elements of substantially the same size as the spot diameter on the image plane and aligned in the direction of one-dimensional $x_3$ axis, the number of the image pickup elements is a number great enough to cover an area of a length LC on the image plane corresponding to the illuminated area 37 of a length L1 on the semiconductive wafer 1.

Since in the present embodiment, there are three one-dimensional photodetector arrays 26A, 26B and 26C, there are obtained three image pickup signals corresponding to the image of a defect. A signal processing system for finding the result of defect inspection from these three image pickup signals may basically be the signal processing system shown in the sixth embodiment. That is, in the present embodiment, the objects of processing by the signal processing system shown in FIGS. 25A and 26A or FIG. 27A can be increased from two to three. Also, the method of relatively moving the illuminated area 37 (inspected area) on the semiconductive wafer 1 may be just the same as the method in the sixth embodiment.

An eighth embodiment of the present invention will now be described with reference to FIGS. 30A to 31B. This embodiment, like the sixth embodiment, is one in which the present invention is applied to a defect inspecting apparatus for detecting any defect on a semiconductive wafer, and in FIGS. 30A, 30B, 31A and 31B, portions corresponding to those in FIGS. 21A to 21E and FIGS. 23A to 23C are given the same reference characters and need not be described in detail.

Figures 30A, 30B:
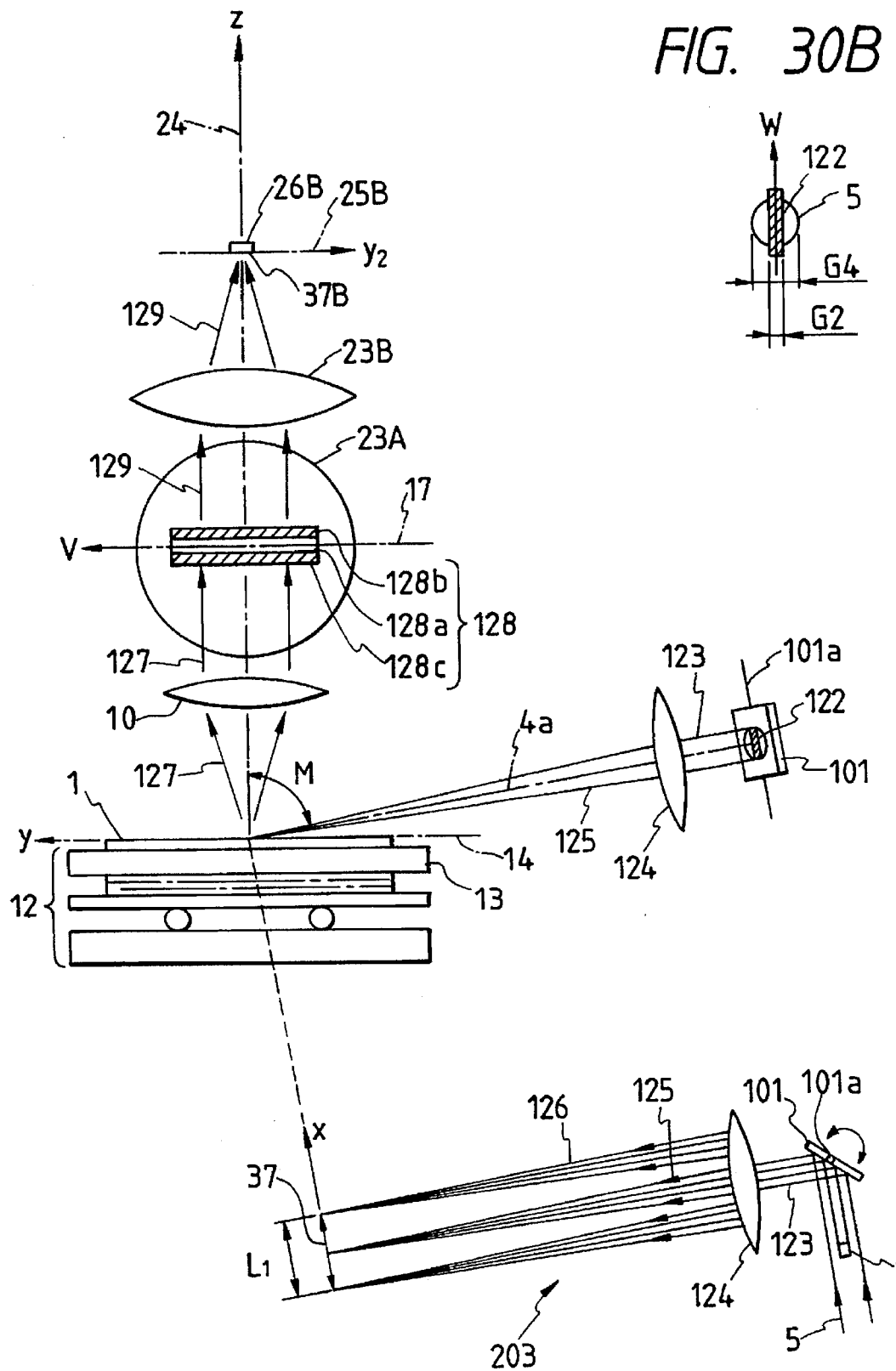
FIG. 30A is a front view showing an eighth embodiment of the present invention.
FIG. 30B shows a light intercepting member 122 in the eighth embodiment as it is seen in the direction of travel of the beam of light 5.

FIG. 30A schematically shows the construction of the defect inspecting apparatus according to the present embodiment, and a portion 203 in FIG. 30A shows the construction of an illuminating system in a plane containing the optical axis of the illuminating system and x axis. In the portion 203 of FIG. 30A, a substantially parallel beam of light 5 of a diameter G4 comprising monochromatic light emerging from a beam expander, not shown, enters a rectangular light intercepting member 122 of a width G2 about W axis passing through the center of the beam of light 5 and perpendicular to X direction. FIG. 30B shows the shape of the light intercepting member 122, and the beam of light 5 has its area of a width G2 about W axis intercepted by the light intercepting member 122.

In FIG. 30A, the beam of light 5 passed through the light intercepting member 122 is reflected by a vibratory mirror 101 located near the entrance pupil of a scanning lens 73, and a beam of light 123 reflected by the vibratory mirror 101 rotated about an axis 101a is made into a converged beam of light 125 by a scanning lens 124. The converged beam of light 125 forms a beam spot on the point of intersection between the surface of the semiconductive wafer 1 and the optical axis 4a of the illuminating system. As shown in the portion 203 of FIG. 30A (corresponding to the portion 202 of FIG. 17A), the converged beam of light 125 is made, for example, into a converged beam of light 126 by the cooperative operation of the vibratory mirror 101 and scanning lens 124, and the beam spot can move on the linear illuminated area 37 of a length L1 on the surface of the semiconductive wafer 1. The lengthwise direction of this illuminated area 37 is coincident with x direction. Also, the scanning lens 124 is a telecentric scan lens, and as long as the beam spot moves from one end point to the other end point on the illuminated area 37, the optical axis of the converged beam of light always enters perpendicularly to x axis.

Further, the direction of the light intercepting member 122 is determined so that for example, in the cross-section of the converged beam of light 125, the lengthwise direction of the area intercepted by the light intercepting member 122 may always be perpendicular to x axis. Therefore, in the present embodiment, W axis which is the lengthwise direction of the light intercepting member 122 is perpendicular to a plane containing x axis and the optical axis 4a. Also, x axis is parallel to one of the axes of the reference orthogonal coordinates during the depiction of circuit patterns formed on the semiconductive wafer 1.

In FIG. 30A, the optical axis 4a of the illuminating system obliquely enters the surface of the semiconductive wafer 1. Also, the center of the illuminated area 37 on the semiconductive wafer 1 is located on the optical axis 24 of the Fourier transform lens 10, and the optical axis 24 coincides with z axis. The object plane (forward focal plane) 14 of the Fourier transform lens 10 is xy plane on which the linear illuminated area 37 is located. A beam of light 127 diffracted by the circuit pattern included in the illuminated area 37 of the semiconductive wafer 1 passes through the Fourier transform lens 10 to the Fourier transform plane (rearward focal plane) 17, and a Fourier transform pattern is formed in the Fourier transform plane 17.

In the present embodiment, the optical axis 4a of the illuminating optical system intersects z axis at an angle M. Therefore, the area of the Fourier transform pattern observed in the Fourier transform plane 17 of the Fourier transform lens 10 deviates by $V_0$ (=$fm_0$=$fin^M$) (see equation (6)) along V axis, relative to the area of the Fourier transform pattern observed in the Fourier transform plane 17 in the sixth embodiment of FIGS. 21A to 21E. So, in the present embodiment, a space filter simpler than in the sixth embodiment is used as the space filter on the Fourier transform plane 17.

Describing this in detail, the Fourier transform pattern observed in the Fourier transform plane 17 when the circuit pattern 47 shown in FIG. 4A is present in the illuminating area 37 of the illuminating system in the present embodiment becomes similar to the Fourier transform pattern 47B of FIG. 18A. In the sixth embodiment, the interior of the transform area 51 around the point of intersection between V axis and U' axis in FIG. 18A has been observable, while in the present embodiment, the optical axis 4a of the illuminating system obliquely enters the semiconductive wafer 1 and thus, in FIG. 18A, the interior of the transform area 52A around the point of intersection between U axis shifted by $V_0$ along V axis and V axis is observed. The point of intersection between V axis and U' axis indicates the direction of 0-order diffracted light or regularly reflected light.

Where the circuit patterns 48, 49 and 50 of FIGS. 4B, 4C and 4D in various directions are formed on the semiconductive wafer 1 in the present embodiment of FIG. 30A, the Fourier transform pattern created on the Fourier transform plane 17 becomes the Fourier transform pattern 52 of FIG. 18B. In the sixth embodiment, the interior of the transform area 51 has been observed, while in the present embodiment, the interior of the transform area 51A shifted by $V_0$ by oblique incidence is observed and therefore, only two band-like patterns spaced apart from each other by an area 73a of a width G2 near V axis are observed. The Fourier transform pattern in this transform area 51A is the same as the Fourier transform pattern 47B of FIG. 18A.

Likewise, patterns created on the Fourier transform plane 17 when the two-dimensional periodic patterns 54, 55 and 56 shown in FIGS. 7A, 7B and 7C are formed on the semiconductive wafer 1 of FIG. 30A are the Fourier transform patterns 54C, 55C and 56C shown in FIGS. 19A, 19B and 19C, respectively. These Fourier transform patterns 54C, 55C and 56C are also observed in the area shifted by $V_0$ with respect to V axis. Also, the points of intersection between V axis and U axis shown in FIGS. 19A, 19B and 19C indicate the direction of 0-order diffracted light.

Figure 18C:
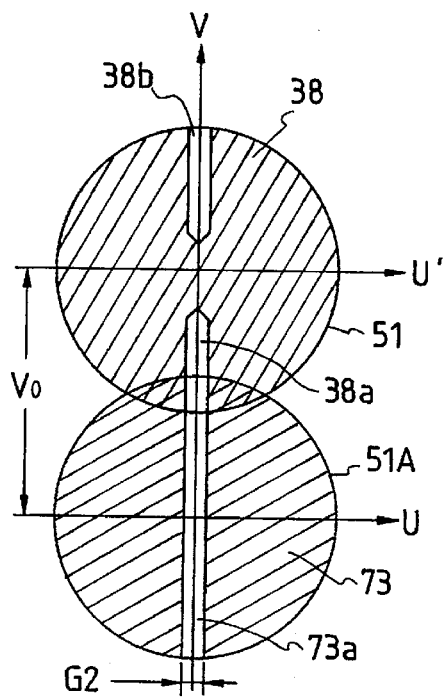
FIG. 18C is a plan view showing a light intercepting member 73 used in the fourth embodiment.

To intercept all of the above-described Fourier transform patterns and pass the light in the patternless area, use can be made of the space filter 73 shown in FIG. 18C. The space filter 73 may be of a shape in which the light transmitting area of a width G2 of the space filter 38 corresponding to the space filter 108 supposed in the sixth embodiment is extended along V axis. That is, a light transmitting area 73a of a width G2 is formed along V axis in the space filter 73, and the other areas of this space filter are light intercepting portions.

Figure 31A:
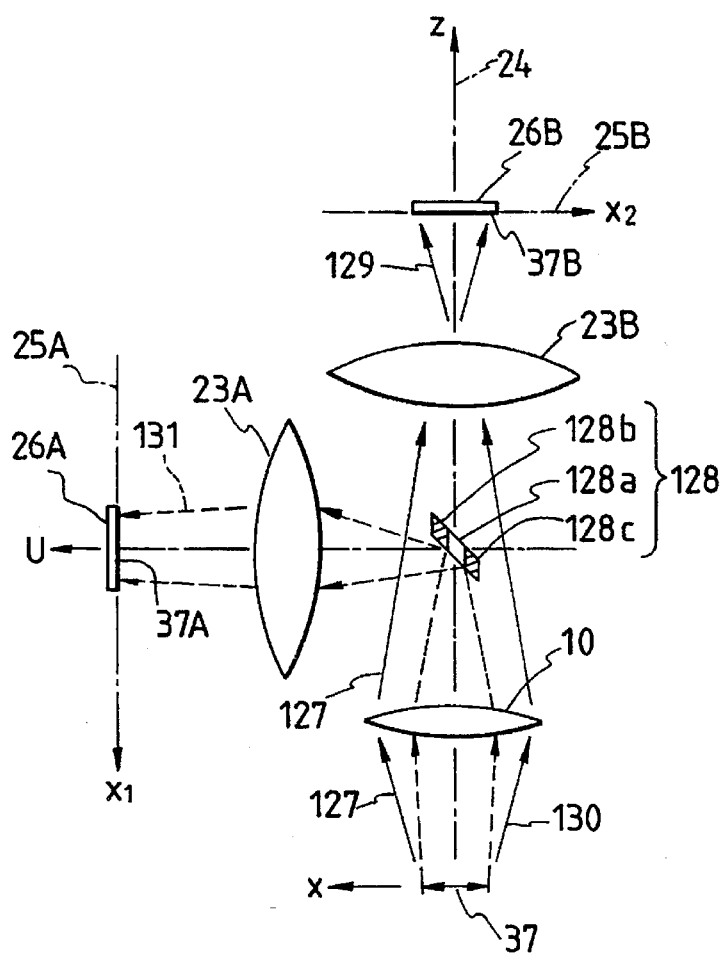
FIG. 31A is a left side view of a light receiving system in FIG. 30A.
Figure 31B:
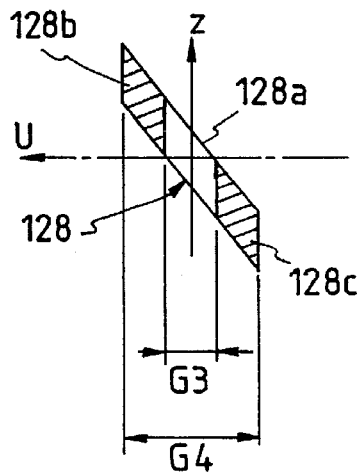
FIG. 31B is an enlarged view showing a partial reflecting mirror 128.

In the present embodiment, the light information on the Fourier transform plane 17 corresponding to the area 73a (see FIG. 18C) of the space filter 73 along V direction is selected by the partial reflecting mirror 128 of FIG. 30A. FIG. 31A is a left side view of FIG. 30A, and FIG. 31B is an enlarged view of the partial reflecting mirror 128 in FIG. 31A. In FIGS. 31A and 31B, the reflecting portion 128a of the partial reflecting mirror 128 turns back the light information of an area of G3 on the Fourier transform plane 17 along V axis by 90° with respect to the optical axis 24 and reflects it in the direction of U axis. The width G3, like the width G2 in FIG. 18C, is determined on the basis of the Fourier transform pattern of the beam of illuminating light itself (which corresponds to the Fourier transform pattern 45A of FIG. 18A).

A first beam of defect carrying light 131 bent in the direction of U axis enters a reverse Fourier transform lens 23A having U axis as its optical axis. By the reverse Fourier transform lens 23A, the filtered light patterns of the dies on the illuminated semiconductive wafer 1 are reversely Fourier-transformed on the image plane (rearward focal plane) 25A of the lens 23A. The reverse Fourier transform lens 23A is located at a distance one time as great as the focal length of the lens 23A from V axis on the rearward focal plane 17 of the Fourier transform lens 10. On the image plane 25A of the lens 23A, the light receiving portion of a one-dimensional photodetector array 26A is disposed about U axis, and the image pickup elements of the photodetector array 26A are arranged on $x_1$ axis conjugate with x axis.

Also, in FIG. 31B, light absorbing members 128b and 128c are provided on the opposite ends of the partial reflecting mirror 128 disposed on the Fourier transform plane 17, and these light absorbing members 128b and 128c intercept or reflect the light information of an area of a width G4 on the Fourier transform plane 17 along V axis, of the beam of light travelling from the Fourier transform lens 10 to the Fourier transform plane 17. The width G4 is determined so as to correspond to the width G0 in FIG. 18B.

In FIG. 31A, a second beam of defect carrying light 129 passed through around the partial reflecting mirror 128 enters a reverse Fourier transform lens 23B. The reverse Fourier transform lens 23B reversely Fourier-transforms the filtered beam of light 129, and the image of a defect on the semiconductive wafer 1 is formed on the image plane (rearward focal plane) 25B of the lens 23B. The reverse Fourier transform lens 23B is located at a distance one time as great as the focal length of the lens 23B from the rearward focal plane 17 of the Fourier transform lens 10. On the image plane 25B of the lens 23B, the light receiving portion of a one-dimensional photodetector array 26B is disposed about the optical axis 24, and the image pickup elements of the photodetector array 26B are arranged on $x_2$ axis conjugate with x axis.

As shown in FIGS. 31A and 31B, the images 32A and 32B of defects present in the die in the illuminated area 32 on the semiconductive wafer 1 are formed on the light receiving surfaces, respectively, of the photodetector arrays 26A and 26B. In the present embodiment, design is made such that defect images of the same magnification are obtained on the light receiving surfaces of the photodetector arrays 26A and 26B. On those light receiving surfaces, there are produced the images of the simple circuit patterns 47, 48, 49 and 50 shown in FIGS. 4A, 4B, 4C and 4D or the other circuit patterns than the rough circuit patterns of substantially the same size as the size of the beam spot on the semiconductive wafer 1 by the beam of illuminating light, besides the images of the defects.

In the present invention, by the construction as described above, there are obtained two defect images corresponding to the reverse Fourier transformation of the filtered light pattern. Further, in FIG. 31A, the image pickup elements of the one-dimensional photodetector arrays 26A and 26B correspond to one another at one to one and are designed so as to correspond to the same object point. The detailed structure of these photodetector arrays 26A and 26B is the same as that of the photodetector arrays in the sixth embodiment of FIGS. 21A to 21E.

In the present embodiment, to obtain the result of defect inspection from image pickup signals corresponding to those two defect images, use can be made of the signal processing systems shown in the sixth embodiment. The relative movement of the illuminated area 37 on the semiconductive wafer 1 may also basically be the same as that in the sixth embodiment.

According to the present embodiment, as described with reference to FIGS. 18A to 18C, the Fourier transform spectrum (spatial frequency component) used for observation is the Fourier spectrum in the area far from the 0-order diffracted light component on the Fourier transform plane 17. Also, the diffracted light from more minute structure has its location on the Fourier transform plane 17 made farther from the 0-order diffracted light. Accordingly, the influence of the original circuit patterns can be reduced and moreover, the detection of any minute defect can be accomplished accurately.

A ninth embodiment of the present invention will now be described with reference to FIG. 32. This embodiment is one in which the optical axis of the light receiving system in the eighth embodiment is inclined from z axis toward the optical axis of the illuminating system, and in FIG. 32, portions corresponding to those in FIGS. 30A, 30B, 31A and 31B are given the same reference characters and need not be described in detail. That is, FIG. 32 shows a defect inspecting apparatus according to the present embodiment, and the present embodiment is entirely the same as the eighth embodiment of FIGS. 30A, 30B, 31A and 31B with the exception that the optical axis 24 of the light receiving system is inclined by an angle N in yz plane with respect to z axis.

Figure 32:
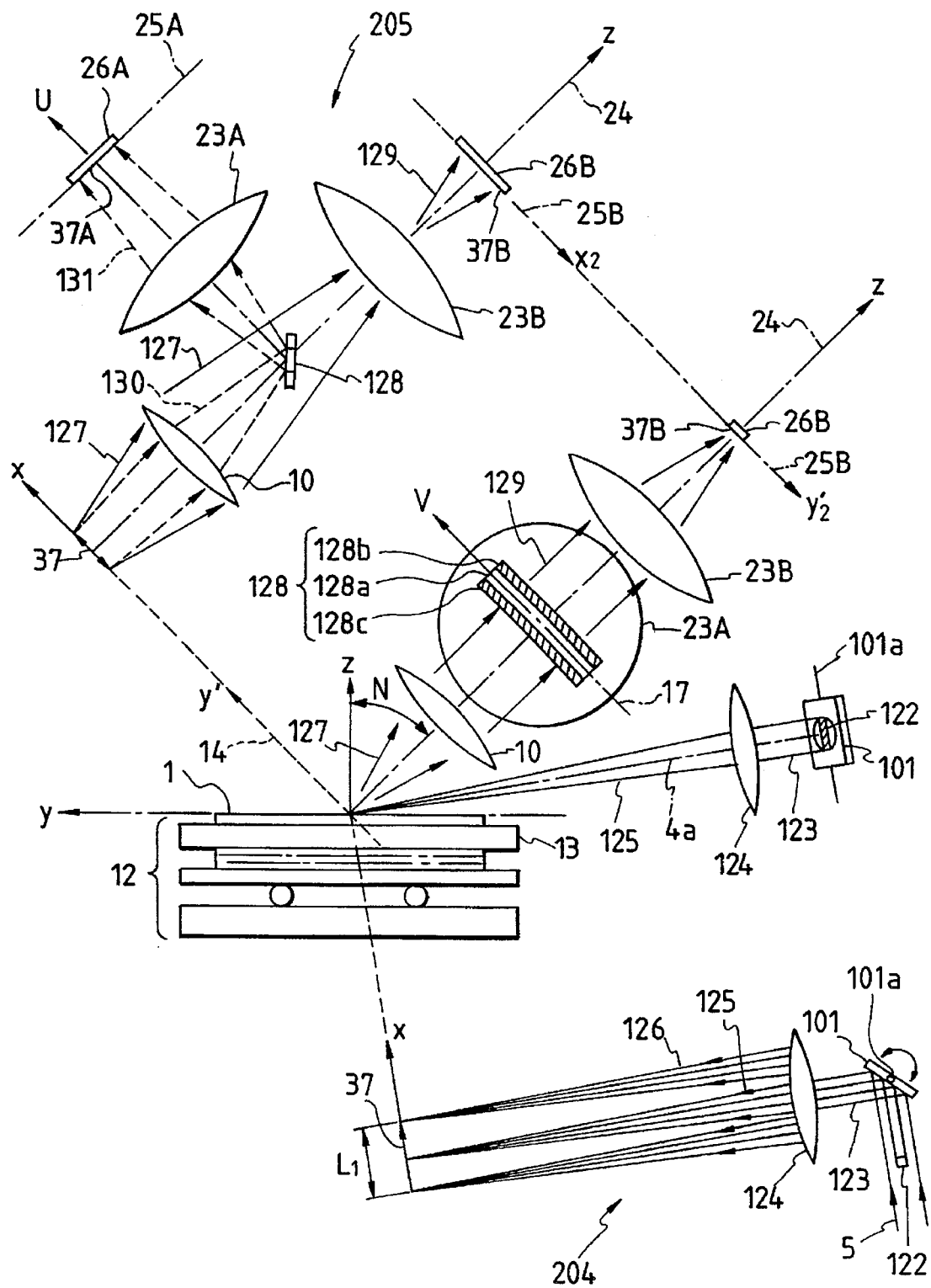
FIG. 32 shows a ninth embodiment of the present invention.

Also, the portion 204 of FIG. 32 shows the illuminating system, and a portion 205 in FIG. 32 shows the light receiving system. In FIG. 32, the optical axis 24 is inclined with respect to the surface of the semiconductive wafer 1 and therefore, the Fourier transform pattern observed in the Fourier transform plane 17 of the Fourier transform lens 10, i.e., UV plane, is a pattern farther from 0-order diffracted light than in the eighth embodiment, but a partial reflecting mirror 128 as a space filter may be the same as that in the eighth embodiment. This is because even if the optical axis 24 is inclined in yz plane, equation (1) is established with respect to the u component of the spatial frequency.

In the present embodiment, the observation area on the Fourier transform plane 17 is farther from 0-order diffracted light than in the eighth embodiment and therefore, the influence of the errorless pattern is further reduced and also, more minute defects can be detected.

A tenth embodiment of the present invention will now be described with reference to FIGS. 33 and 34. This embodiment is an improvement over the eighth embodiment, and in FIGS. 33 and 34, portions corresponding to those in FIGS. 30A, 30B, 31A and 31B are given the same reference characters and need not be described in detail. The difference of the present embodiment from the eighth embodiment lies in the filtering method in the Fourier transform plane 17.

Figure 33:
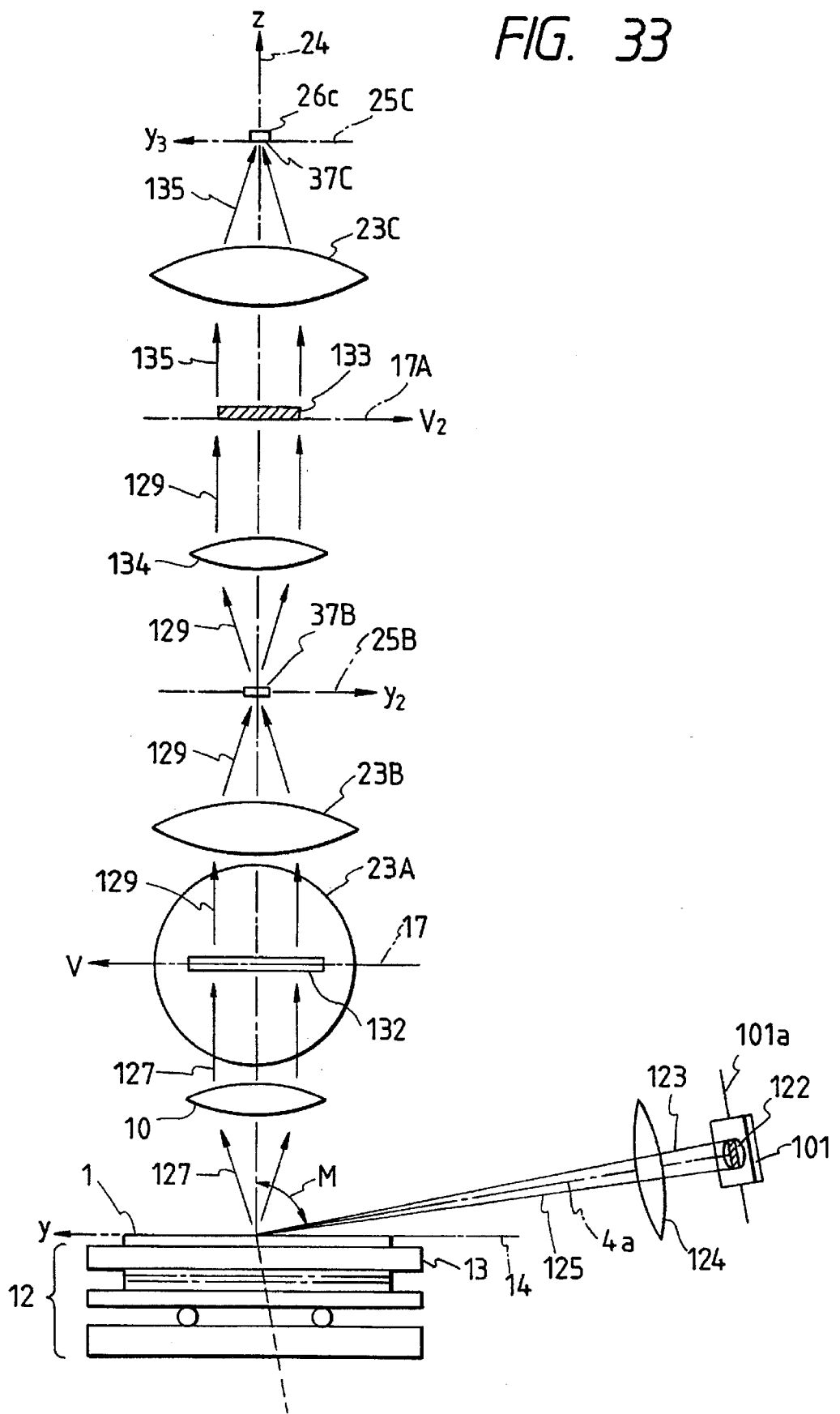
FIG. 33 is a front view showing a tenth embodiment of the present invention.
Figure 34:
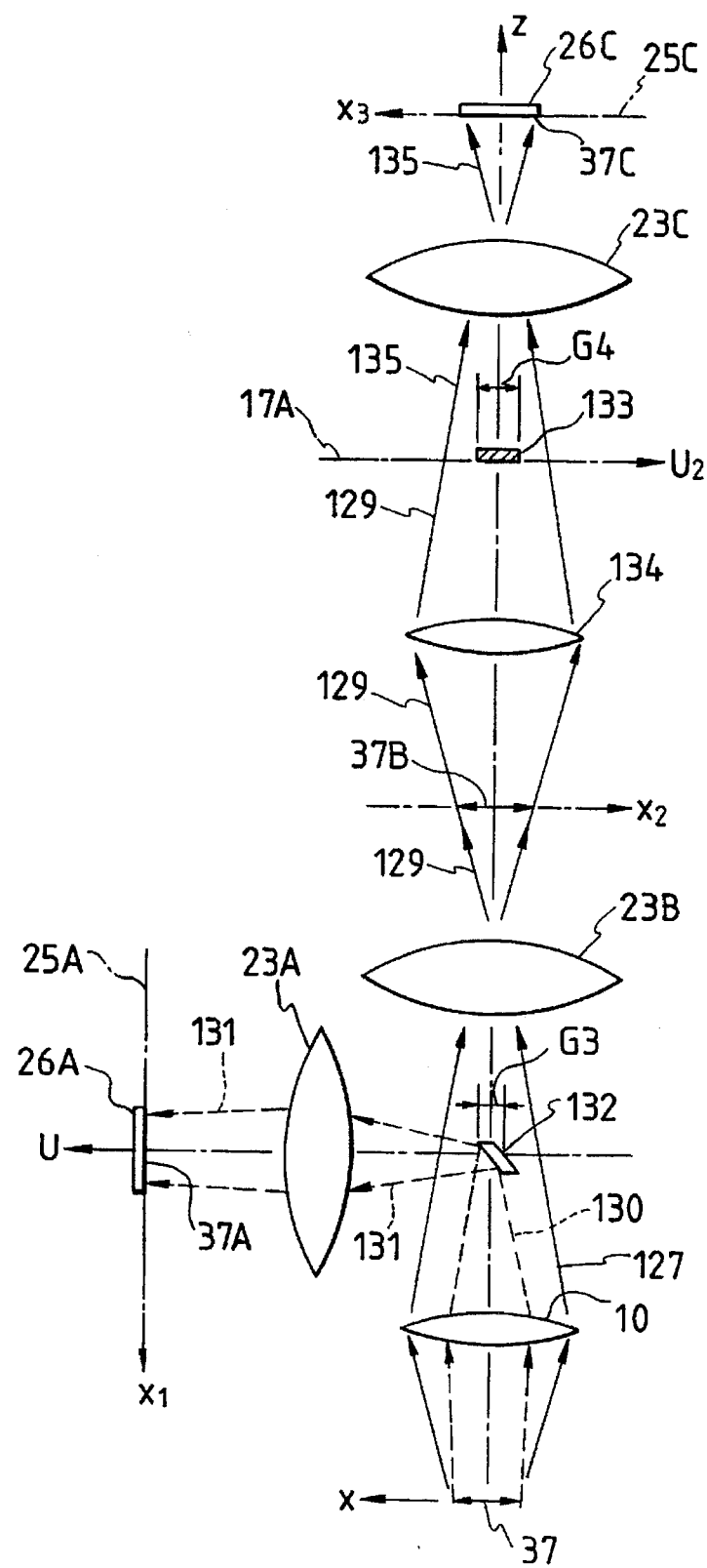
FIG. 34 is a left side view of a light receiving system in FIG. 33.

FIG. 33 is a front view of a defect inspecting apparatus according to the present embodiment, and FIG. 34 is a left side view of the light receiving system of FIG. 33. As shown in FIG. 34, in the present embodiment, a rectangular reflecting mirror 132 is disposed on the Fourier transform plane 17 along V axis, and a beam of light reflected by this reflecting mirror 132 is directed as a first beam of defect carrying light 131 to the reverse Fourier transform lens 23A. In that the first beam of defect carrying light 131 is thus separated on the Fourier transform plane 17, the present embodiment is the same as the eighth embodiment in which the first beam of defect carrying light 131 and the second beam of defect carrying light 129 are separated from each other by the partial reflecting mirror 128 on the Fourier transform plane 17.

In the present embodiment, however, the second beam of defect carrying light 129 passed through around the reflecting mirror 132 on the Fourier transform plane 17 is not intactly directed to the photodetector array 26C, but as shown in FIG. 33, the second beam of defect carrying light 129 is imaged on the image plane (rearward focal plane) 25B of the lens 23B by the reverse Fourier transform lens 23B. The reverse Fourier transform lens 23B is located at a distance one time as great as the focal length of the lens 23B from the Fourier transform plane 17, and the spatial image 37B of a defect in the illuminated area on the semiconductive wafer 1 is formed on the image plane 25B.

Further, by a Fourier transform lens 134 provided at a distance one time as great as the focal length thereof from the image plane 25B, the Fourier transform pattern of the spatial image 37B is formed on the rearward focal plane 17A of the lens 134. $U_2$ axis and $V_2$ axis on the Fourier transform plane 17A are conjugate with U axis and V axis, respectively, on the Fourier transform plane 17, and in the present embodiment, design is made such that the magnification between the two Fourier transform planes 17 and 17A becomes 1. Also, a light intercepting member 133 of a width G4 is installed along $V_2$ axis on the Fourier transform plane 17A. The width G4 of the light intercepting member 133 in the direction of $U_2$ axis corresponds to the width G0 in FIG. 18A, and is determined by the Fourier transform pattern of the beam of illuminating light itself.

A beam of defect carrying light 135 after filtered by the light intercepting member 133 is reversely Fourier-transformed by a reverse Fourier transform lens 23C, and the image 37C of a defect is formed on the rearward focal plane 25C of the lens 23C. In the present embodiment, the magnification between the two conjugate image planes 25B and 25C is 1. In the other points, the construction of the present embodiment is similar to the construction of the eighth embodiment.

In the present embodiment, stricter filtering than the filtering in the eighth embodiment is effected by the filtering method as described above. This owes to the fact that the unreliability of filtering attributable to the light absorbing members 128b and 128c as the space filters in the eighth embodiment shown in FIG. 31A becoming somewhat far from the Fourier transform plane 17 is eliminated.

Also, the above embodiments have been described with respect to the case when the reflected light from the substrate to be inspected is detected. However, the present invention is not restricted thereto, but defect inspection may be effected by the light transmitted through a light transmitting substrate to be inspected.

Further, without the light intercepting member being provided between the light source and the substrate to be inspected, the detection light may be divided by a mirror or the like and the signals of a plurality of image pickup elements corresponding to the divided lights may be compared.

Of course, the present invention is not restricted to the above-described embodiments, but can assume various constructions without departing from the gist of the invention.

What is claimed is:

1. A defect inspecting apparatus for inspecting a surface of a substrate having a pattern thereon, including:
   a light source which supplies illuminating light;
   an illuminating system which applies the illuminating light from said light source onto the surface of said substrate to be inspected;
   a lens system for condensing light from said surface to be inspected and creating a spatial frequency spectrum on a Fourier transform plane to said surface to be inspected or a plane conjugate therewith;
   a light intercepting member having a light intercepting portion which sets a spectrum-free area at a region along at least one of two axes perpendicular to each other on said Fourier transform plane or said plane conjugate therewith in the absence of a defect on said surface to be inspected, said light intercepting member being disposed between said light source and said substrate and being effective to intercept part of said illuminating light;
   a spatial filter which is disposed on said Fourier transform plane or the plane conjugate therewith, which passes therethrough a condensed beam of light in said spectrum-free area created from a defect on said surface to be inspected, and which blocks light from said pattern without relying on the directivity of said pattern;
   a light receiver which receives said beam of light passed through said spatial filter and outputs a photoelectric signal; and
   a signal processor which determines means a state of the surface of said substrate to be inspected based on said photoelectric signal.

2. The defect inspecting apparatus of claim 1, wherein said illuminating system has a condenser which condenses said illuminating light incident on said substrate, and a scanner is provided to scan said illuminating light condensed on said substrate and said substrate relative to each other.

3. The defect inspecting apparatus of claim 1, further including:
   a first means for rotating driver which rotates said light intercepting member about the optical axis of the optical system of said illuminating system;
   a second driver which rotates said spatial filter about the optical axis of said lens system; and
   a controller which controls said first driver and said second driver so that said light intercepting member and said spatial filter may be rotated in synchronism with each other.

4. The defect inspecting apparatus of claim 1, wherein said illuminating system causes said illuminating light to be obliquely incident on said surface to be inspected.

5. The defect inspecting apparatus of claim 1, wherein said illuminating light is monochromatic light.

6. The defect inspecting apparatus of claim 1, wherein said illuminating light is a plurality of monochromatic lights or light having a continuous wavelength spectrum.

7. A defect inspecting apparatus for inspecting a surface of a substrate having a pattern thereon, including:
   a light source which supplies illuminating light;
   an illuminating system which applies the illuminating light from said light source onto the surface of said substrate to be inspected;
   a lens system for condensing light created from said surface to be inspected and creating a spatial frequency spectrum on a Fourier transform plane to said surface to be inspected or a plane conjugate therewith;
   a light intercepting member having a light intercepting portion which sets a spectrum-free area at a region along at least one of two axes perpendicular to each other on said Fourier transform plane or said plane conjugate therewith in the absence of a defect on said surface to be inspected, said light intercepting member being disposed between said light source and said substrate and being effective to intercept part of said illuminating light;

a dividing member which divides a condensed beam of light from said substrate into a plurality of beams of light, said condensed beam of light being created from a defect on said surface to be inspected, said dividing member being positionally related to said spectrum-free area so as to inhibit said dividing member from dividing light created from said pattern;

a plurality of light receivers which convert the plurality of beams of light into photoelectric conversion signals; and a signal processor which determines a state of the surface of said substrate based on said plurality of photoelectric conversion signals.

8. The defect inspecting apparatus of claim 7, wherein said dividing member is a plurality of mirrors.

9. The defect inspecting apparatus of claim 8, wherein said dividing member wave-front-divides said beam of light.

10. The defect inspecting apparatus of claim 7, wherein said dividing member is provided in said spectrum-free area.

11. The defect inspecting apparatus of claim 7, wherein said dividing member has a plurality of mirrors and a spatial filter which intercepts the spatial frequency spectral component of the pattern on said substrate.

12. The defect inspecting apparatus of claim 7, wherein said illuminating system causes said illuminating light to be obliquely incident on said surface to be inspected.

13. A defect inspecting apparatus for inspecting a surface of a substrate having a pattern thereon, including:

a light source which supplies illuminating light;

an illuminating system which applies the illuminating light from said light source onto the surface of said substrate to be inspected;

a lens system for condensing light created from said surface to be inspected and creating a spatial frequency spectrum on a Fourier transform plane to said surface to be inspected or a plane conjugate therewith;

a spatial filter which is disposed between said light source and said substrate and which intercepts the spatial frequency spectrum of the pattern on said substrate;

a dividing member which is disposed on said Fourier transform plane or the plane conjugate therewith and which divides a beam of light from said substrate into a plurality of beams of light, said beam of light from said substrate being created by a defect on said surface to be inspected, said dividing member being positionally related to said spatial filter so as to inhibit said dividing member from dividing light created from said pattern;

a plurality of light receivers which convert the plurality of beams of light into photoelectric conversion signals; and a signal processor which determines a state of said surface of said substrate based on said plurality of photoelectric conversion signals.

14. The defect inspecting apparatus of claim 13, wherein said illuminating system applies the illuminating light onto the pattern on said substrate from an inclined direction, and said dividing member is provided in an area wherein the spatial frequency spectrum of the circuit pattern is absent when there is no defect on said surface of said substrate.

* * * * *